(12) United States Patent
Lee et al.

(10) Patent No.: US 9,719,127 B2
(45) Date of Patent: Aug. 1, 2017

(54) DUAL INDUCIBLE VECTORS AND CELL LINES

(71) Applicant: The Regents of the University of California, Oakland, CA (US)

(72) Inventors: Benhur Lee, Los Angeles, CA (US); Kelechi Chikere, Los Angeles, CA (US); Tom Chou, Venice, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/385,824

(22) PCT Filed: Mar. 15, 2013

(86) PCT No.: PCT/US2013/032178
§ 371 (c)(1),
(2) Date: Sep. 17, 2014

(87) PCT Pub. No.: WO2013/142341
PCT Pub. Date: Sep. 26, 2013

(65) Prior Publication Data
US 2015/0125850 A1    May 7, 2015

Related U.S. Application Data

(60) Provisional application No. 61/613,129, filed on Mar. 20, 2012.

(51) Int. Cl.
*C12Q 1/66* (2006.01)
*C12Q 1/68* (2006.01)
(Continued)

(52) U.S. Cl.
CPC ............. *C12Q 1/66* (2013.01); *C12N 5/0686* (2013.01); *C12Q 1/6897* (2013.01); *C12Q 1/703* (2013.01);
(Continued)

(58) Field of Classification Search
None
See application file for complete search history.

(56) References Cited

U.S. PATENT DOCUMENTS

2009/0235370 A1    9/2009  Tannous
2011/0059439 A1*   3/2011  Bhaumik ........... C12N 15/1086
                                                          435/6.14

FOREIGN PATENT DOCUMENTS

WO    WO 2005/033280 A2 *  9/2004
WO    WO 2005/033280 A2 *  4/2005
(Continued)

OTHER PUBLICATIONS

McCormick et al. Efficient delivery and regulable expression of hepatitis C virus full-length and minigenome constructs in hepatocyte-derived cell lines using baculovirus vectors. J. Gen. Virol. 2002; 83:383-394.*
(Continued)

*Primary Examiner* — Janet L Andres
*Assistant Examiner* — Stuart W Snyder
(74) *Attorney, Agent, or Firm* — Karen S Canady; canady + lortz LLP

(57) ABSTRACT

The invention pertains to a novel cell line, an HIV tat-rev dependent GFP-Gaussia luciferase Reporter cell line, known henceforth as the GGR cell line, that detects pseudotype and replication competent HIV (cloned or uncloned isolates, in cell media or human serum) rapidly and with high sensitivity. This GGR cell line provides an improved method of characterizing the entry phenotype of HIV envelope genes,
(Continued)

Figures 1A, 1B:
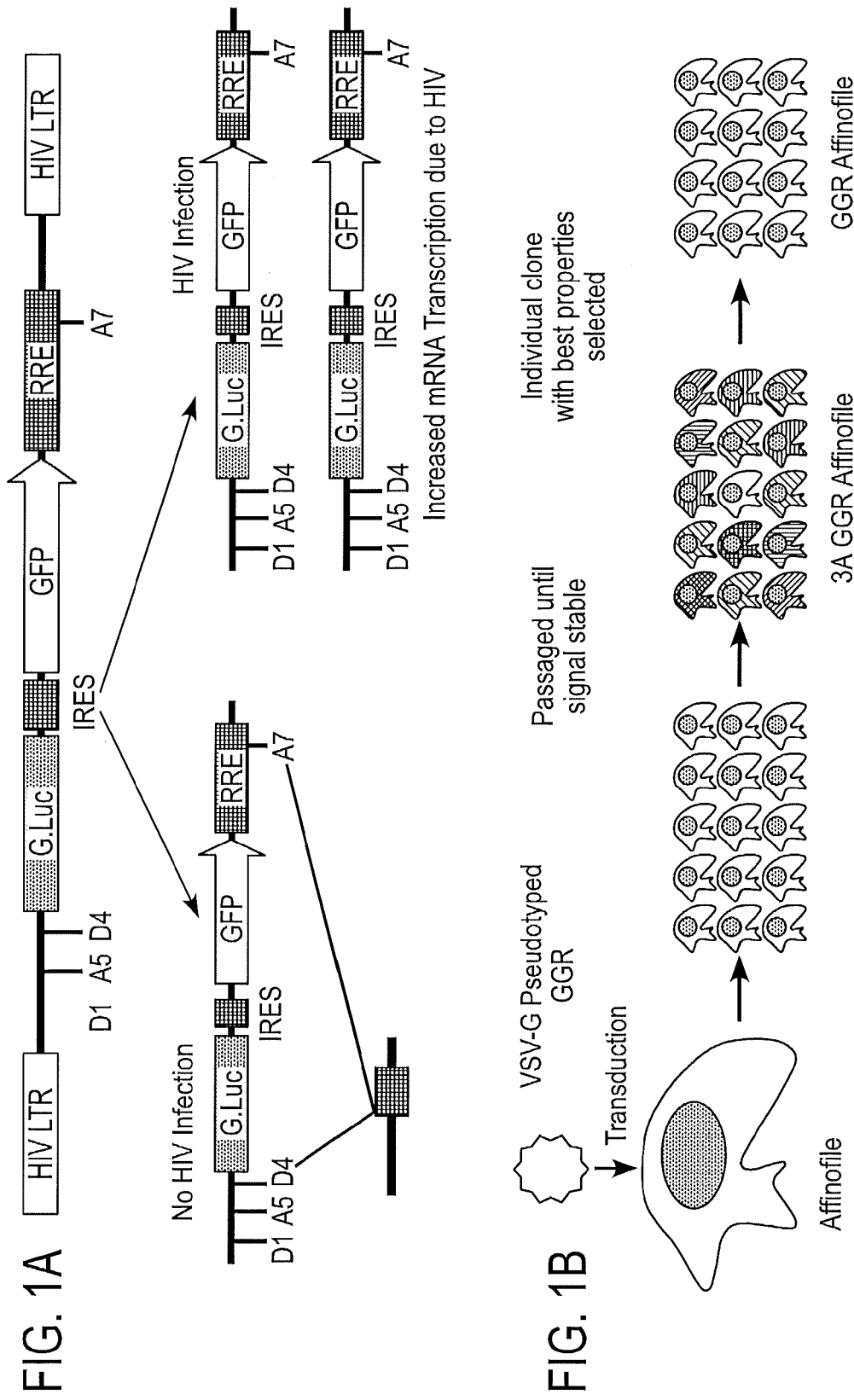

and detecting and examining primary HIV samples in the context of laboratory research, clinical trial monitoring, and medical diagnostics. Examples include, but are not limited to, determining the functional HIV viral load, responsiveness to treatment, characterization of viral co-receptor usage (testing for viral co-receptor usage, i.e., CCR5 vs CXCR4, as required prior to prescribing FDA-approved CCR5 inhibitors), and characterization of other viral or drug resistance phenotypic properties to guide treatment.

8 Claims, 47 Drawing Sheets

(51) Int. Cl.
  *C12Q 1/70* (2006.01)
  *C12N 5/071* (2010.01)
(52) U.S. Cl.
  CPC .............. *C12N 2740/16031* (2013.01); *C12N 2840/60* (2013.01); *G01N 2333/163* (2013.01)

(56) References Cited

FOREIGN PATENT DOCUMENTS

WO   WO 2008-066608   6/2008
WO   WO 2008-144052   11/2008
WO   WO 2011-029798   3/2011

OTHER PUBLICATIONS

2002 Invitrogen product literature.*
Thorne et al. Illuminating Insights into Firefly Luciferase and Other Bioluminescent Reporters Used in Chemical Biology. Chemistry & Biology. 2010; 17: 646-657.*
La et al., *An ecdysone and tetracycline dual regulatory expression system for studies on Rac1 small GTPase-mediated signaling*, 285(3) American Journal of Physiology Cell Physiology C711-C719 (May 7, 2003).
International Search Report mailed on Jun. 28, 2013, in corresponding PCT Application PCT/US2013/032178.

* cited by examiner

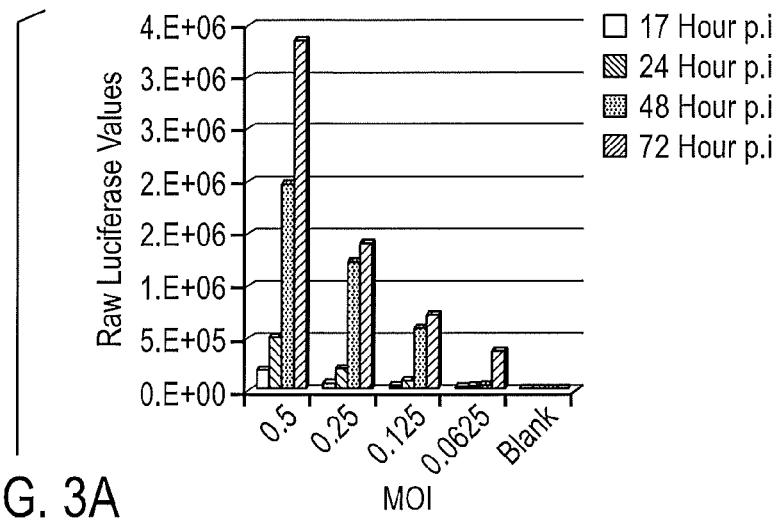
FIG. 3A
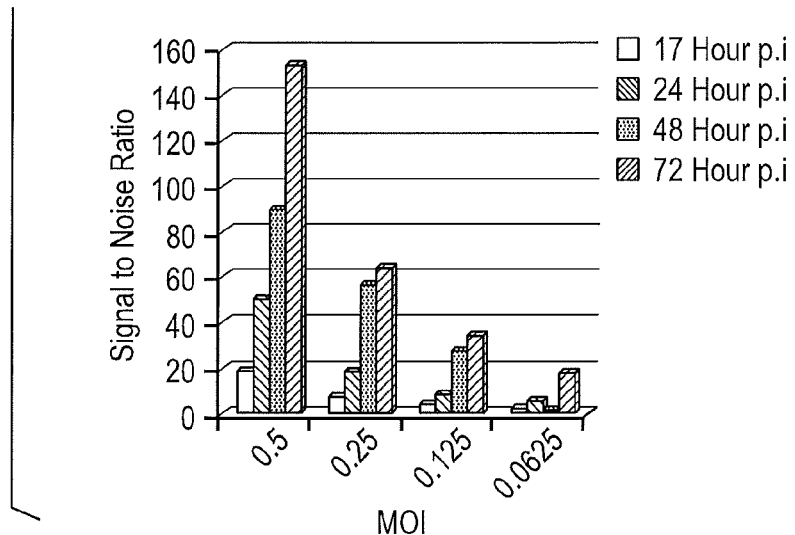
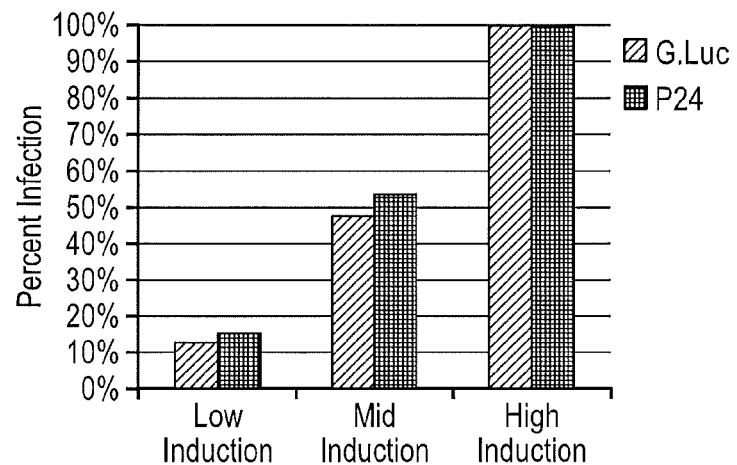
FIG. 3B

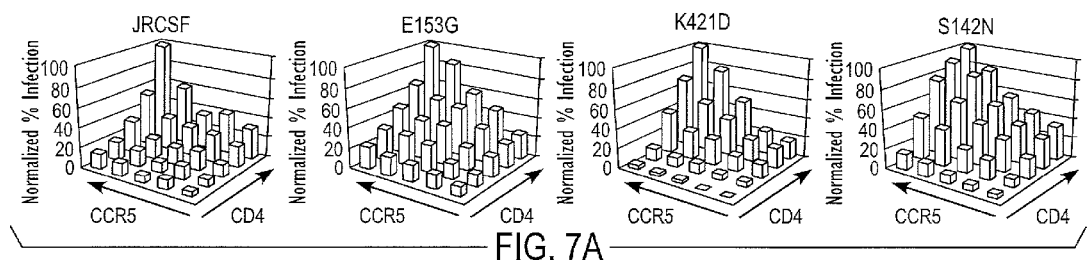
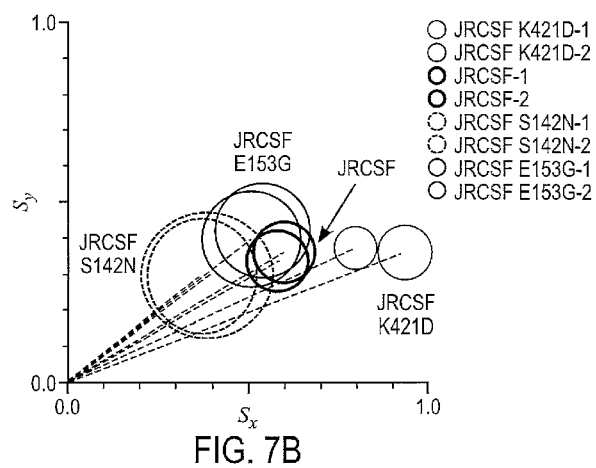
FIG. 7A
FIG. 7B
FIG. 7C
| Mutant | CD4 Usage | CCR5 Usage |
|---|---|---|
| JRCSF E153G[1] | ↑↑ | ↑↑ |
| JRCSF K421D[2] | ↓ | ↓↓ |
| JRCSF S142N[3] | ↑ | ↑↑↑ |

FIG. 10
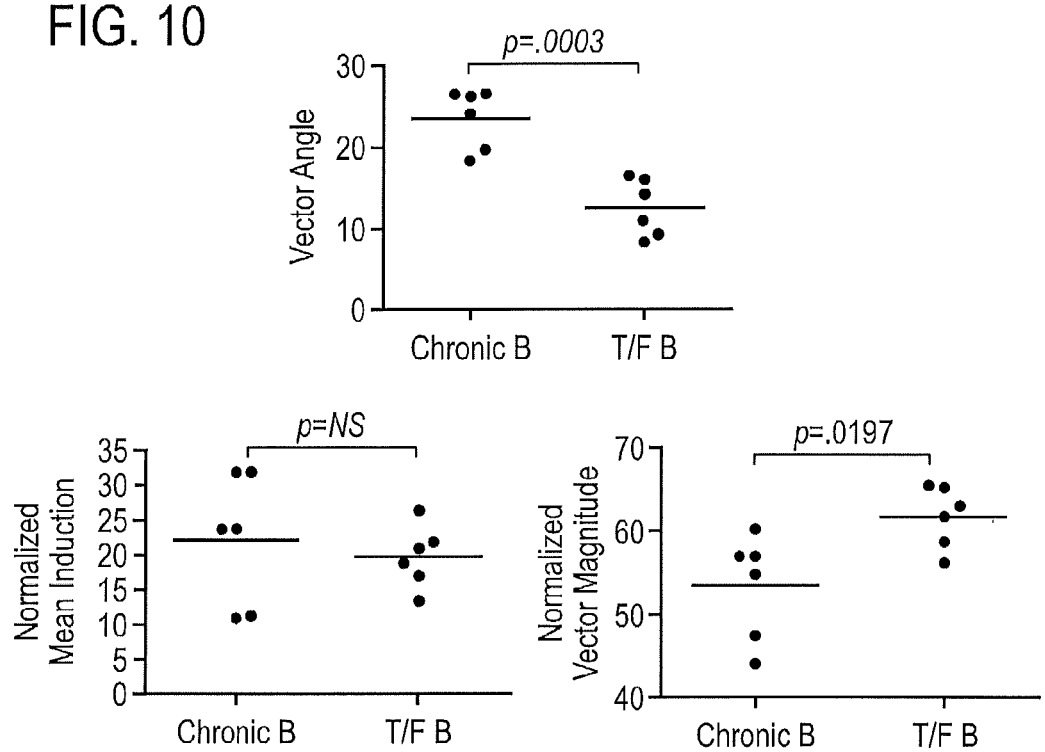
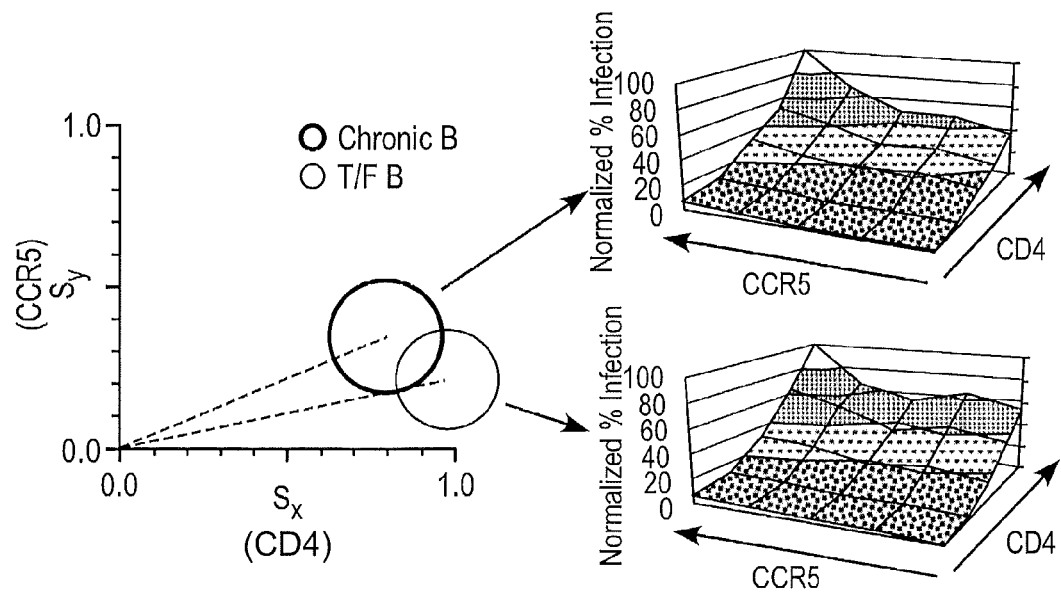

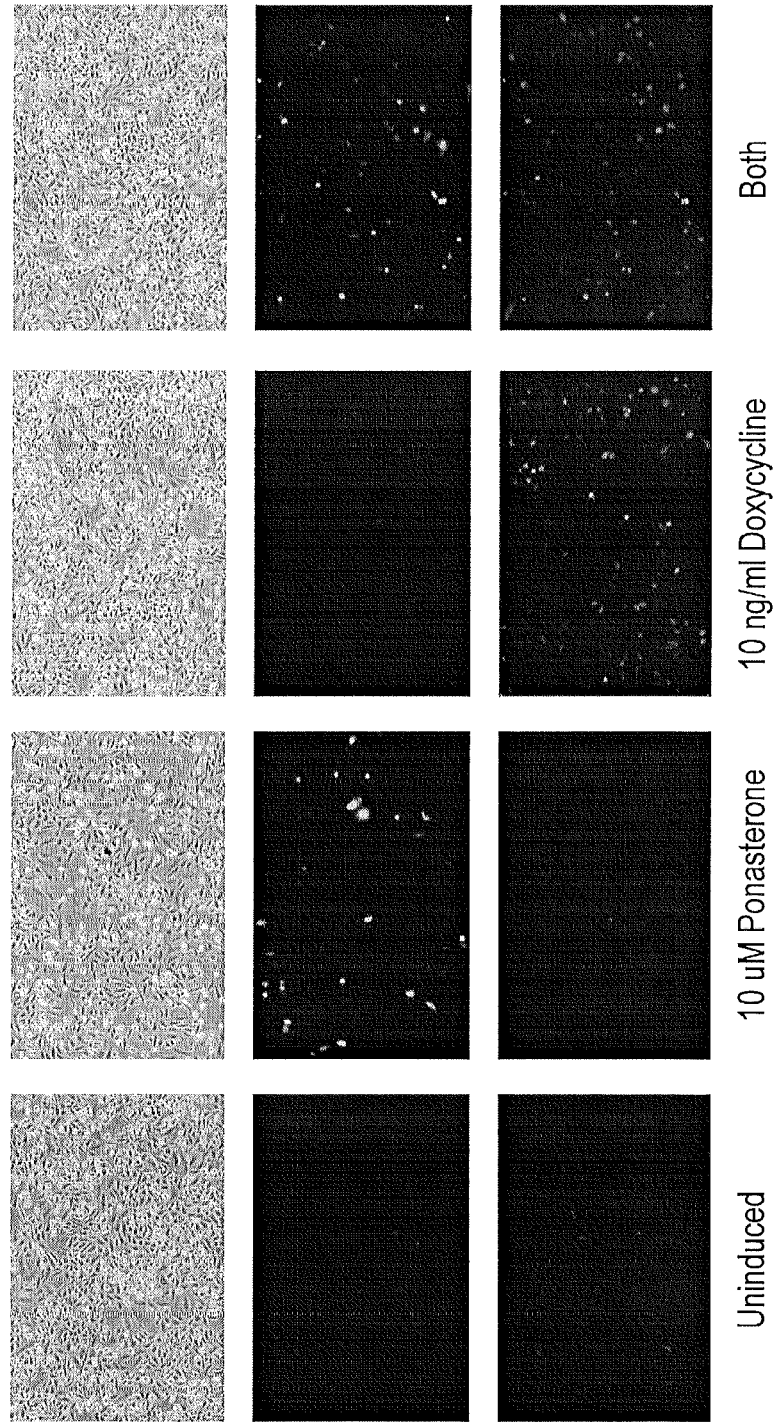

$\theta$, sensitivity vector <u>angle</u>, measures whether the infectivity of a given Env is more sensitive to changes in CD4 versus CCR5 levels $\Delta$, sensitivity vector <u>amplitude</u>, measures the average "steepness" of the infectivity surface $F

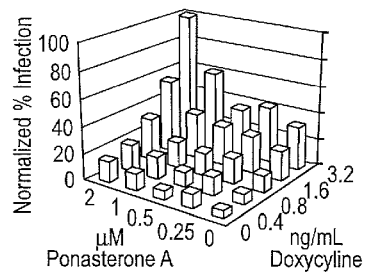
FIG. 21A
wt JR-CSF
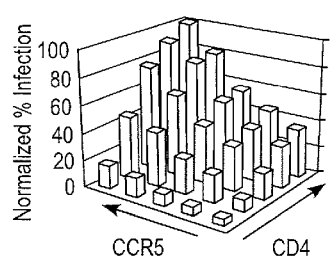
FIG. 21B
S142N
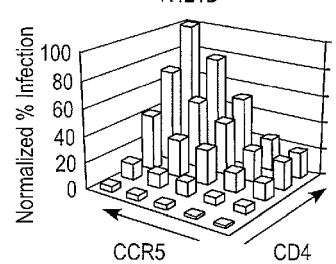
FIG. 21C
K421D
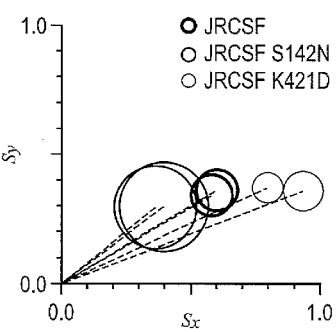
FIG. 21E
|  | Vector Metrics | | |
|---|---|---|---|
|  | Angle, $\theta$ | Mean Infectivity M | Amplitude, $\Delta$ |
| wtJR-CSF | 30.5 | 20.0 | 50.5 |
| S142N | 38.0 | 40.5 | 36.0 |
| K421D | 23.0 | 16.5 | 69.5 |
FIG. 21D

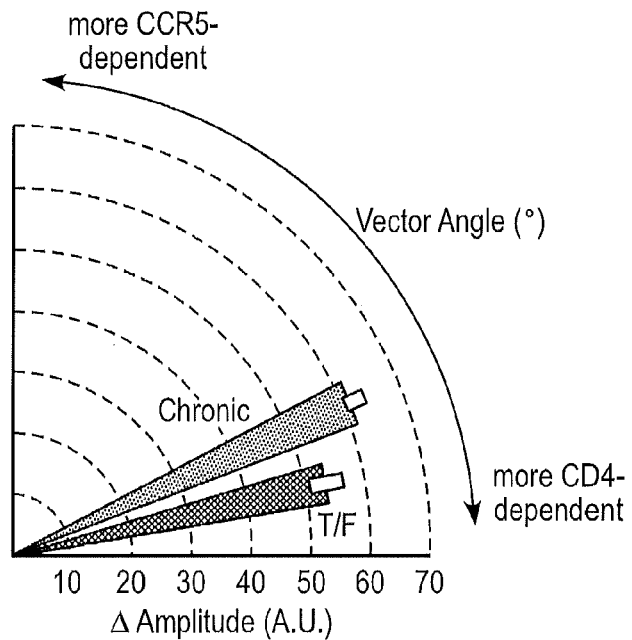
FIG. 23F
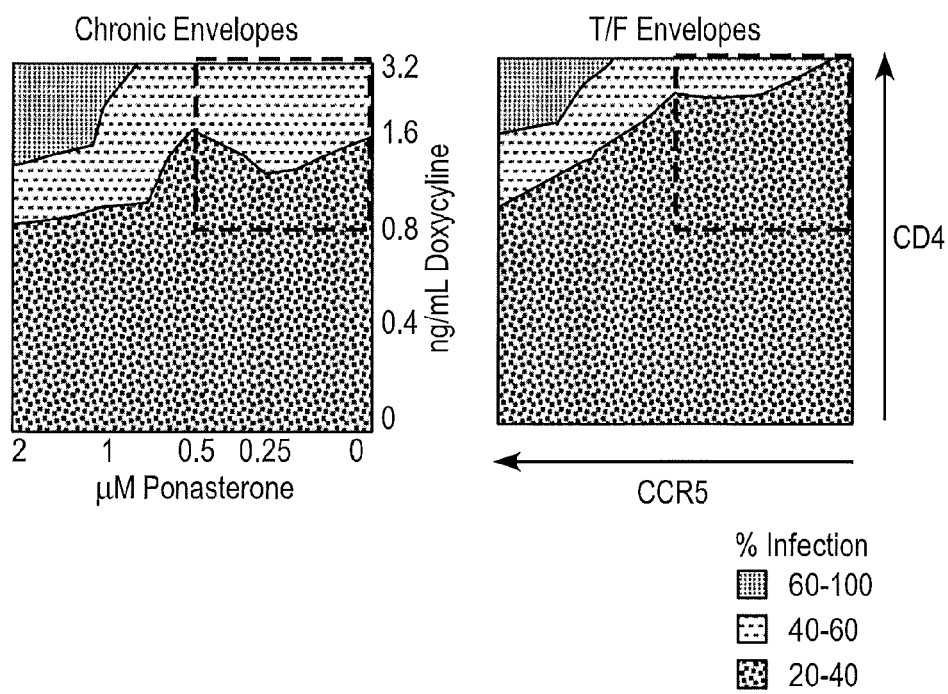

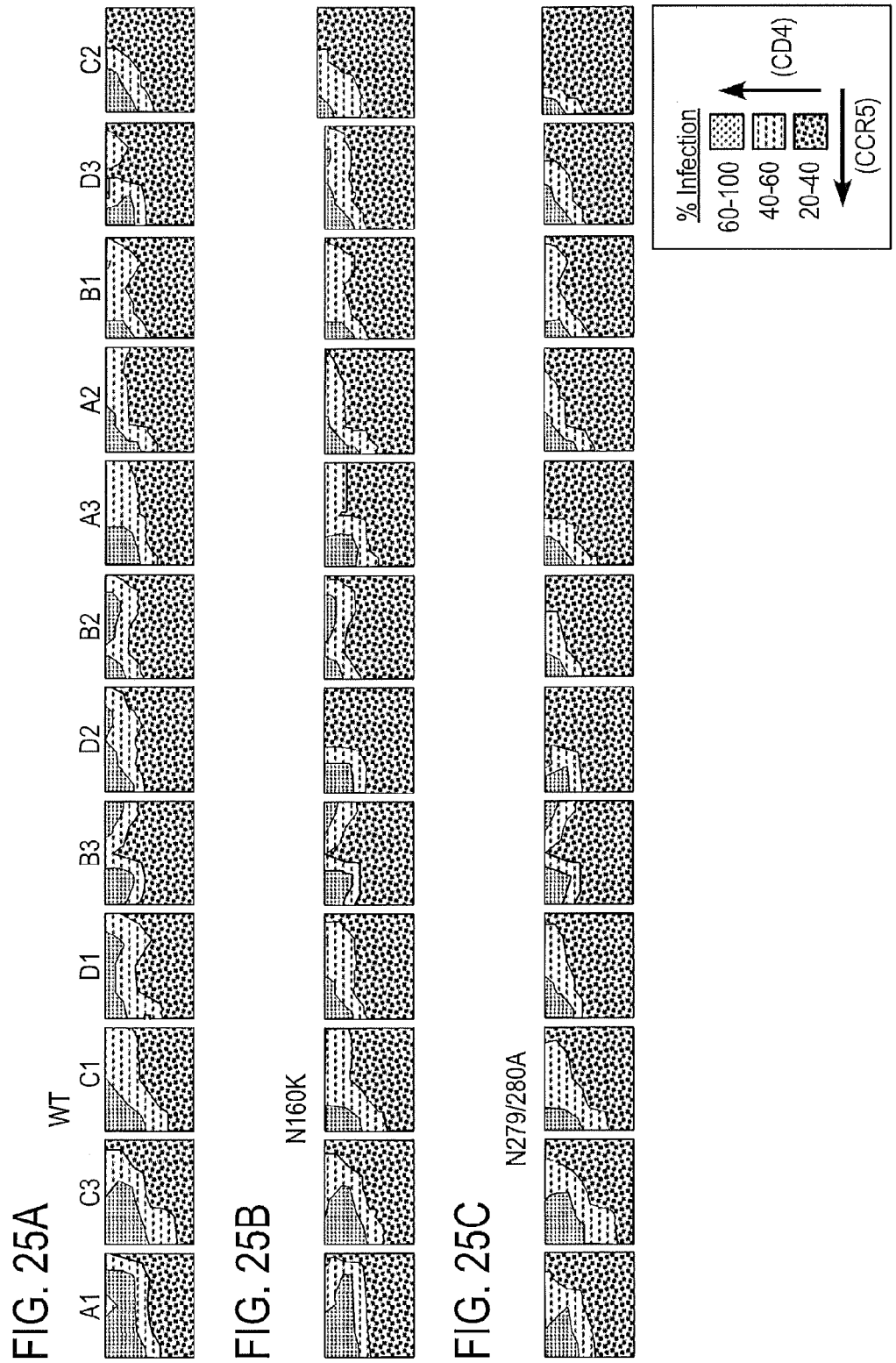

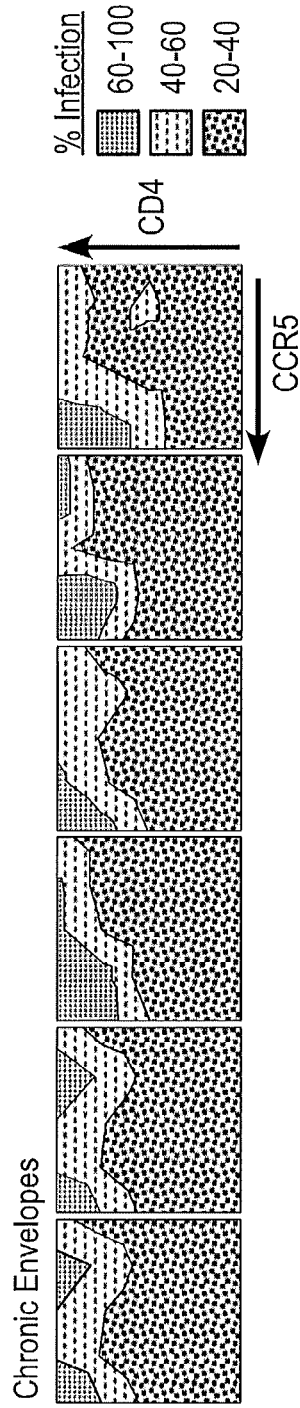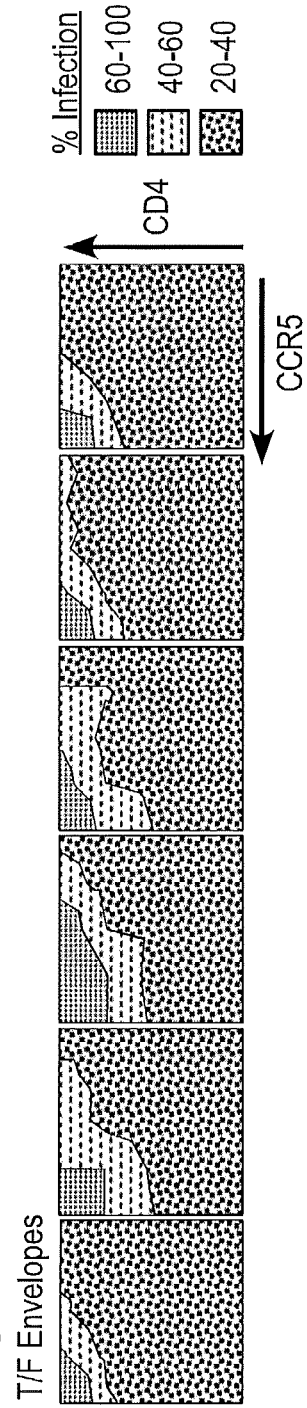
FIG. 27A Chronic Envelopes
FIG. 27B T/F Envelopes

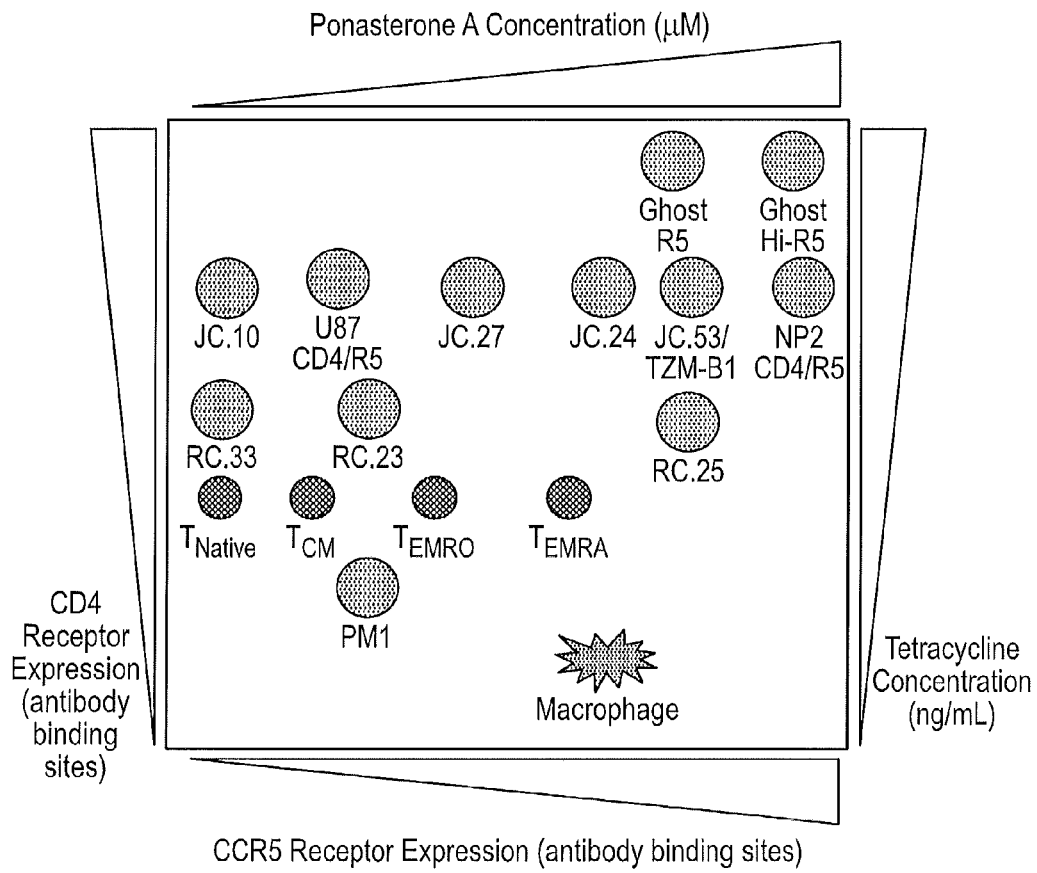

Based on results found in papers below.
1. Use of Tissue Culture Cell Lines to Evaluate HIV Antiviral Resistance.
2. Effects of CCR5 and CD4 Cell Surface concentraions on infections by Macrophage of Human Immunodeficiency Virus Type 1
3. HIV-1 predisposed to Acquiring Resistance to Maraviroc (MVC) and Other CCR5 Antagonists in Vitro Has An Inherent, Low-level Ability To Utilize MVC-bound CCR5 For Entry.
4. Qualification of CD4, CCR5, and CXCR4 levels on lymphocyte subsets, deadrate cells, and differentially conditioned monocyte-derived macrophages

FIG. 31A

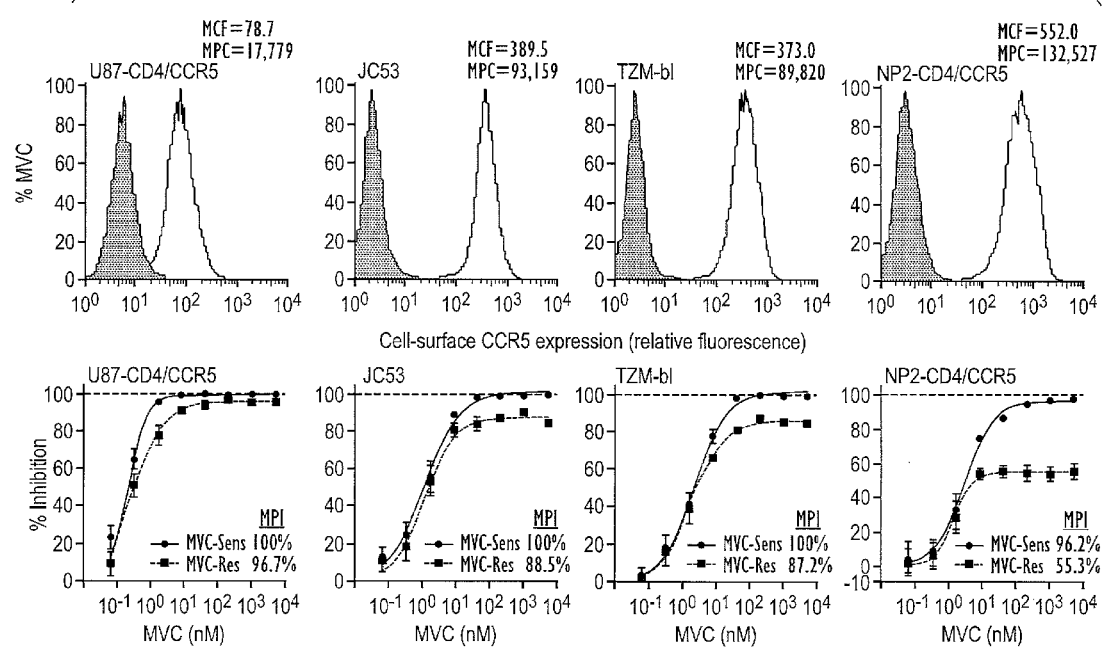

DUAL INDUCIBLE VECTORS AND CELL LINES

CROSS-REFERENCE TO RELATED APPLICATIONS

This application is a U.S. National Stage pursuant to 35 U.S.C. §371 of International Patent Application PCT/US2013/032178, filed on Mar. 15, 2013, and published as WO 2013/142341 on Sep. 26, 2013, which claims priority to U.S. Provisional Patent Application 61/613,129, filed on Mar. 20, 2012, all of which are incorporated herein by reference in their entireties for all purposes.

STATEMENT REGARDING FEDERALLY SPONSORED RESEARCH

This invention was made with Government support under AI092218 awarded by the National Institutes of Health. The Government has certain rights in the invention.

The invention pertains to a novel cell line, an HIV tat-rev dependent GFP-Gaussia luciferase Reporter cell line, known henceforth as the GGR cell line, that detects pseudotype and replication competent HIV (cloned or uncloned isolates, in cell media or human serum) rapidly and with high sensitivity. This GGR cell line provides an improved method of characterizing the entry phenotype of HIV envelope genes, and detecting and examining primary HIV samples in the context of laboratory research, clinical trial monitoring, and medical diagnostics. Examples include, but are not limited to, determining the functional HIV viral load, responsiveness to treatment, characterization of viral co-receptor usage (testing for viral co-receptor usage, i.e., CCR5 vs CXCR4, as required prior to prescribing FDA-approved CCR5 inhibitors), and characterization of other viral or drug resistance phenotypic properties to guide treatment.

BACKGROUND OF THE INVENTION

Human immunodeficiency virus (HIV) binds and enters cells via interaction of its envelope glycoprotein gp120 with CD4 and either the CCR5 or the CXCR4 chemokine co-receptor. Binding of CD4 to gp120 causes a structural change in the envelope complex which exposes the chemokine binding domains of gp120. This binding induces fusion of the viral and target cell membranes.

HIV-1 affinity for CD4 and CCR5 is associated with differential pathogenicity. Therefore, a dually inducible cell line based system that quantitatively and comprehensively characterizes viral entry efficiency as a co-dependent function of CD4 and CCR5 expression levels has been produced. This receptor affinity profiling system (Affinofile) has revealed biologically relevant phenotypes in viral envelope proteins (envs) with differential CD4/CCR5 usage efficiencies. For example, Elite Suppressor envs have shown reduced efficiency of CD4/CCR5 usage compared to Chronic Progressor envs, and for vicriviroc-resistant envelopes, the degree of resistance is a function of the level of CCR5 cell surface density.

One method of determining HIV receptor usage is through HIV indicator cell lines. Several HIV indicator cell lines are currently available. However, all HIV indicator cell lines currently available use the increased production of a fluorescent protein or a (firefly) luciferase protein as an indication of infection. The use of only a fluorescent protein would require the laborious preparation of the cells and examining of cells on a fluorescent detection system. Alternatively, the use of nonsecreted luciferase would require careful attention to non-trivial matters such as complete lysis of cells before assessment of luciferase activity. Moreover, GFP or firefly (or even Renilla-luciferase) luciferase detection are endpoint assays, since the cells have to be fixed or lysed to assess HIV infection.

Additionally, all indicator cell lines express the receptor (CD4) and co-receptor (CCR5) for HIV at fixed, often over-expressed supraphysiological levels. This hinders the utility of those cell lines because different HIV isolates have varying capacity to use the receptor and co-receptor found at different expression levels on various cell types in vivo. Accordingly, the need exists in the field for an improved method for detecting pseudotype and/or replication competent HIV, from cloned or uncloned isloates, in cell media or human serum.

SUMMARY OF THE INVENTION

One aspect of the invention is a cell line comprising a tat/rev dependent reporter lentiviral vector that expresses secreted Gaussia Luciferase in tandem with enhanced green fluorescent protein (GFP).

An additional aspect of the invention is a method for detecting pseudotype and/or replication competent HIV, from cloned or uncloned isloates, in cell media or human serum via an HIV tat-rev dependent GFP-Gaussia luciferase Reporter cell line (GGR) comprising culturing said GGR cell line; exposing said GGR cell line to said HIV; and assaying for the presence of secreted Gaussia luciferase. This may also be done wherein the cell line is scalable to a 96- or 384-well format. This may also be done to characterize the entry phenotype of HIV envelope genes; to detect and examine primary HIV samples in the context of laboratory research, clinical trial monitoring, and/or medical diagnostics; to determine functional HIV viral load, responsiveness to HIV treatment, and/or characterize viral co-receptor usage.

A further aspect of the invention is a diagnostic kit for assaying a biological sample, said kit comprising an HIV tat-rev dependent GFP-Gaussia luciferase reporter cell line for detecting HIV, one or more reagents useful for facilitating said detection, and instructions for use of said kit.

A further aspect of the invention is a vector comprising the transactivators of the tetracycline and ponasterone inducible systems and the FRT-LacZeo selection cassette wherein the vector allows inducible expression of two genes of interest and a high expression of the selectable markers, LacZ and Zeocin. One such vector is set forth in FIG. 13.

A further aspect of the invention is a vector comprising Gaussia Luciferase under the control of the ponasterone inducible system and Firefly Luciferase under the control of the TenOn3G inducible system. One such vector is set forth in FIG. 15.

Figure 13A:
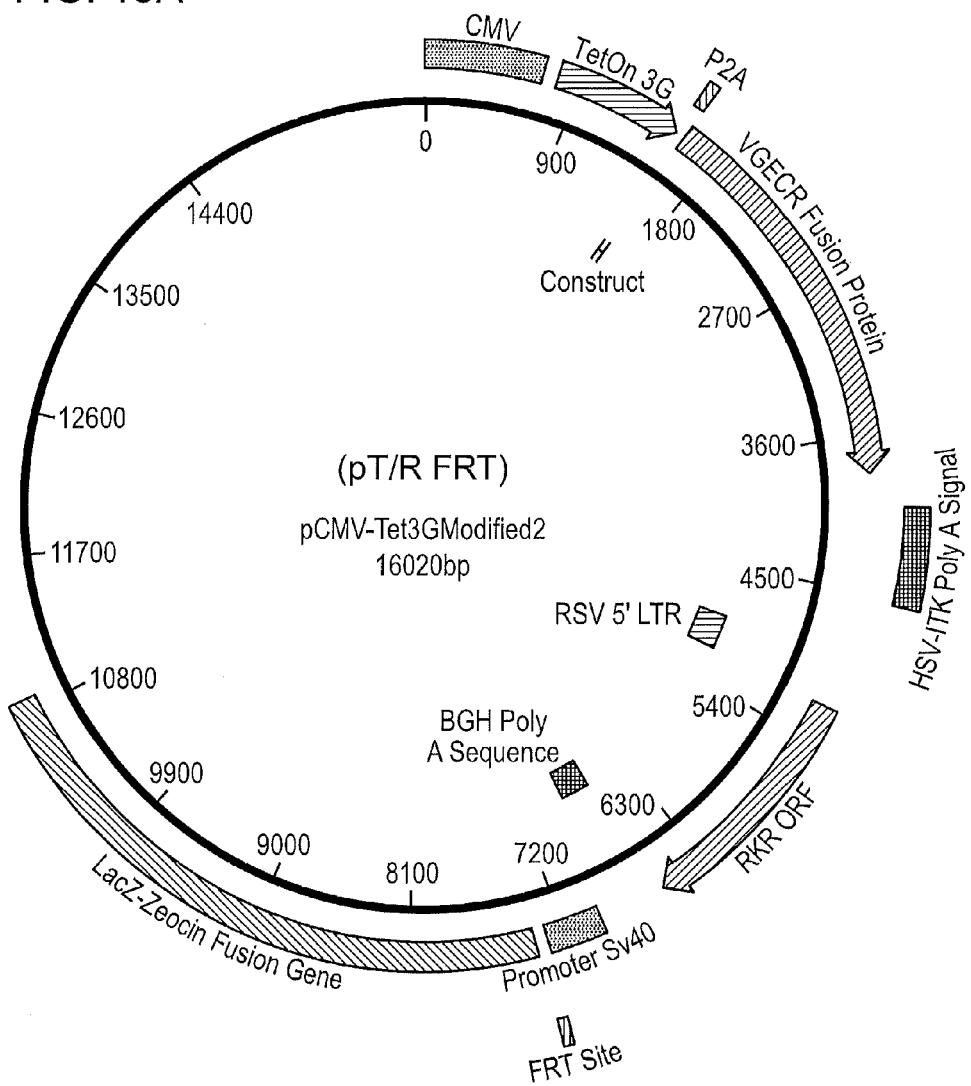
Figure 15A:
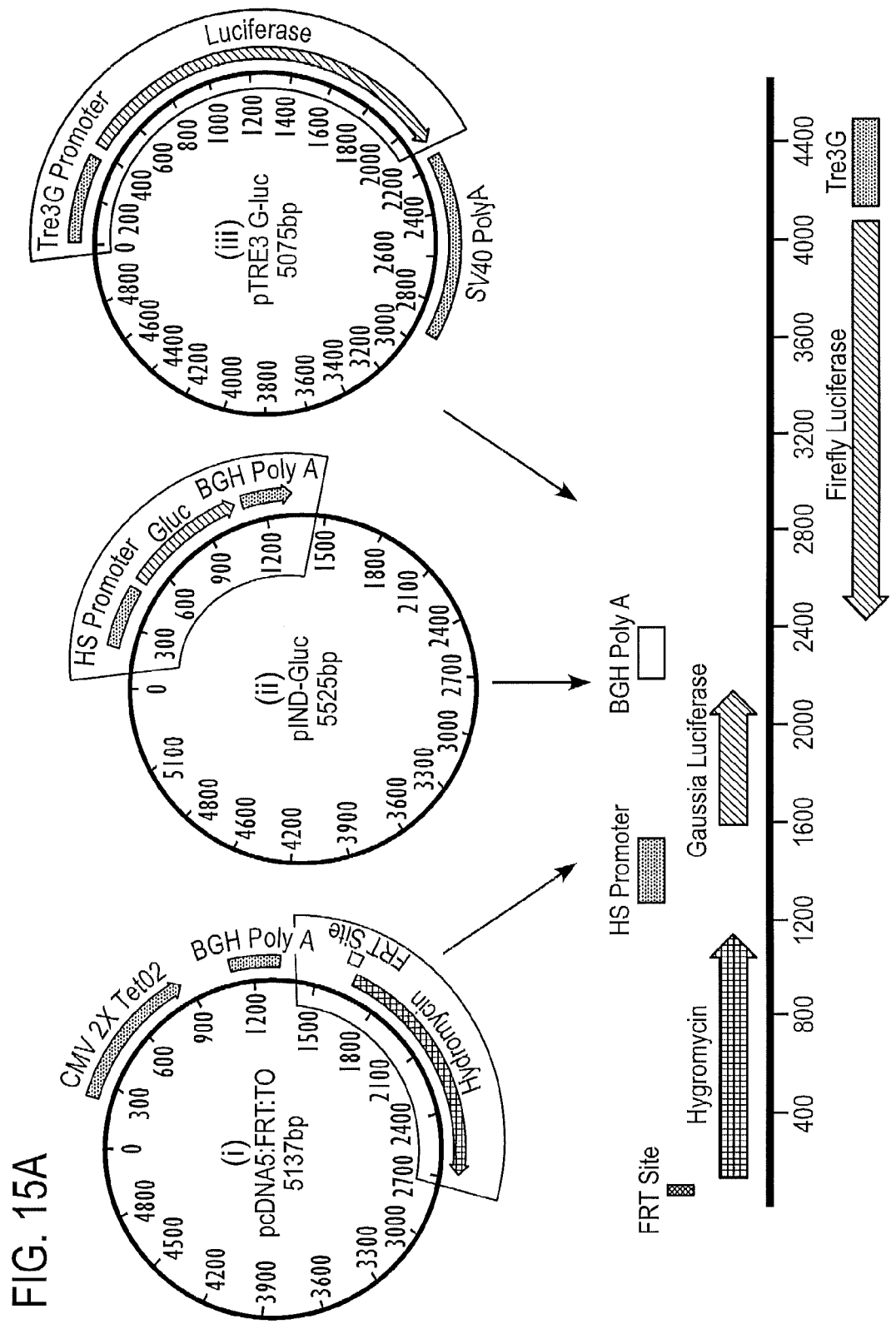

Further aspects of the invention include a method for creating a cell line that can be made to regulate the expression of any two genes placed under the respective inducible promoter comprising utilizing the vector of FIG. 13 or the vector of FIG. 15 and cells lines created from such methods.

Another aspect of the invention is a method for controlling the expression of any two genes of interest comprising utilizing the vector of FIG. 13 or the vector of FIG. 15.

Additional aspects of the invention are cells lines comprising such vectors.

To facilitate a more rapid and refined analysis of CD4 and CCR5 usage efficiencies with even greater sensitivity, a reporter Affionfile system containing a tat-rev dependent GFP-Gaussia luciferase Reporter (GGR) has been engineered. This GGR Affinofile system provides several advantages, including, (1) characterizing the phenotypic and biological consequences for envs with defined mutations that modulate CD4 or CCR5 binding, (2) revealing the phenotypically distinct CD4/CCR5 usage patterns amongst the prevalent HIV-1 subtypes (A and B vs C), and (3) uncovering that mutations conferring resistance to Broadly Neutralizing Antibodies (BNAbs) often compromises the efficiency of CD4/CCR5 usage and entry.

Analysis of mutations known to only modulate CD4 (E153G) or CCR5 (K421D, S142N) binding demonstrated that CD4 and CCR5 usage is an inter-related process, as mutations that affect CD4 binding influence the efficiency of CCR5 usage and vice versa. The relative entry efficiencies defined in GGR Affinofile system were also reflected in their entry efficiencies into primary CD4+ T cell subsets. Next, over 50 pseudotyped and uncloned HIV-1 viruses from five different subtypes were analyzed, and it was noted that subtype C envelopes could be distinguished from the other subtypes based on their greater efficiency of CD4/CCR5 usage which was reflected in their vector metrics (increased angle and mean induction). Lastly, envelopes with engineered mutations known to confer resistance to BNAbs (VRC01 and PG6/PG19), invariably resulted in a decreased CD4/CCR5 usage efficiency, but also demonstrated a subtype dependent influence on the envelope's ability to use CD4 and CCR5.

These results indicate that the GGR Affinofile system can quantify and reveal biologically relevant differences in CD4/CCR5 usage patterns in envelopes that reflect their genetic-epidemiological differences, pathogenicity, cell tropism, and even fitness cost as a result of resistant mutations to BNAbs.

BRIEF DESCRIPTION OF THE SEVERAL VIEWS OF THE DRAWINGS

This application file contains at least one drawing executed in color. Copies of this application with color drawing(s) will be provided by the Office upon request and payment of the necessary fee.

FIG. 1 depicts the generation of Gaussia-luciferase-GFP reporter (GGR) Affinofile cells.

FIG. 2 depicts the original Tat-rev dependent vector.

FIG. 3 depicts the sensitivity of GGR for detecting HIV infection.

FIG. 4 illustrates that GGR Affinofile cells give a vector metric that can quantify the efficiency of CD4 and CCR5 usage by specific HIV and SIV envelopes.

FIG. 5 shows that SIV316 is much more sensitive to changes in CCR5 levels and is relatively insensitive to varying CD4 levels.

FIG. 6 shows the reproducibility of vector metrics which describe the entry efficiencies and phenotypic characteristics of any given HIV envelope.

FIG. 7 is the proof of principle that vector metrics represent known biological phenotypes of well-characterized enveloped mutations.

FIG. 8 illustrates that GGR cells can be used to detect HIV (functional viral load) in human serum.

FIG. 9 illustrates that vector metrics from envelopes derived from different subtypes.

FIG. 10 illustrates that vector metrics derived from receptor affinity profiling can be used to differentiate envelope clones from transmitter/founder isolates and those from chronically infected isolates.

FIG. 11 identifies compounds under development to inhibit HIV fusion.

FIG. 12 illustrates the results of a sample Phenosense susceptibility test.

FIG. 13 identifies the vector TenOn3G/VgRXR-FRTLacZeo (pT/R Frt) that is the foundation of the third generation dual-inducible cell line.

FIG. 14 illustrates a confirmation that the pT/R FRT vector is functional in 293 cells.

FIG. 15 illustrates the dual inducible vector containing the FRT site.

FIG. 16 illustrates a schematic for the generation of a dual-inducible cell line.

FIG. 17 illustrates the expression of CD4 and CCR5 and the maturation of the sensitivity vectors over time.

FIG. 18 illustrates that pDual (Tre-Gaussia, IND-Firefly) exhibits simultaneous and independent induction.

FIG. 19 illustrates that CHO T/R Frt can sufficiently induce pDual (mCherry/GFP) in the presence of inducing agents.

FIG. 20 defines the parameters that impact on the infectivity metrics used for profiling the efficiency of HIV entry.

FIG. 21 shows that Affinofile metrics further illuminate the phenotype of well-characterized point mutants.

FIG. 22 shows that Affinofile metrics reflect biologically relevant differences in T cell subset tropism.

FIG. 23 illustrates that Affinofile metrics reveal differences in CD4/CCR5 usage efficiencies between Transmitter/Founder (T/F) and chronic envelopes.

FIG. 24 shows that HIV envelopes exhibit subtype-specific differences in CD4/CCR5 usage efficiencies.

FIG. 25 shows that Affinofile profiling reveals that resistance to broadly neutralizing antibodies (BNAbs) also results in reduced entry efficiency.

FIG. 26 shows that the use of raw luciferase infection data results in variable vector metrics.

FIG. 27 shows individual GGR plots for T/F and Chronic Envelopes.

FIG. 28 shows individual GGR plots for subtype envelopes.

FIG. 29 shows that GGR Affinofile cells can detect the presence of HIV in patient plasma samples.

FIG. 30 shows that GGR Affinofile cells can detect minor X4 qausispecies.

FIG. 31 shows an intrinsic resistance to an FDA approved inhibitor revealed on Affinofile cells.

FIG. 32 provides a diagram of vector pnL T/R Frt.

FIG. 33 shows the use of the ProteoTuner system as a replacement to the tet3g or ponasterone system or to add a third inducible gene to the dual vector.

FIG. 34 provides a diagram of the triple inducible vector.

DETAILED DESCRIPTION OF THE INVENTION

One aspect of the invention is a novel cell line, an HIV tat-rev dependent GFP-Gaussia luciferase Reporter cell line, known henceforth as the GGR cell line, that detects pseudotype and replication competent HIV (cloned or uncloned isolates, in cell media or human serum) in less time, and with higher sensitivity compared to what is currently available. This GGR cell line provides an improved method of characterizing the entry phenotype of HIV envelope genes, and detecting and examining primary HIV samples in the context of laboratory research, clinical trial monitoring, and medical diagnostics. Examples include, but are not limited to, determining the functional HIV viral load, responsiveness to treatment, characterization of viral co-receptor usage (testing for viral co-receptor usage, i.e., CCR5 vs CXCR4, as required prior to prescribing FDA-approved CCR5 inhibitors), and characterization of other viral or drug resistance phenotypic properties that will guide future treatments. The flexibility is built into the described diagnostic cell-based system, which is improved by third generation plasmids also described herein.

Three advantages of the GGR reporter system that can lead to research or commercial applications that are superior to currently available methods include:

(1) Ability to detect infectious phenotype without the need for PCR cloning of viral envelope and gag-pol genes. The former (PCRing up and phenotyping the viral Envs) is required for determining co-receptor tropism, a FDA-mandated test before physicians can prescribe CCR5 inhibitors (e.g., maraviroc), while the latter (PCR-ing up and phenotyping the various gag and pol genes) is a test used by physicians to guide antiretroviral therapies (protease inhibitors, reverse transcriptase inhibitors, most recently, integrase inhibitors). These phenotypic tests for co-receptor tropism and drug sensitivity are known as Trofile™ and Phenosense™, respectively, which is marketed by monogram Biosciences.

(2) Ease of read-out: virus infection induces the linked production of both GFP and secreted Gaussia luiferase in the reporter cells. GFP serves as a convenient and simple quality control for the assay, while the secreted Gaussia luciferase can be sampled using a small volume from the infected cell culture supernatant. Because the cells are not destroyed [unlike the end-point assay of the closest competitor assay on the market (Trofile or Phenosense from Monogram Biosciences) which requires cell lysis to read the firefly luciferase signal in the cell lysate], supernatant samplings can be carried out over the course of 2-4 days to enhance sensitivity, and provide an added kinetic dimension to the phenotypic characterization. As a point of comparison, the Trofile™ and Phenosense™ assay take 2-3 weeks to complete. The described GGR cell system read-out takes approximately 2-4 days. In addition, Gaussia luciferase is reportedly much brighter (normalized luminescence per unit of substrate) than firefly luciferase.

(3) Flexibility in varying both CD4 and co-receptor levels (CCR5 or CXCR4) in the GGR system. The GGR system is structured such that CD4 and CCR5 can be simultaneously and independently induced by tetracycline (or related analogs such as minocycline and doxycycline) and ponasterone, respectively. This is a critical advantage as the commercially available or publicly available tests use cell lines with over-expressed CD4 and co-receptor levels that do not represent the physiological amounts (receptor density) present in relevant cell types in vivo (e.g., T-cells and macrophages). This shortcoming of the publicly available tests may lead to inaccurate reporting of whether a virus is resistant to a particular CCR5 inhibitor.

HIV-1 affinity for CD4 and CCR5 is associated with differential pathogenicity. Therefore, a dually inducible cell line based system has been developed that quantitatively and comprehensively characterizes viral entry efficiency as a co-dependent function of CD4 and CCR5 expression levels. This receptor affinity profiling system (Affinofile) has revealed biologically relevant phenotypes in envs with differential CD4/CCR5 usage efficiencies. For example, Elite Suppressor envs have reduced efficiency of CD4/CCR5 usage compared to Chronic Progressor envs, and for vicri-viroc-resistant envelopes, the degree of resistance is a function of the level of CCR5 cell surface density.

To facilitate a more rapid and refined analysis of CD4 and CCR5 usage efficiencies with even greater sensitivity, a reporter Affionfile system has been engineered containing a tat-rev dependent GFP-Gaussia luciferase Reporter (GGR). This GGR Affinofile system, characterizes the phenotypic and biological consequences for envs with defined mutations that modulate CD4 or CCR5 binding, (2) reveals phenotypically distinct CD4/CCR5 usage patterns amongst the prevalent HIV-1 subtypes (A and B vs C), and uncovers mutations that confer resistance to Broadly Neutralizing Antibodies (BNAbs) often compromised the efficiency of CD4/CCR5 usage and entry.

Analysis of mutations known to only modulate CD4 (E153G) or CCR5 (K421D, S142N) binding demonstrated that CD4 and CCR5 usage is an inter-related process as mutations that affect CD4 binding influenced the efficiency of CCR5 usage and vice versa. The relative entry efficiencies defined in GGR Affinofile system were also reflected in their entry efficiencies into primary CD4+ T cell subsets. Over 50 pseudotyped and uncloned HIV-1 viruses from five different subtypes were analyzed, and it was noted that subtype C envelopes are distinguished from the other subtypes based on their greater efficiency of CD4/CCR5 usage, reflected in their vector metrics (increased angle and mean induction). Lastly, envelopes with engineered mutations known to confer resistance to BNAbs, VRC01 and PG6/PG19, invariably resulted in a decreased CD4/CCR5 usage efficiency, but also demonstrated a subtype dependent influence on the envelope's ability to use CD4 and CCR5.

These results suggest that the GGR Affinofile system quantifies and reveals biologically relevant differences in CD4/CCR5 usage patterns in envelopes that reflect their genetic-epidemiological differences, pathogenicity, cell tropism, and even fitness cost as a result of resistant mutations to BNAbs.

There are several HIV indicator cell lines available. However, these cell lines lack the unique combined features found in the GGR cell line. The versatility, flexibility, and scalability (to 96- and 384-well format) of the GGR cell line, make the system useful for laboratory research, clinical trial monitoring, and medical diagnostics.

Currently, all HIV indicator cell lines use the increase production of a fluorescent protein or a (firefly) luciferase protein as an indication of infection. The use of only a fluorescent protein requires the laborious preparation of the cells and examining of cells on a fluorescent detection system. Alternatively, the use of nonsecreted luciferase requires careful attention to non-trivial matters such as complete lysis of cells before assessment of luciferase activity. Moreover, GFP or firefly (or even Renilla-luciferase) luciferase detection are endpoint assays, since the cells have to be fixed or lysed to assess HIV infection.

Additionally, all indicator cell lines express the receptor (CD4) and co-receptor (CCR5) for HIV at fixed, often over-expressed supraphysiological levels. This hinders the utility of those cell lines because different HIV isolates have varying capacity to use the receptor and co-receptor found at different expression levels on various cell types in vivo.

The GGR indicator cell line is a derivative of a modified HEK 293 cell line. 293 cells are highly transfectable and permissive for HIV infection, if the right receptors are present. This makes the 293-derived GGR cell line relatively easy to manipulate for various purposes. Additionally, 293 cells lack various HIV restriction factors found in other indicator cell lines (e.g., a number of T-lymphoid cell lines express APOBEC3F/G, a known HIV restriction factor counteracted by the HIV vif gene; others express tetherin, another HIV restriction factor counteracted by the HIV vpu gene). If present, these factors would decrease the susceptible of the cell line to HIV infection and replication, especially if the vif and vpu alleles are sub-optimal or absent. In addition to 293 cells, we are also engineering the GGR system into other highly permissive cells that lack endogenous amounts of CD4 and CCR5 (or CXCR4) such as U87 cells.

The GGR indicator cell line is a derivative of the 293 Affinofile cells (for HIV receptor Affinity profiling), a cell line where the surface expression levels of the CD4 receptor and the CCR5 co-receptor can be independently and simultaneously induced and regulated by tetracycline (or minocycline or doxycycline) and ponasterone, respectively. Consequently, the GGR cell line and the Affinofile cell line are the only cell lines where the levels of CD4 and CCR5 can be regulated to express multiple distinct combinations of CD4 and CCR5. Details regarding the construction and properties of our parental 293-Affinofile cells have been published (Johnston et al., 2009), and these 293-Affinofile cells have been used by multiple labs to investigate a number of different viral phenotypes (Lassen et al., 2009; Pugach et al., 2009; Agrawal-Gamse et al., 2009; Pfaff et al., 2010; Sterjovski et al., 1010; Roche et al., 2011a, Roche et al., 2011b).

One novel aspect of the GGR system resides in combining elements from the 293-Affinofile system with our GGR reporter so that the GGR dual-inducible system can now serve as a high throughput cell-based read-out for virus infections using either live virus from patient samples (no need for PCR amplification and cloning of viral envs or gag-pol genes) or cloned env/gag-pol genes in a reporter backbone. The detection of virus infection using the parental 293 Affinofile system required pseudotyping cloned envs onto a HIV luciferase reporter backbone, or direct staining of the cells for viral antigen. Neither approach is as sensitive, high throughput, and convenient as detecting for the presence of secreted Gaussia luciferase in the GGR system. Critically, 293-Affinofile cells could not be conveniently used to detect and characterize the entry and replication phenotypes of replication-competent viruses from uncloned viral stocks or patient samples. In sum, either cloned viral genes pseudotyped or engineered into a HIV proviral reporter backbone (Env, or gag-pol, respectively), or uncloned viral isolates from patient plasma, give a signal in the described GGR cell line, as long as tat and rev (essential viral genes expressed early on in HIV infection) are present. Viruses without functional tat and rev are by definition non-infectious, and therefore not relevant to any biological assays.

The GGR indicator cell line uses a Tat and Rev-dependent reporter to drive expression of two indicator proteins, Gaussia luciferase and GFP, upon HIV infection. As shown in FIG. 1, the HIV LTR promoter, which is activated by HIV tat, drives expression of the Gaussia luciferase (G.Luc) and GFP genes, which are linked by an internal ribosome entry site (IRES) sequence. This ensures that both gene products are produced from the same piece of mRNA (G.Luc-IRES-GFP). Additionally, a Rev-response element (RRE) is placed immediately downstream of GFP. In the absence of HIV Rev, which normally binds to the RRE and mediates nuclear export of unspliced viral genomic RNA, no full-length functional G.Luc-IRES-GFP mRNA will be exported into the cytoplasm, as judiciously placed splice donor and acceptor sites (labeled as D1, A5, D4, A7 in FIG. 1) within the construct will ensure nuclear splicing and removal of the cognate G.Luc and GFP ORFs. Therefore, G.Luc and GFP expression requires the presence of both Tat and Rev, which are produced only during HIV infection. The requirement for both tat and rev to be present in order for reporter gene expression to be observed decreases the background expression from the LTR promoter: most HIV indicator cell lines rely on only tat-dependent expression (using the LTR promoter), which is leaky.

While other groups have now engineered other tat and rev dependent reporters, none have used G.Luc as a reporter, and more critically, none have engineered the dual-reporter into our dual-inducible 293-Affinofile system. Gaussia luciferase (G.Luc), a naturally secreted and highly active luciferase, is reportedly 1000-fold brighter than firefly luciferase. Detection of GFP expression, while less sensitive, is highly correlated with G.Luc expression (due to the linked expression from the IRES). GFP expression allows for convenient quality control by simple fluorescent microscopy. G.Luc provides greater sensitivity of detection (especially when it comes to examining primary patient samples), and also provides kinetic information regarding the progression of infection, as only a small amount of supernatant (e.g., 10 ul) needs to be sampled at any given time point. All other reporters are end-point assays that require fixation or lysis of cells. FIG. 3A-B, which is described in greater detail in the next section, shows that detection of HIV infection via G.Luc activity is more rapid (17-24 hours post-infection vs 72 hours when using the standard firefly luciferase pseudotyped HIV reporter viruses), more sensitive (as little as 0.0625 MOI), and as robust as compared to using the gold standard of staining for intracellular p24 antigen using the KC57 Mab (as robust, and much more efficient and economical, see below, and legend to FIG. 3B).

The GGR indicator cell line has unique properties as it was single cell cloned from a heterogeneous pool of parental 293-Affinofile cells that were transduced with the lentiviral vector carrying the tat-rev dependent G.Luc-IRES-GFP vector. Multiple single cell clones were examined in order to select the clone that provided the optimal signal:noise ratios upon HIV infection while maintaining the reproducible induction of CD4 and CCR5 expression levels of the parental 293-Affinolfile cells. (see FIG. 1C)

GGR Vector Construction pnL-Gluc-GFP-RRE was constructed by inserting gaussia luciferase into the BamHI-SphI site of pnl-GFP-RRE (NIH AIDS Research and Reference Reagent Program, Catalog #11466). Pnl-GFP-RRE was digested overnight with the enzymes BamHI and SphI. Gaussia luciferase was obtained by digesting pcmv-Gluc (Promega) with BamHI and SphI overnight. The gaussia luciferase DNA fragment and digested pnl-GFP-RRE were gel purified and subjected to ligation.

Generation of GGR Cell Line

Figure 1C:
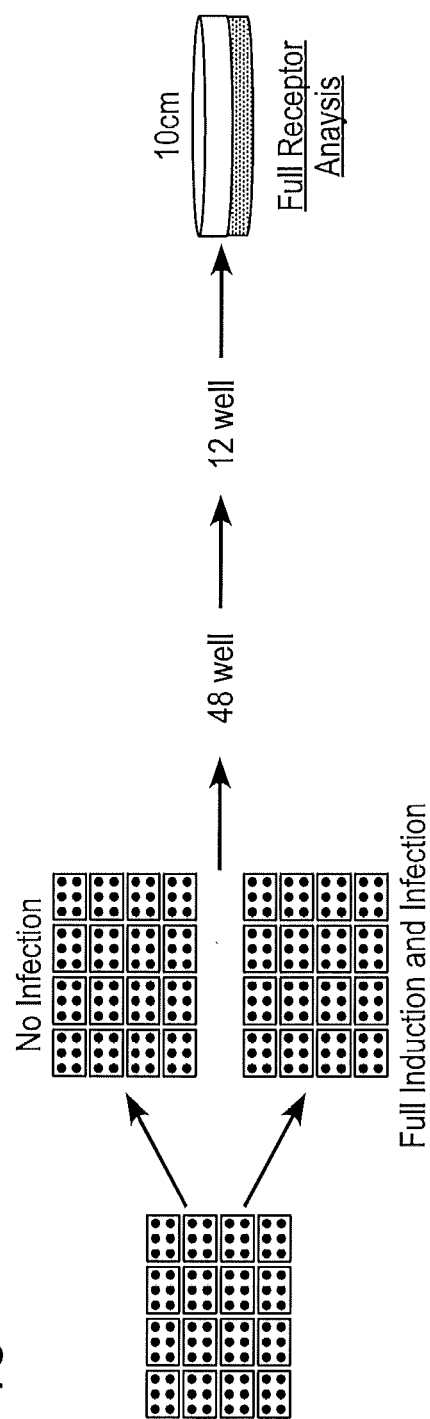
Figure 2:
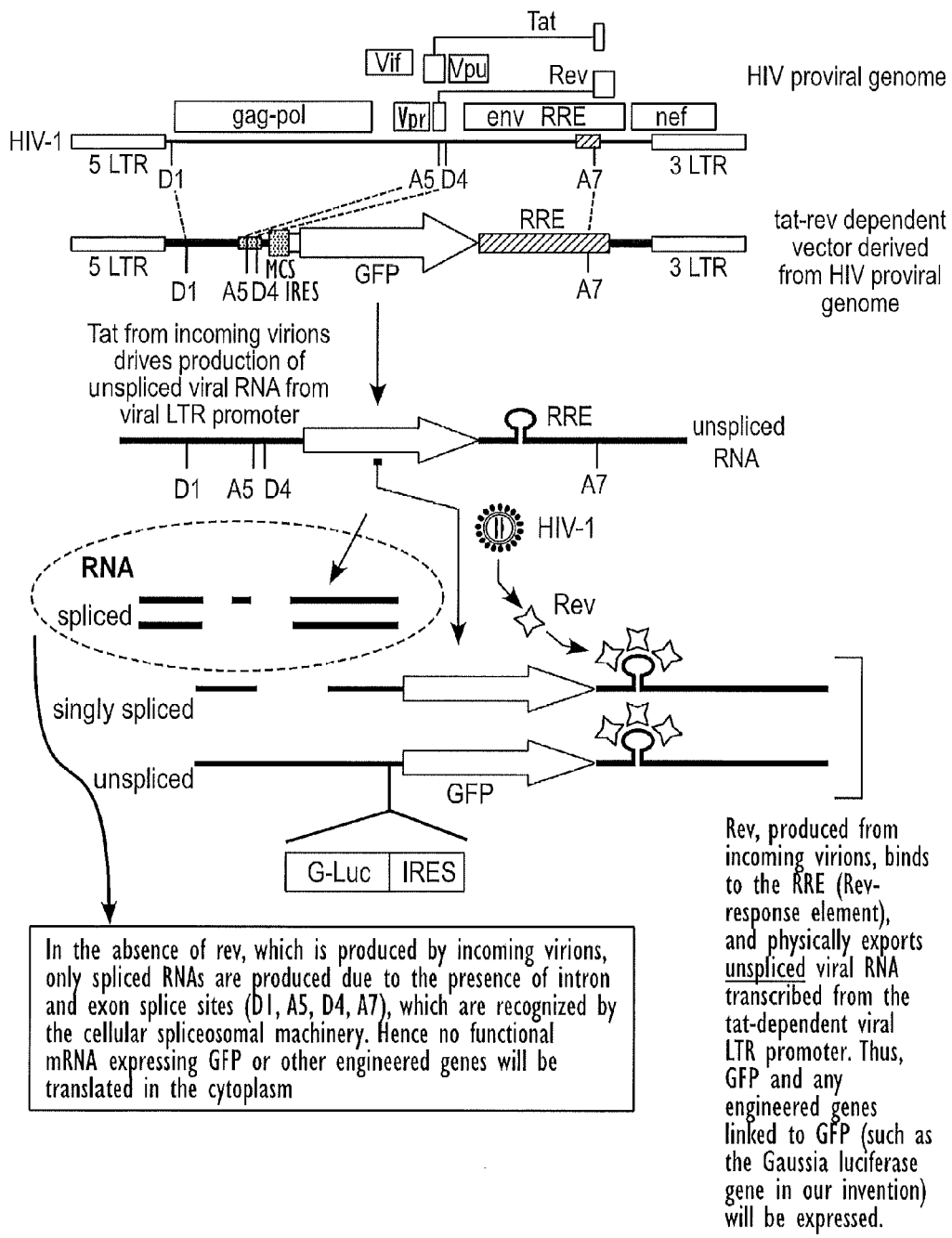

The Gaussia luciferase gene was engineered upstream of the GFP reporter (linked via an internal ribosomal entry site (IRES) sequence) in a Tat and Rev dependent vector. Judiciously placed splice donor and acceptor sites, in addition to the Rev-responsive element (RRE) placed downstream of the GFP reporter gene, ensures that only the full-length unspliced reporter mRNA will be translated in the presence of tat and rev, which is provided by commonly used HIV reporter vectors, and replication-competent HIV. The GGR vector was packaged into a VSV-G pseudotype lentivirus. This virus was subsequently used to transduce parental 293-Affinofile cells. Transduced Affinofile cells were passaged continually until basal Gaussia luciferase levels stabilized. Individual cell clones were selected based on best receptor and co receptor induction and signal to noise properties. (FIG. 1). FIG. 1(A) shows tat-Rev dependent G.Luc-IRES-GFP construct delivered to 293 Affinofile cells by lentiviral transduction (FIG. 1(B)). Cells were single cell cloned and passaged until the basal G.Luc signal was stable (FIG. 1(C)). Select clones were expanded and infected with a R5-tropic HIV upon full-induction of CD4 and CCR5. Clones with the highest signal:noise upon infection are indicated in red. One or two clones were expanded for further use. FIG. 1(A) with No HIV Infection led to minimal expression in absence of Tat; any basal expression of mRNA in absence of Rev leads to only spliced mRNA; and no reporter gene expression, whereas FIG. 1(A) with HIV Infection led to increased mRNA Transcription due to HIV Tat; unspliced mRNA transported by HIV Rev; and increased protein expression. FIG. 2 illustrates the original Tat-rev dependent vector (Wu et al., 2007) showing the HIV proviral genome at the top, the tat-rev dependent vector derived from the HIV proviral genome at the middle (the tat from incoming virions drives production of unspliced viral RNA from viral LTR promoter) at the middle and Rev, produced from incoming virions, binds to the RRE (Rev-responsive element), and physically exports unspliced viral RNA transcribed from the tat-dependent viral LTR promoter. Thus, GFP and any engineered genes linked to GFP (such as the Gaussia luciferase gene) will be expressed. In the absence of rev, which is produced by incoming virions, only spliced RNAs are produced due to the presence of intron and exon splice sites (D1, A5, D4, A7), which are recognized by the cellular spliceosomal machinery. Hence no functional mRNA expressing GFP or other engineered genes will be translated in the cytoplasm.

FIG. 3 depicts the sensitivity and specificity of GGR for detecting HIV infection. FIG. 3(A) illustrates that GGR cells were maximally induced with doxycycline (4 ng/ml) and ponasterone (4 uM) at the time of their seeding. 16-21 hours post-seeding/induction, cells were infected with a R5-tropic HIV at varying multiplicities of infection (MOI). The titer of the virus was previously determined on stable CD4/CCR5-expressing GHOST cells, a standard procedure. At 17, 24, 48, and 72 hours (bars from left to right respectively in A below), 10 ul of the infected cell supernatant was removed and analysed for gaussia luciferase activity on a luminometer as per manufacturer's instructions. The left panel in 3(A) shows the raw luciferase activity (RLU, relative light units) and the right panel shows the corresponding signal: noise ratios at data point. Even at the lowest MOI (0.0625), a signal to noise above 10 could be detected after 72 hours. At moderate MOI (0.25), a signal:noise close to 20 can be detected as early as 17 hours post-infection. In FIG. 3(B), an identical experiment was performed except that CD4/CCR5 was induced at low, medium or high levels. 3 days post-infection, supernatants were collected and analyzed for G.Luc activity while cells from each well were individually processed for intracellular staining for viral antigen (p24) using PE-conjugated Mab against p24. Parenthetically, the only p24 antibody that consistently works for intracellular p24 staining is the KC57 clone from BD, which costs ~$450 for 100 tests. The Gaussia luciferase substrate costs ~$200 for about 1,000 tests.

Figure 4A:
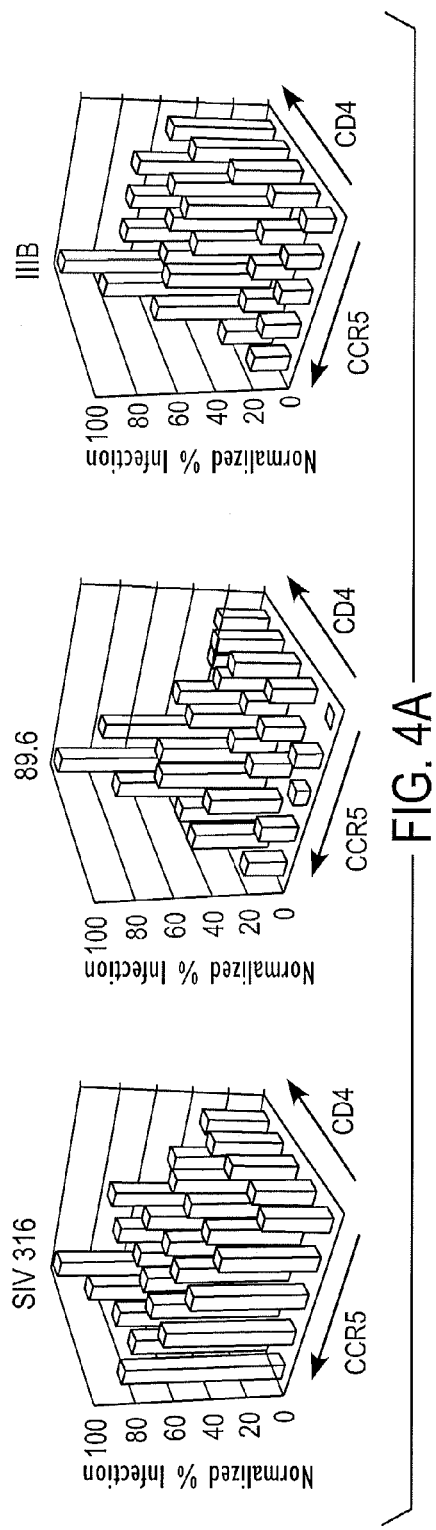

FIG. 4 shows that GGR cells were induced to express 25 distinct combinations of CD4 and CCR5 expression levels by varying concentrations of doxycycline and ponasterone. Experiments were performed in a 96-well format, each combination infected in triplicates. Equivalent amounts of 3 pseudotyped viruses (SIV316, HIV 89.6 and IIIB) ("CD4-independent isolate," "primary HIV-1 dual-tropic (R5×4) isolate," and "HIV-1 T-tropic (X4) isolate," respectively) were used to infect GGR cells expressing each distinct combination of CD4/CCR5 expression levels in triplicates. FIG. 4(A) depicts the 3-D data plot showing the varying infectivity profile for the viruses examined, which could be regressed to a 3-D surface plot in 3(B) using a mathematical function described in Johnson et al., 2009. (3(B), middle panel). Each surface plot has a vector (blue arrow) that can be represented by three metrics: the vector angle (red, ⊖; magnitude or slope of the vector, represented by the gradient of the blue arrow on the surface plot; and the mean induction (average height of the surface plot, represented by the height of the doted green box, or M).

Figure 4B:
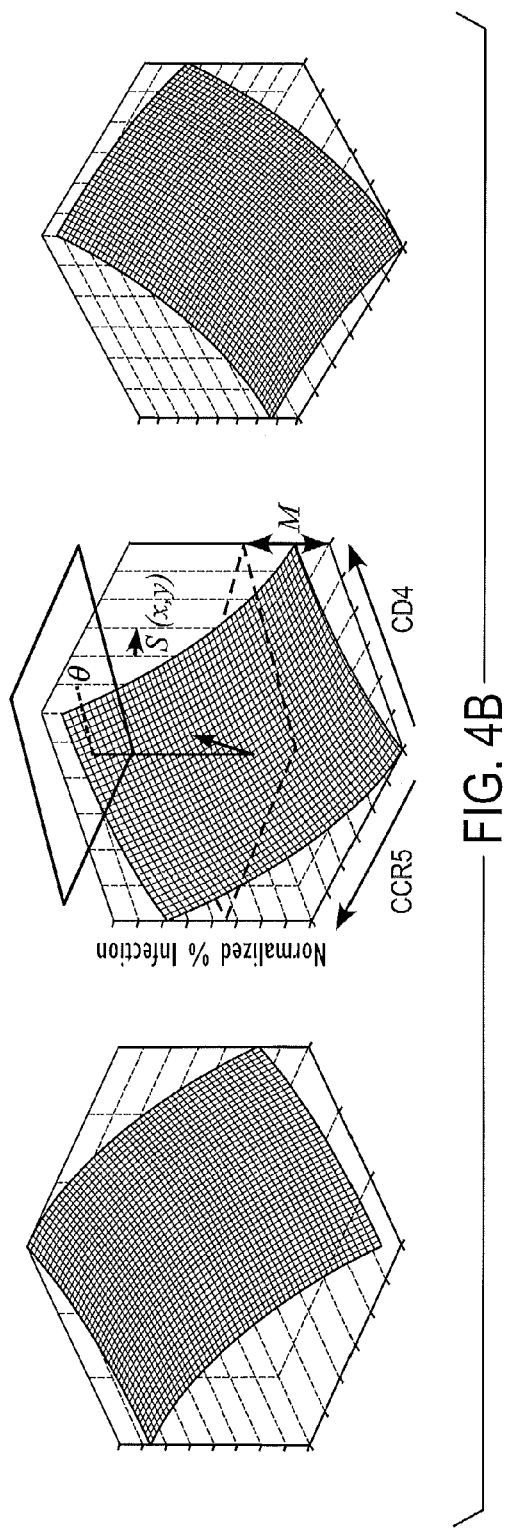
Figure 5:
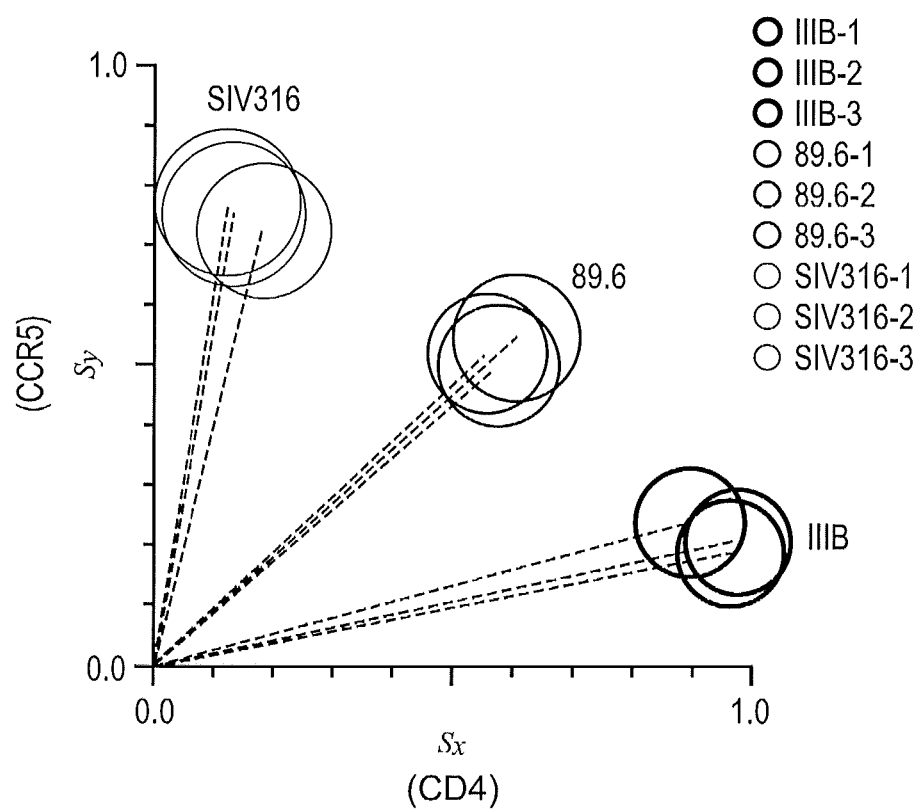
Figure 6A:
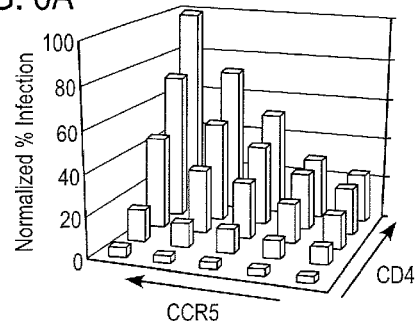
Figure 6B:
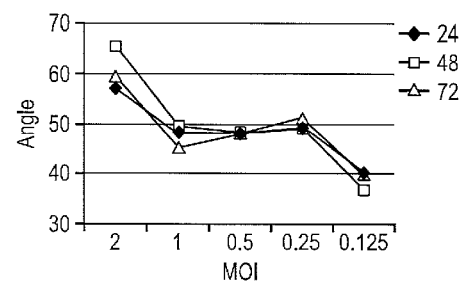
Figure 6C:
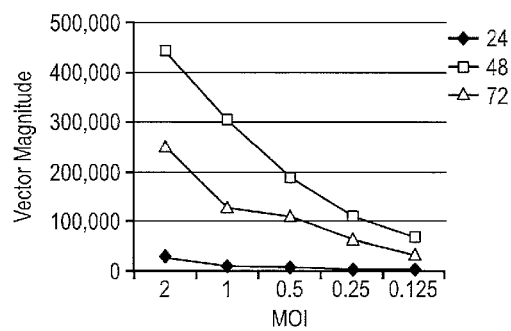
Figure 6D:
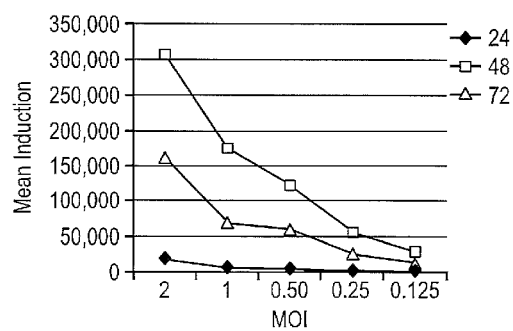
Figure 6E:
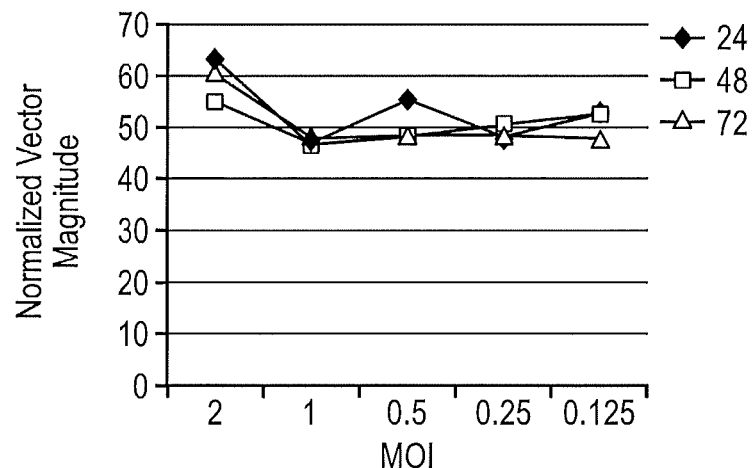
Figure 6F:
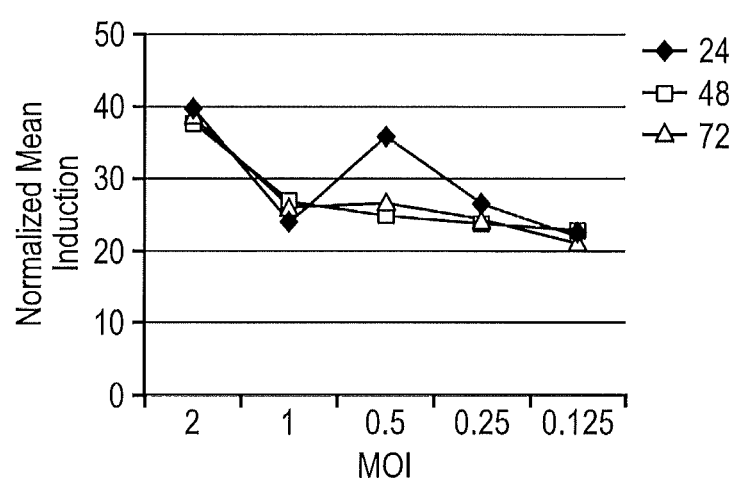

FIG. 5 shows a polar plot representing the three metrics described in FIG. 4(B). SIV316 has a vector angle closest to 90 degrees which indicates that it is much more sensitive to changes in CCR5 levels and is relatively insensitive to varying CD4 levels. This one metric clearly describes the raw data pattern seen in FIG. 4(A). Conversely, HIV IIIB has a vector angle closest to zero degrees, which indicates the reverse phenotype from SIV316. This phenotype can be attributed to the use of low levels of CXCR4 present on the HEK293 cells, the parental derivative of GGGR Affinofile cells. Again, inspection of the raw data in FIG. 4(A) demonstrates the veracity of this metric. Finally, 89.6 has a vector angle of ~45 degrees indicating that it is equally sensitive (dependent) on changes in CD4 and CCR5 levels.

FIG. 6 shows the reproducibility of vector metrics which describes the entry efficiencies and phenotypic characteristics of any given HIV envelope. FIG. 6(A) is the raw infectivity data is shown for a prototypical CCR5-using HIV-1 envelope (BaL) across 25 distinct combinations of CD4 and CCR5 expression levels. The raw data is then mathematically deconvolved as described in FIG. 4 in order to give the three vector metrics: FIG. 6(B) Vector Angle, FIGS. 6(C and E) Vector Magnitude (or gradient/slope), and FIGS. 6(D and F) Mean Induction. For the Vector Angle in FIG. 6(B), the data obtained at 24, 48 and 72 hours remained relatively constant (~50 degrees) when the viral inoculum was in the linear range between MOI of 0.25 to 1 (MOI=Multiplicity of Infection). Vector Angle of ~50 degrees indicates that the viral infectivity mediated by the BaL envelope is almost equally sensitive to changes in both CD4 and CCR5. FIG. 6(C) show that the vector magnitude, also known as the slope of the 3-D surface plot, as well as the Mean Induction (FIG. 6(D)), can vary markedly as a function of MOI or time post-infection if raw (luciferase) values were used for the calculation. FIGS. 6(E and F) However, when the normalized values were used for each data point, the normalized vector magnitude FIG. 6(E) or mean induction FIG. 6(F) are more robust. Values are normalized at each data point (time post-infection and MOD by setting the luciferase value obtained at the highest CD4/CCR5 induction level at 100%.

Figure 7D:
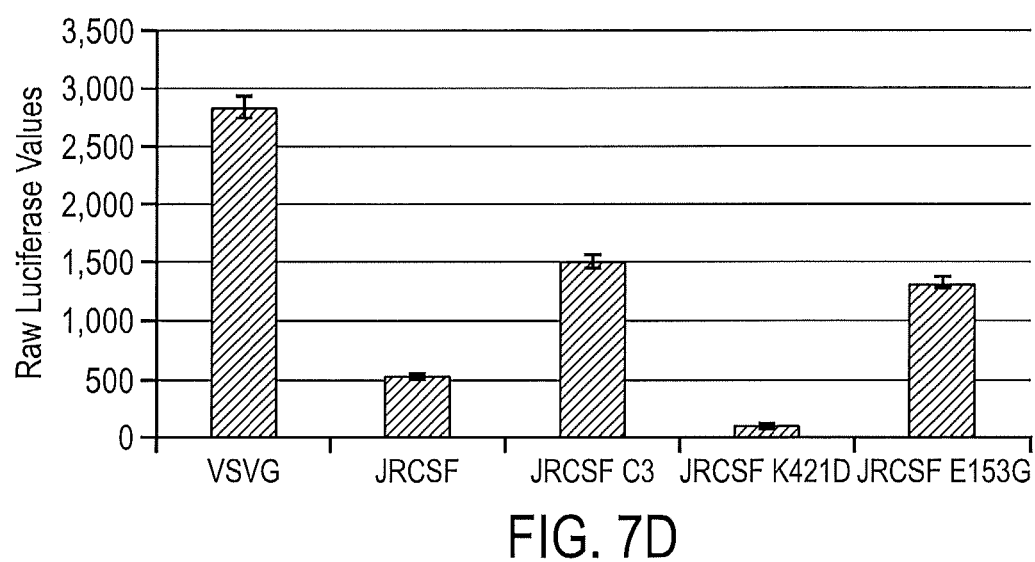

FIG. 7 is the proof of principle that vector metrics represent known biological phenotypes of well-characterized enveloped mutations. FIG. 7(A) is the infectivity profile of wild-type CCR5-using JRCSF envelope in comparison with three individual point mutants (E153G, K421D, and S142N) previously shown to modulate CD4 and/or CCR5 usage. FIG. 7(B) is a polar plot representing the vector metrics obtained from mathematical analysis of the infectivity profile in FIG. 7(A). The vector angle is bounded by the x-axis and the dotted line (e.g. the angle of the blue dotted line (K421D mutant) is less than the angle of orange (E153G) and brown (S142N) dotted lines). The vector magnitude or slope is represented by the length of the dotted line (e.g. the K421D mutant (blue dotted line) has the largest vector magnitude or steepest slope. The Mean Induction is represented by the size of the circle (e.g. S142N (green circle) has the highest mean induction, while K421D (blue circle) has the lowest). FIG. 7(C) is a summary of infectivity profile observed from data in FIGS. 7(A and B). FIG. 7(D) shows the efficiency of entry determined by the infectivity profile in GGR cells corresponds to their efficiency of entry in primary CD4+ T-cells. This indicates that the vector metrics obtained from receptor affinity profiling using GGR cells have predictive value in terms of their efficiency of entry in relevant primary CD4+ T-cells.

Figure 8:
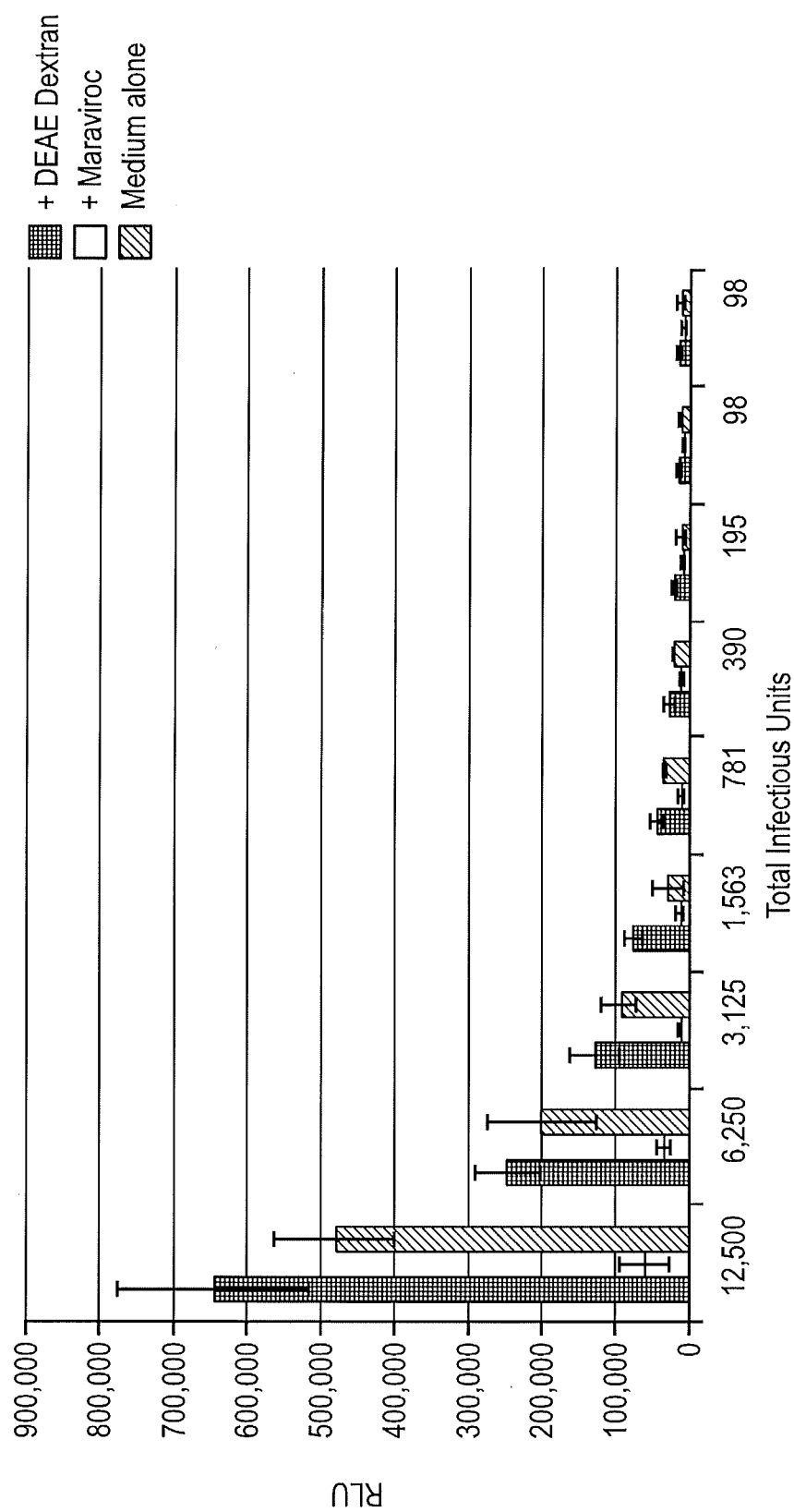

FIG. 8 shows that GGR cells can be used to detect HIV (functional viral load) in human serum. A protypical CCR5-using HIV-1 isolate (live, replication-competent JR-CSF) was pre-titered on R5-GHOST cells (a standard procedure). The indicated amount of infectious units was spiked into an equal volume of HIV-negative human plasma, which was then transferred onto GGR cells in 96-well plates that were maximally induced for CD4 and CCR5 expression. 48 hours post-infection, 10 ul of the supernatant was collected and analyzed for Gaussia luciferase activity using standard substrates and luminometry. Viral infection was performed in the presence of (1) DEAE-dextran, a commonly used poly-cationic reagent to enhance viral infection (dark grey, $1^{st}$ bar), (2) Maraviroc, a FDA approved CCR5 inhibitor (light grey, 2nd bar), and (3) Culture Medium alone (medium grey, 3rd bar). Specific CCR5-mediated infection (i.e. signal could still be reproducibly reduced by maraviroc) could be measured at viral inoculum as low as 390-781 I.U. This demonstrates the utility of measuring the functional viral load in the serum samples from HIV+ patients. In addition, the ability of infection to be inhibitable by maraviroc confirms the R5-tropism of the virus tested. If the virus was CXCR4-using, infectivity would not be affected by maraviroc. GGR cells express low endogenous amounts of CXCR4, but sufficient to give a robust G.Luc signal with X4-tropic viruses that is resistant to maraviroc inhibition. This functional property has the potential to characterize the relative amounts of X4 vs R5 viruses present in HIV+ patient's serum. Currently, the TROFILE™ test offered by Monogram Biosciences is the only commercial test that performs this assay, which is required by the FDA before prescribing CCR5-inhibitor therapy.

Figure 9:
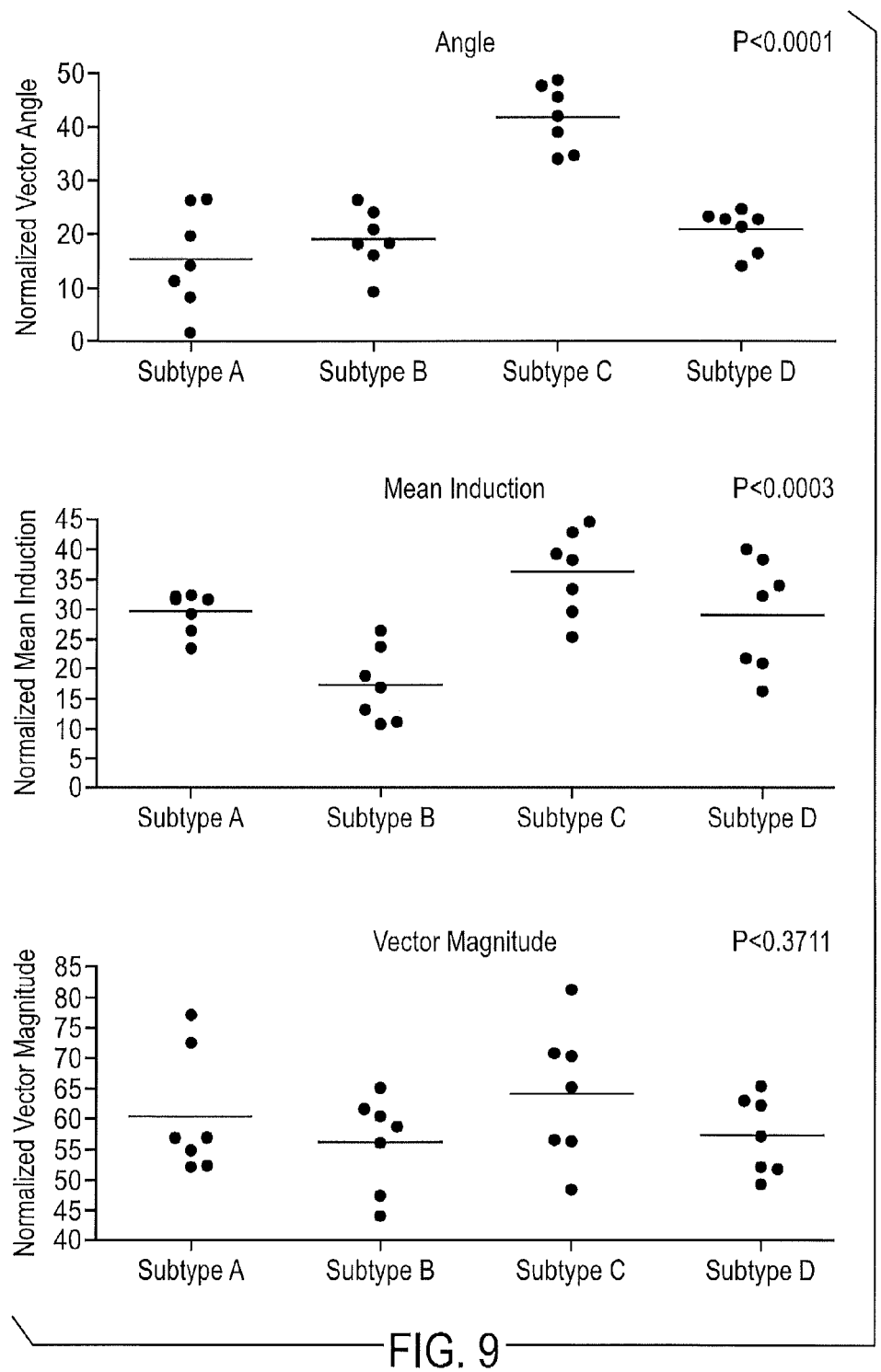

FIG. 9 illustrates Vector Metrics from Envelopes derived from different Subtypes. Sensitivity vector analysis reveals CD4 and CCR5 usage differences between envelopes derived from Subtype A, B, C and D envelopes from chronically infected patients. Normalized infection data from Subtype A, B, C and D envelope clones were analyzed by the VERSA program (Viral Entry Receptor Sensitivity Assay) formulated by Dr. Tom Chou. (see Johnston et al., 2009). The vector metrics were averaged for at least two independent infections (with a variance below 5%) for each envelope in each subtype group (n=28). The median value of the vector angles, normalized mean induction, and normalized vector magnitude are shown. P values were generated by one-way ANOVA. This demonstrates that GGR analysis of entry efficiency profiles have the potential to differentiate HIV subtypes found across the world. While the vector metrics may seem to have a large spread between viral envelope clones within each sub-type, significant differences can still be found when comparing envelope clones across subtypes. Subtype C appears to differentiate itself best from the other subtypes. Collective data such as these may be important for monitoring virus evolution during vaccine or anti-retroviral therapeutic trials.

FIG. 10 illustrates that vector metrics derived from receptor affinity profiling can be used to differentiate envelope clones from transmitter/founder isolates and those from chronically infected isolates. There is surge of current interest in characterizing the phenotypic properties of transmitted/founder envelope clones. More than 80% of infections arise from a single founder virus that diversifies after establishing an initial primary infection. Many envelopes from these transmitted/founder isolates (usually from within the first 2-4 weeks of acute virus infection before seroconversion) have been cloned, curated and deposited in the NIH AIDS Reagent Repository. Vector metrics derived from receptor affinity profiling of these T/F envelope clones clearly show that they have a lower vector angle coupled with a higher vector magnitude when compared to envelope clones from chronic progressors. This suggest that the infectivity of the T/F envelopes respond more steeply to changes in CD4 levels—implying that it requires a greater level of CD4 for efficient infection. This behavior is consistent with indirect and less quantitative data from the literature.

Figure 11:
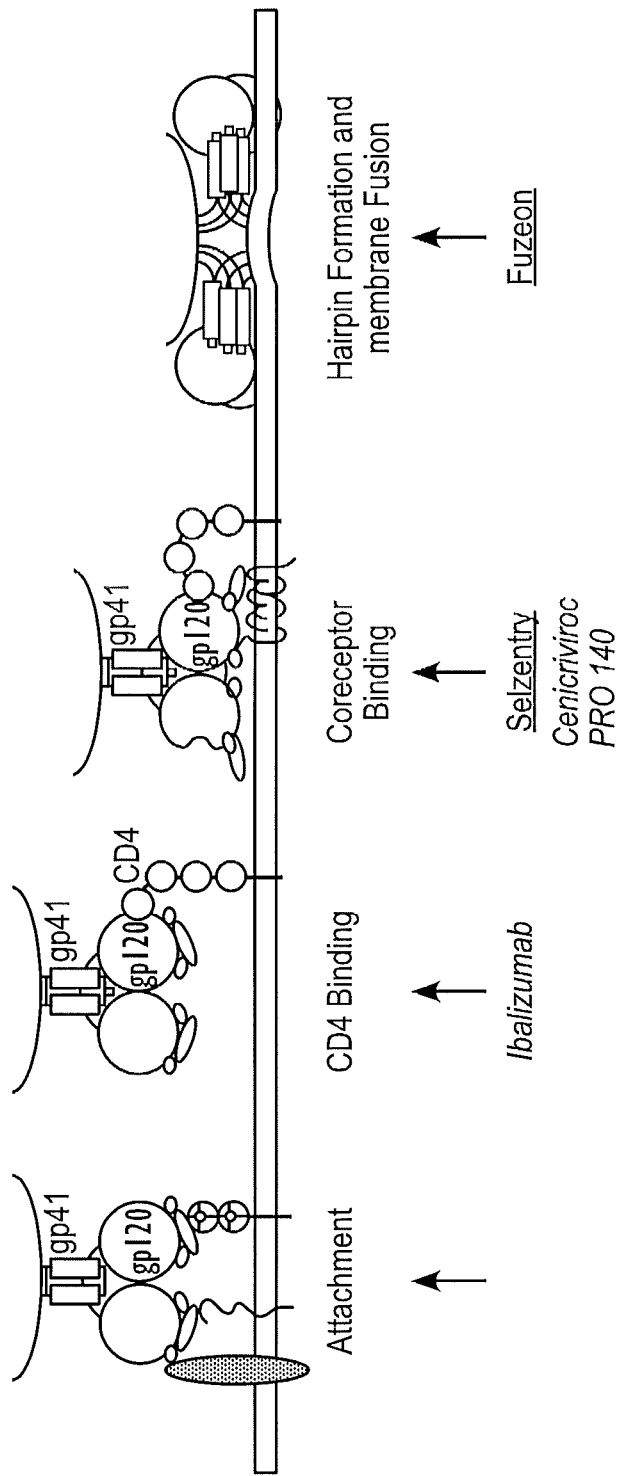

FIG. 11 is a diagram that illustrates at what step the FDA approved inhibitors and inhibitors in ongoing clinical trials would act. FDA approved inhibitors include: FUZEON (T-20): Gp41/Fusion Inhibitor; and SELZENTRY (MARAVIROC): CCR5 Inhibitor. Inhibitors currently in clinical trials include: CENICRIVIROC (TAK-652): CCR5 Inhibitor; IBALIZUMAB (TNX-355): Monoclonal CD4 antibody; and PRO 140: Monoclonal CCR5 antibody.

Figure 12A:
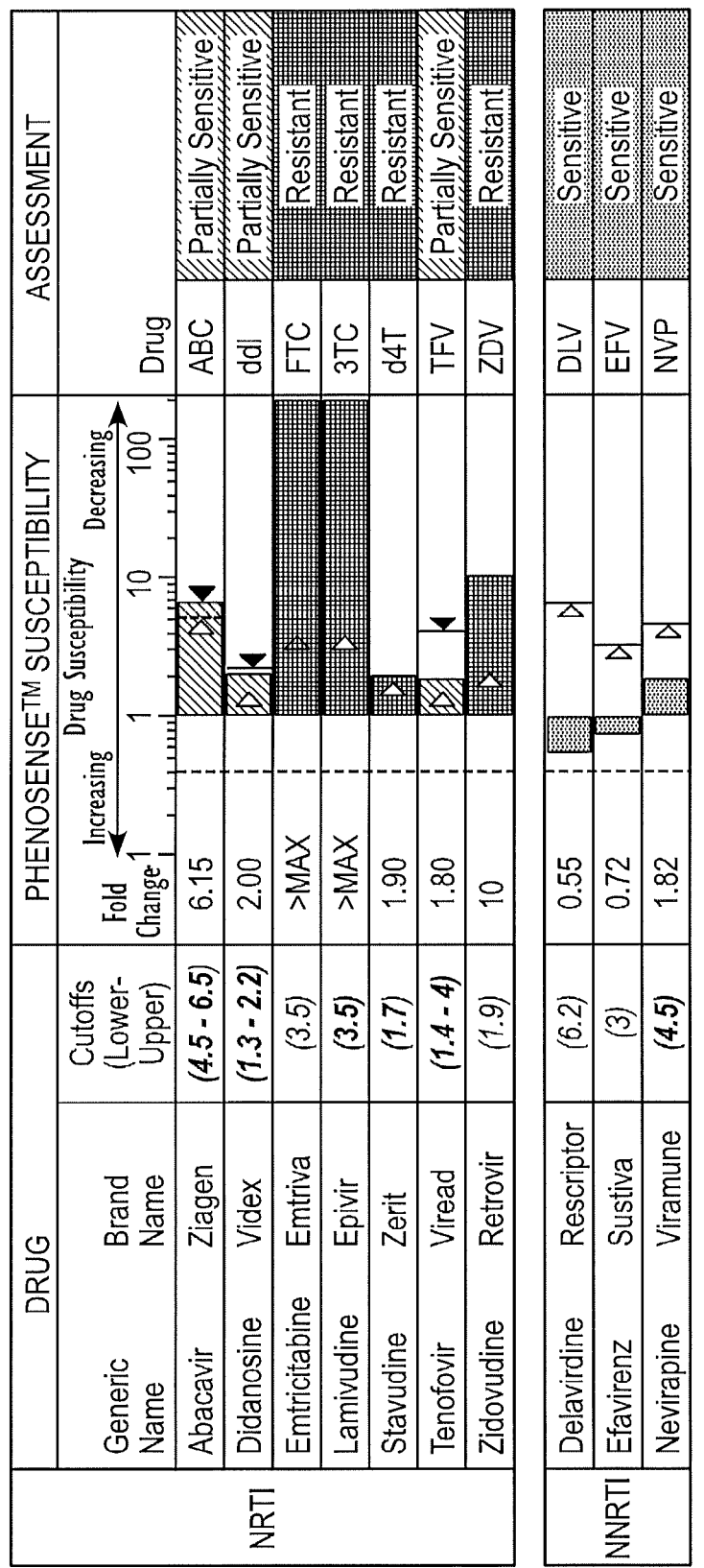
Figure 12B:
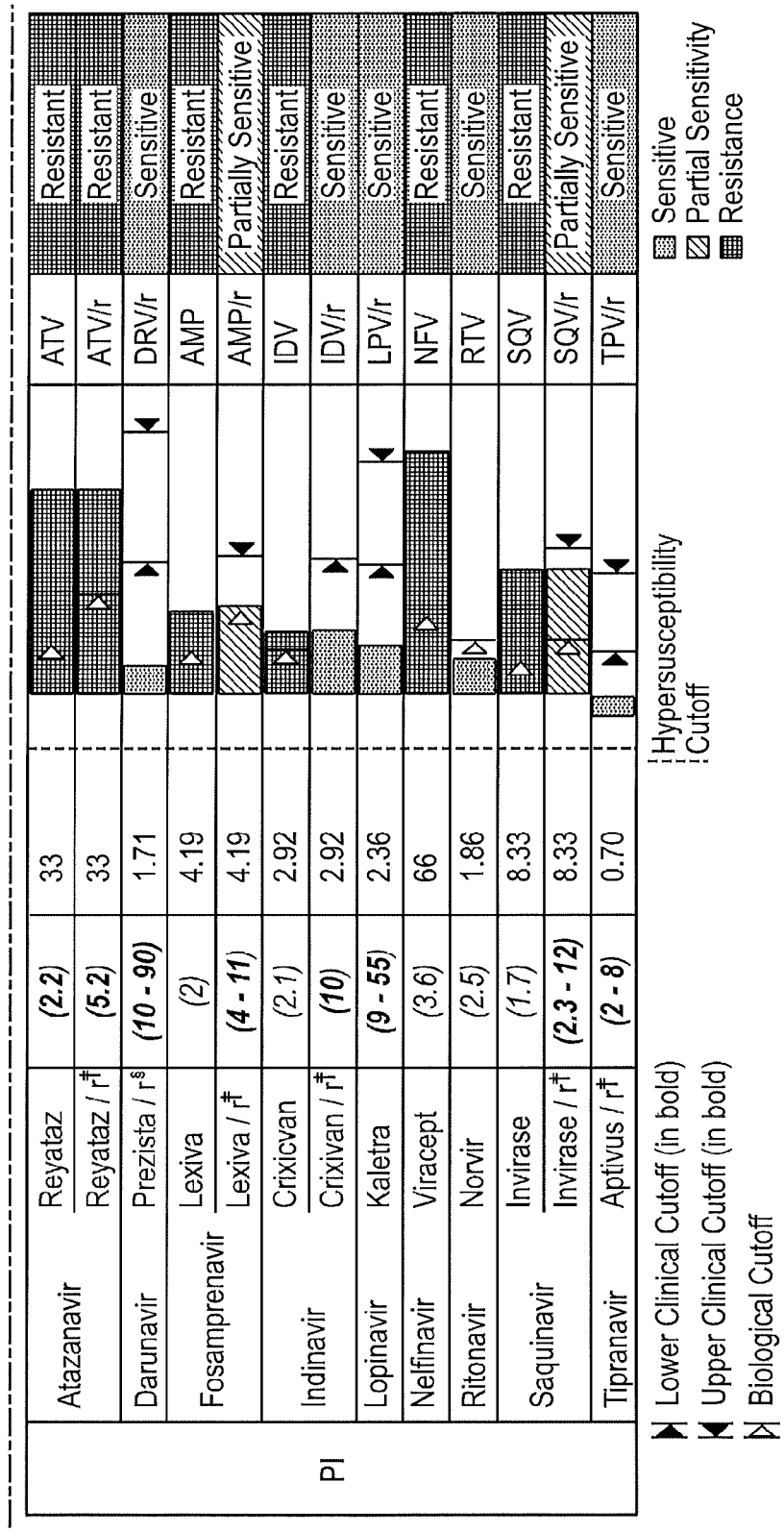

Additional HIV Inhibitors can also be used with GGR cells. The GGR cells can also be used to generate PHENOSENSE™ data (Monogram Biosciences) by testing for drug resistance of virus directly from the plasma of patients. Sample PHENOSENSE susceptibility test results are presented in FIG. 12. Patient plasma will be incubated with varying concentrations of the indicated drug and IC50 values given. Various regents have been shown to enhance HIV infection. These reagents work by promoting the interaction between the virus particle and the cell and include: DEAE Dextran; Polybrene; Protamine sulfate; Fibronectin; and CD44 Beads (Miltenyi). It is unclear, at present, whether the sensitivity will be greater than the PHENOSENSE data, but it will certainly be faster as it does not require cloning and pseudotyping of the gag-pol genes from the virus. Additional HIV inhibitors that can be used with the GGR cells are listed in Table 1.

TABLE 1

Additional HIV Inhibitors that can also be used with GGR cells.

|  | Generic Name | Brand Name |
| --- | --- | --- |
| Nucleoside Reverse Transcription Inhibitor | Abacavir | ZIAGEN |
|  | Didanosine | VIDEX |
|  | Emtricitabine | EMBIVA |
|  | Lamivudine | EPIVIR |
|  | Stavudine | ZERIT |
|  | Tenofovir | VIREAD |
|  | Zidovudine | RETROVIR |
| Non-nucleoside Reverse Transcription Inhibitor | Delavirdine | RESCRIPTOR |
|  | Efavirenz | SUSTIVA |
|  | Nevirapine | VIRAMUNE |

TABLE 1-continued

Additional HIV Inhibitors that can also be used with GGR cells.

|  | Generic Name | Brand Name |
|---|---|---|
| Protease Inhibitor | Atazanavir | REYATAZ |
|  | Darunavir | PREZISTA |
|  | Fosamprenavir | LEXIVA |
|  | Indinavir | CRIXIVAN |
|  | Lopinavir | KALETRA |
|  | Nelfinavir | VIRACEPT |
|  | Ritonavir | NORVIR |
|  | Saquinavir | INVIRASE |
|  | Tipranavir | APTIVUS |

FIG. 13 is the TetOn3G/VgRXR-FRTLacZeo (pT/R Frt) and is the foundation of the next generation dual-inducible cell line. This vector combines unique features found in different plasmids: (1) it contains the transactivators of the tetracycline (TetOn3G) and ponasterone (VgRXR) inducible systems, thereby allowing the inducible expression of two genes of interest (GOIs) from one transactivator plasmid, and (2) it incorporates the FRT-LacZeo selection cassette that allows for screening of cell clones that have integrated into a favorable chromosomal location that allows for high expression of the selectable markers (LacZ and Zeocin). By definition, once a cell clone has been selected (Zeocin resistance and beta-gal (LacZ) expression) it also implies that the two transactivators are expressed well at that chromosomal site. The FRT site (in front of the SV40 promoter that drives the LacZ-Zeocin fusion gene) allows for Flp recombinase mediated insertion of any gene construct that is also preceded by the FRT site (see FIGS. 15 and 16). Using the traditional method to make cell lines with the two transactivators stably integrated into a stable and favorable chromosomal location would have taken several independent single cell cloning steps: (1) Make the stable LacZ-Zeocin "Flip-in" cell line, and (2) Flip-in the transactivators singly or in combination. In addition, one would still have to generate stable integrants of the two GOIs under the tet-inducible or ponasterone inducible promoters, which would require two additional single cell cloning steps. Theoretically, it would take about two years to make a quadruple stable cell line expressing the two transactivators and the two inducible GOIs. Practically, it took almost 6-8 years to make the functional 293-Affinofile cells that is described in Johnston et al., 2009, that is now used by multiple labs. And the 293-Affinofile cells didn't even make use of the Flip-in system.

The pT/R Frt vector (FIG. 13) combined with the pFRT-dual vector (see FIG. 15) allows for the creation of a dual-inducible cell line in about 3 months. Generation and characterization of the parental dual-transactivator Flip-in cell line takes about 2 months. Once this is created, any two GOIs under the tet or ponasterone inducible promoters in the FRT-dual vector can be generated in about 2 weeks using Flp mediated recombination with no further need for single cell subcloning.

Figure 32:
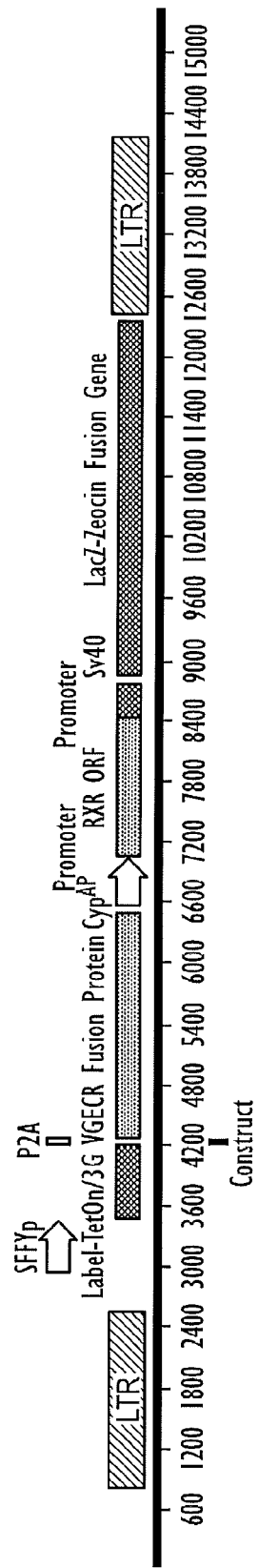

The contents of the pT/R Frt vector (FIG. 13) can be placed into a lentiviral vector for easier introduction of the transactivator and Frt site into hard-to-transfect cells, e.g., human embryonic stem cells. The vector shown in FIG. 32 is known as pnL T/R Frt.

The features of FIG. 13 are TetOn3G: is the transactivator of an improved tetracycline-on inducible system created by CLONETECH. This tetracycline-on transactivator provides tighter control and less background production of the gene of interest compared to other tetracycline inducible systems. P2A: this 19aa (57 bp) "ribosome skipping" sequence permits the production of two separate proteins from one mRNA transcript. VgECR and RXR: The proteins from these two genes act in concert as the transactivator for the ponasterone inducible system. VgECR is linked to TetOn3G expression by the P2A sequence and is driven off the CMV promoter while RXR is expressed off the RSV 5'LTR promoter. FRT: Is a 47 bp sequence that is recognized by the Flip recombinase. Flip Recombinase catalyzes the site specific recombination between two frt sites which can lead to deletion or insertion of any construct of interest. LacZeo: This gene is the fusion of two separate proteins: LacZ and Zeocin. LacZ encodes the β-galactosidase protein which catalyzes the conversion of β-D-galactoside to D-galactose. The degree of conversion can be measured by absorbance at 420 nm of the reaction mixture. Thus cells with higher absorbance at 420 nm have integrated the plasmid into a location in the genome that supports high expression of β-galactosidase and subsequently any gene inserted into that location. The zeocin cassette confers resistance to the cell that has integrated the plasmid into its genome.

Figure 33A:
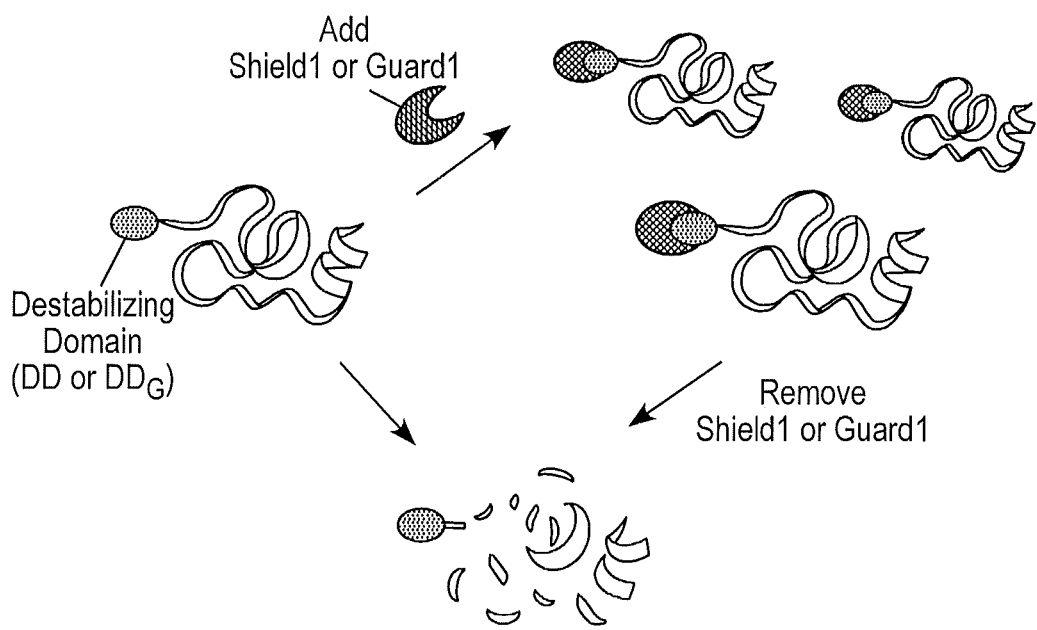
Figure 33B:
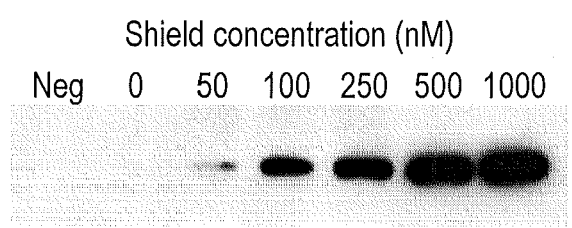
Figure 34:
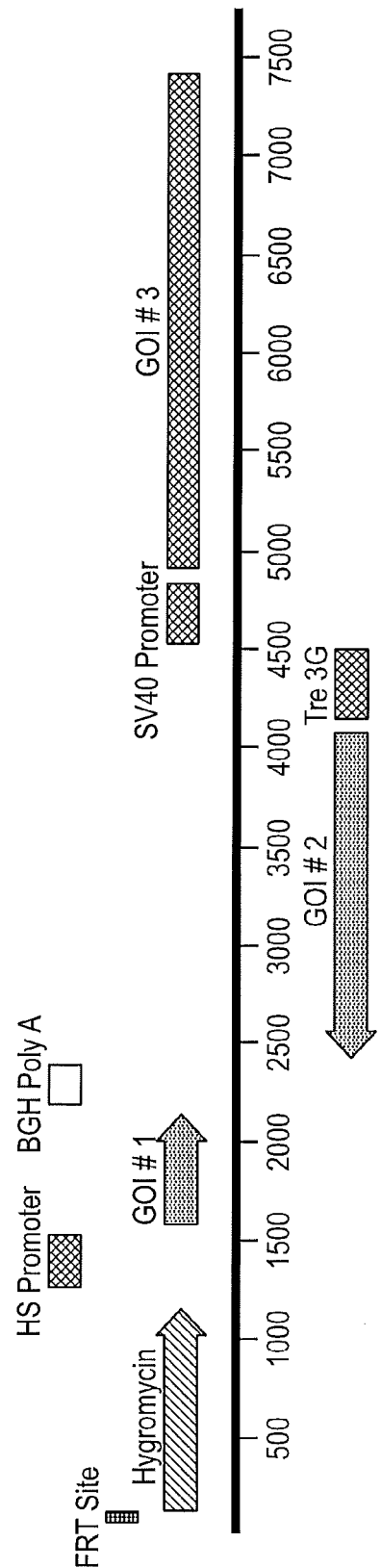

The ProteoTuner system (Clonetech) can be used as a replacement of the tet3g or ponasterone system or to add a third inducible gene to the pDual vector. FIG. 33a reflects ligand-dependent, targeted, and reversible protein stabilization. A small destabilization domain (DD, in blue) is fused to a target protein of interest. The small membrane-permeable ligand (red) binds to the DD and protects it from proteasomal degradation. Removal of the ligand, however, causes rapid degradation of the entire fusion protein. Proteins expressed using these systems are stabilized with Shield1 and Guard1, respectively. The default pathway for the ProteoTuner systems is degradation of the fusion protein, unless Shield1 or Guard1 is present. FIG. 33b reflects that protein expression can be modulated by the concentration of Shield1 present. Increasing the concentration of Shield 1 corresponds to increased stabilization of protein, thus more protein present, detected by western blot. FIG. 34 provides a diagram of a triple inducible vector.

Figure 14A:
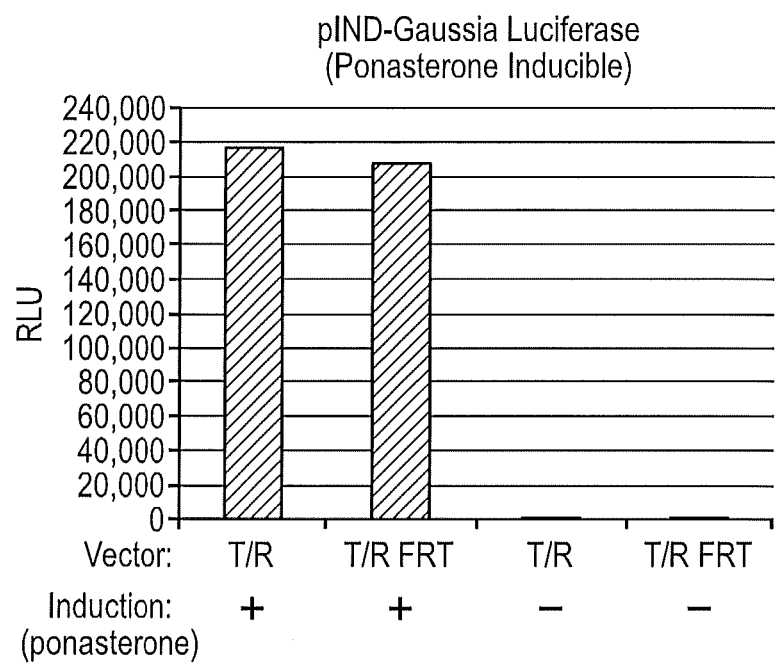
Figure 14B:
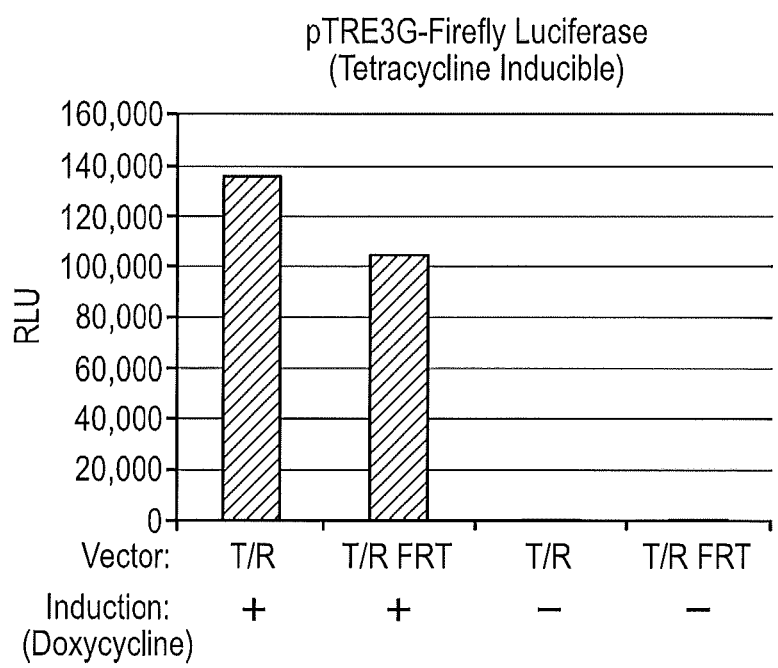

FIG. 14 shows the test of the TetOn3G/VgRXR-FrtLacZeo(T/R Frt). To test if the pT/R FRT vector is functional, 293 cells were co-transfected with the T/R FRT vector previously described in FIG. 13, along with either pIND-Gluc (Gaussia luciferase under control of the ponasterone-inducible promoter) (FIG. 14(A)), or pTRE3G.Luc (firefly luciferase under control of the 3rd generation Tetracycline-inducible promoter (FIG. 14(B)). The constructs for pIND-Gluc and pTRE3G.Luc are made from commercially available vectors and are indicated in FIG. 15. The pT/R FRT vector without the FRT-LacZeo cassette has also been created and was simply called pT/R. The pT/R vector was a control to determine if addition of this FRT cassette had any inadvertent effects on the expression of the dual transactivators. FIGS. 14 (A and B) show that it does NOT. FIGS. 14(A and B) also show that the transactivators are functional and non-leaky. That is, there is no detectable transactivation of the reporter genes in the absence of ponasterone (for Gaussia luciferase) or tetracycline (for firefly luciferase).

FIG. 15 shows the dual inducible vector containing the FRT site (pFRT—dual mentioned in FIG. 13) that can be engineered. Components of three different vectors (outlined in red) can be engineered into one vector. Note that the "FRT-hygromycin" component from vector (i) has already been successfully engineered into the pT/R FRT vector described in FIG. 13, and has no deleterious effect on transactivator expression (FIG. 14). The salient components of the pFRT-dual vector include: Gaussia Luciferase (GOI

Figure 15B:
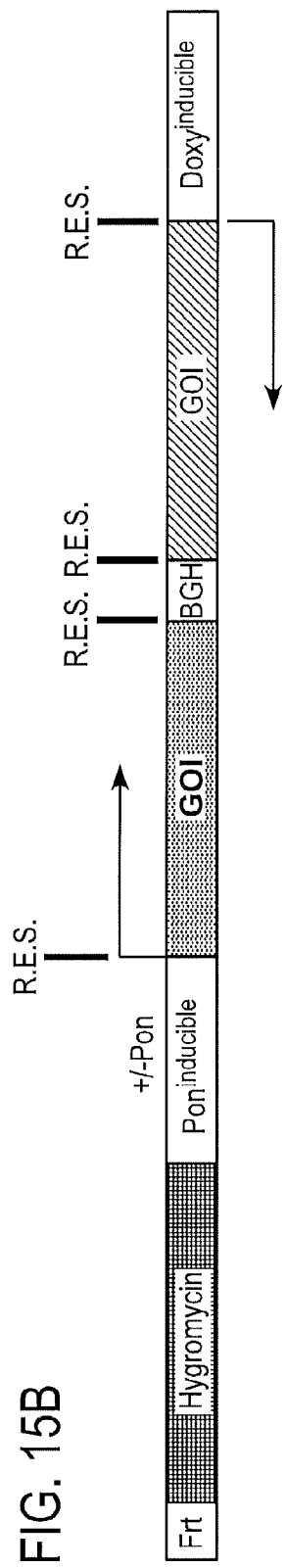

1) and Firefly Luciferase (GOI #2) under the control of the ponasterone ("HS promoter") and TetOn3G ("Tre3G promoter") inducible systems, respectively. Each inducible promoter and gene will be placed in a reverse orientation on opposite 5' strands, so to reduce background non-specific induction. The FRT site will allow Flp recombinase mediated insertion of this vector into the corresponding Frt site found in the genome of the stable T/R FRT cell line generated in FIG. 13. See FIG. 16 for the final orientation of pFRT-dual vector flipped into the T/R FRT locus. Hygromycin cassette will confer resistance to cells that have undergone the successful site-specific recombination. Convenient restriction enzyme sites (R.E.S.) can be engineered into pFRT-dual that will allow any gene(s) of interest to be placed under control of the tetracycline or ponasterone inducible promoters. This is shown in FIG. 15(B).

Figure 16A:
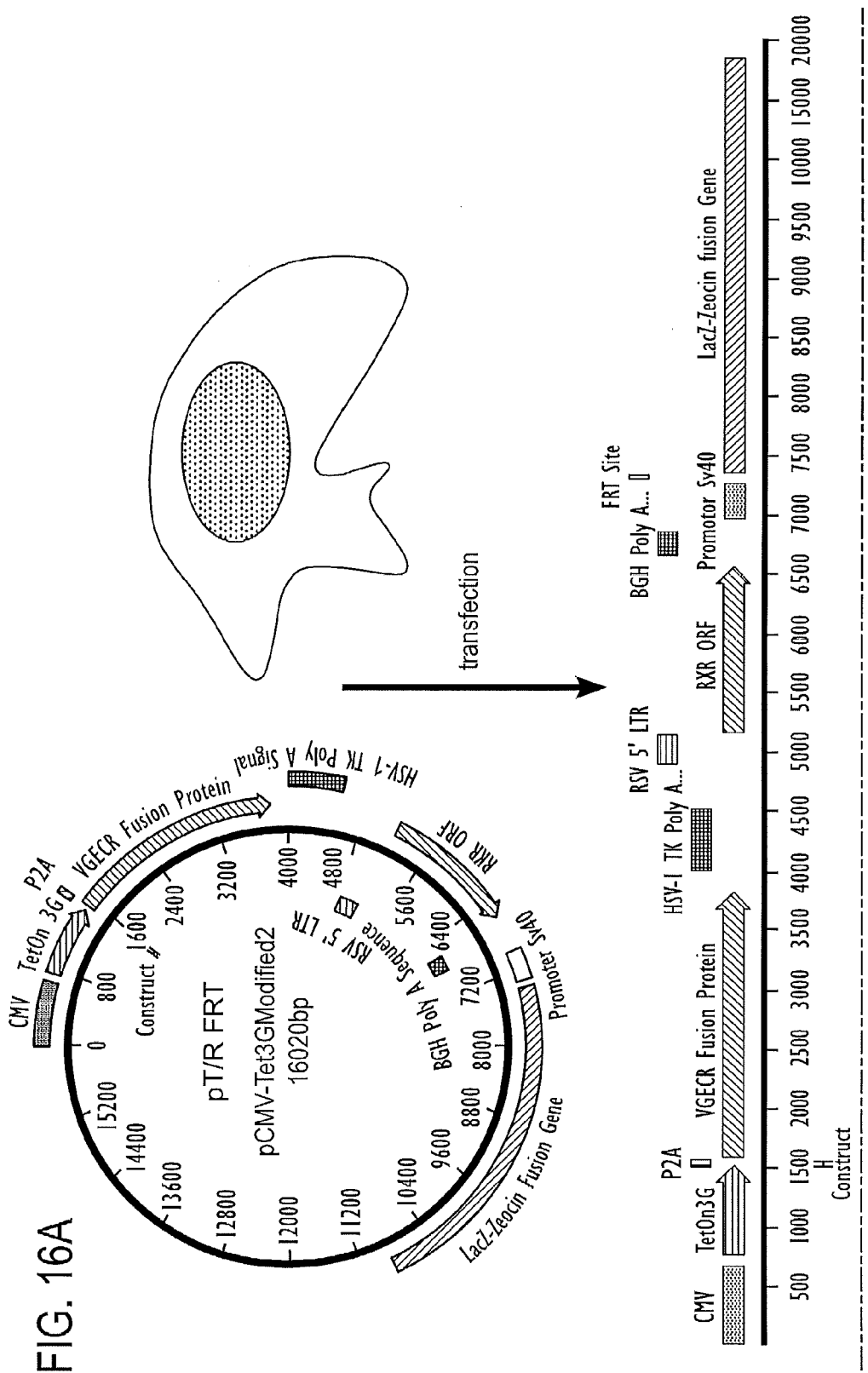
Figure 16B:
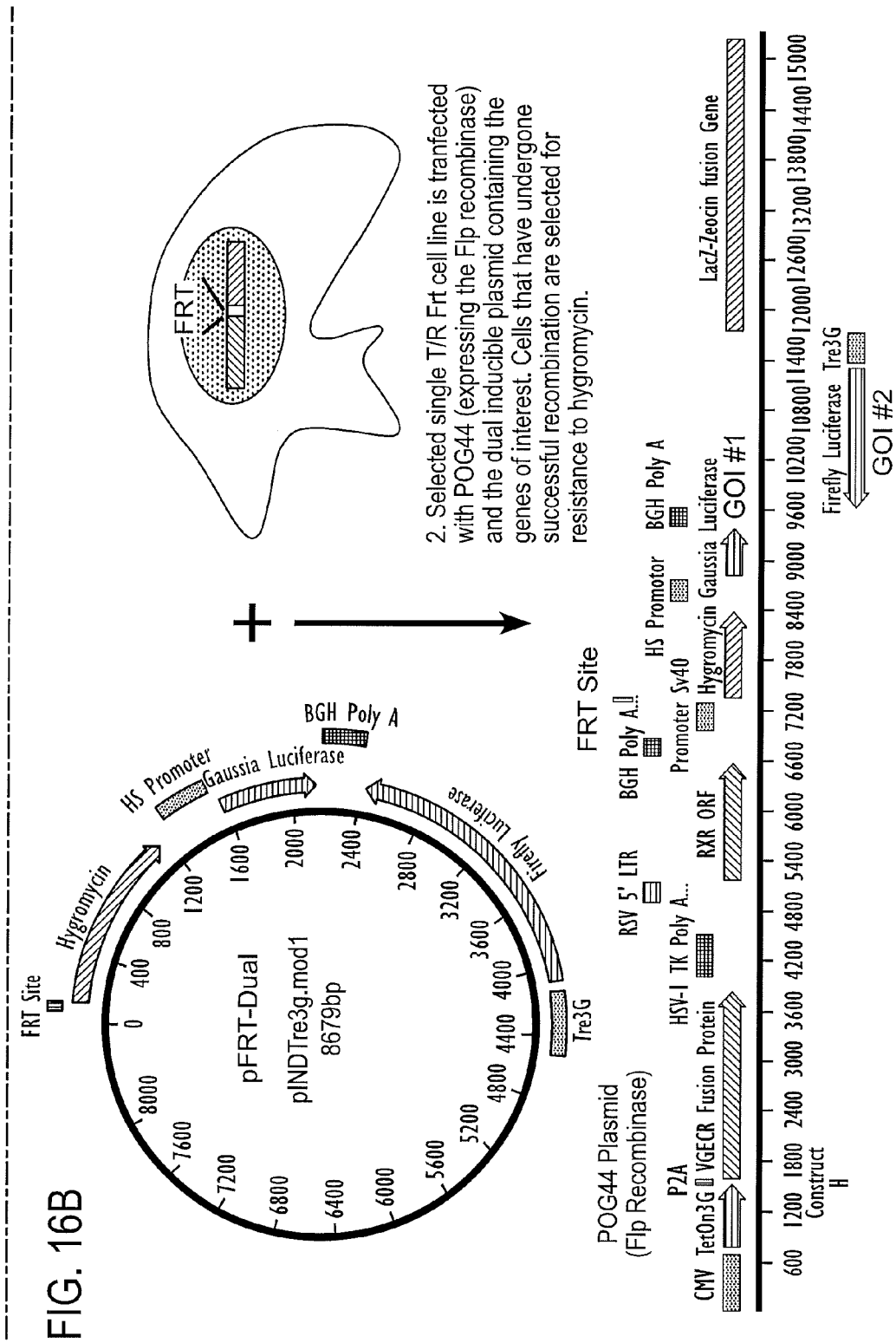

FIG. 16 shows the schematic for generation of the dual-inducible cell line. First, the dual transactivator vector is transfected into any cell line. The cells are initially selected for resistance to Zeocin. Resistant single cell clones are assayed for maximal level of β-galactosidase activity. Second, the selected single T/R Frt cell line is transfected with POG44 and the dual inducible plasmid containing the genes of interest. Cells that have undergone successful recombination are selected for resistance to hygromycin. Third, the gene of interest (GOI) can be simultaneously and independently controlled by the addition of tetracycline or ponasterone.

Figure 17A:
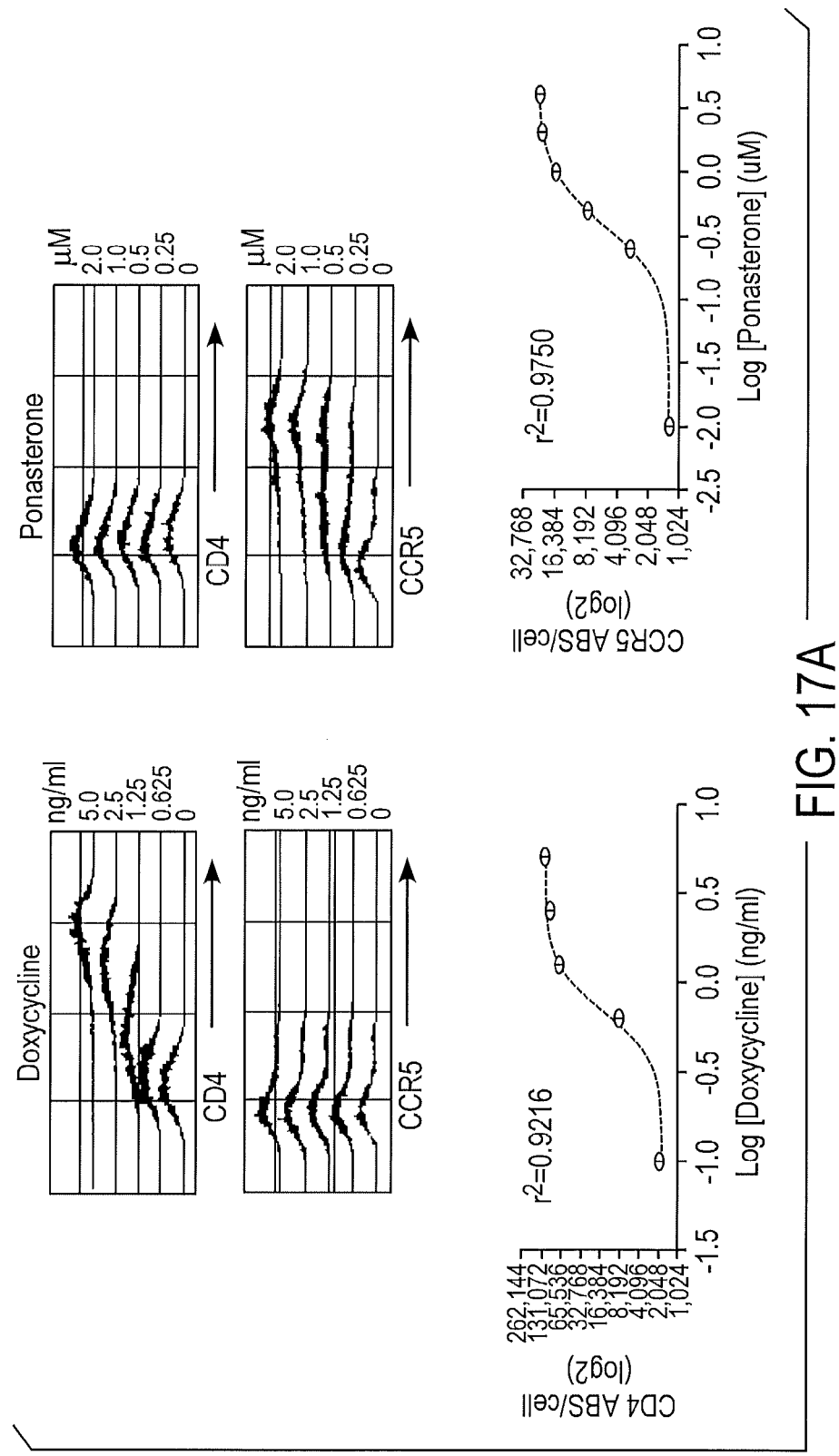
Figure 17B:
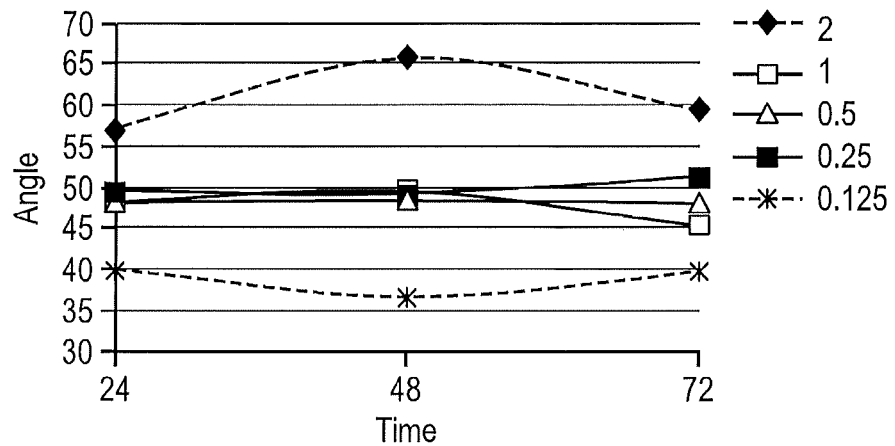
Figure 17C:
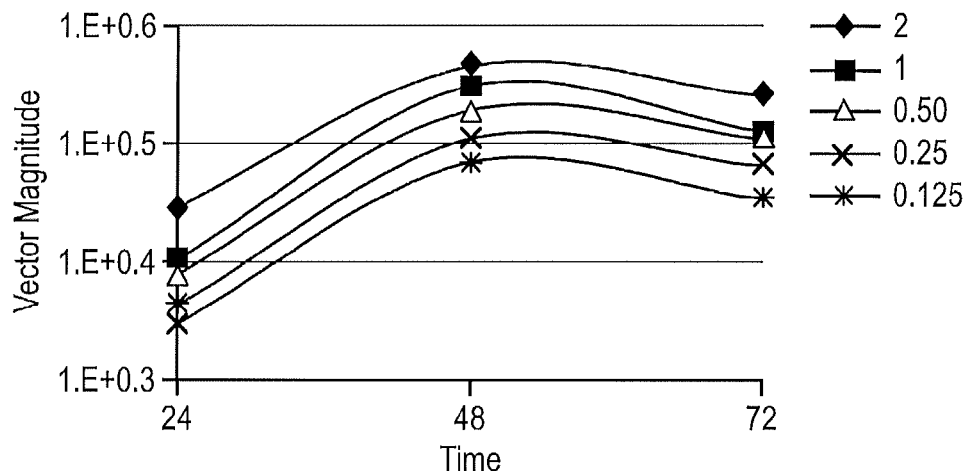
Figure 17D:
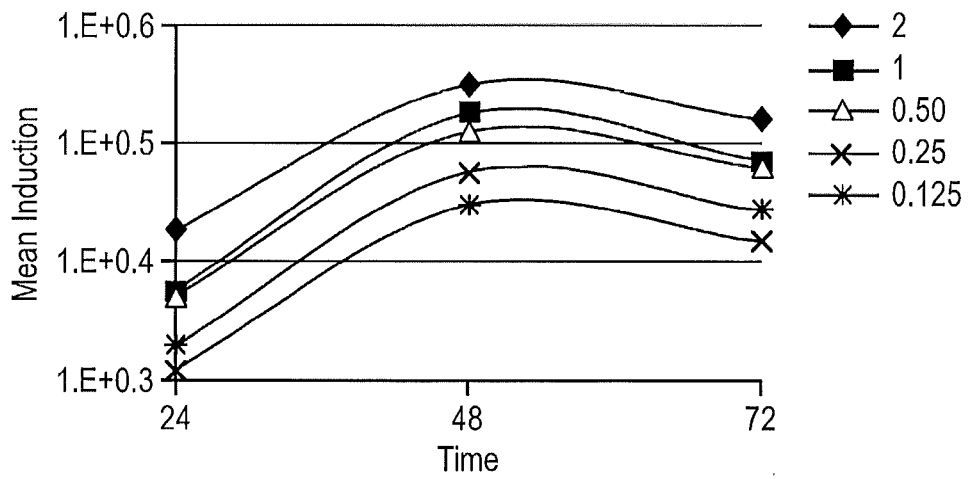

FIG. 17(A) shows that Expression of CD4 and CCR5 can be independently induced with different concentration of Doxycycline (CD4) and Ponasterone A (CCR5) resulting in distinct combination of CD4 and CCR5 expression levels. FIG. 17(B-D) shows the maturation of the sensitivity vectors overtime for different MOIs. FIG. 17(B) shows the sensitivity vector angles charted over time. Infections at MOIs of 1, 0.5 and 0.25 (within linear range of assay) illustrate that vector angle is established at the 24 hour time point and maintained through the 48 hour time point. The 72 hour time point shows an increase in angle variations which is likely due to cell death. Infections at MOIs of 2 and 0.125 (outside of linear range assay) show dramatic variation from the "true" vector angle values at every time point. FIGS. 17(C and D) shows sensitivity vector magnitudes and mean inductions for different MOIs charted over time. Vector Magnitude and Mean Induction show positive correlation with viral input (MOI) at 24 and 48 hours timepoints as predicted by their phenotypic correlate.

Figure 18A:
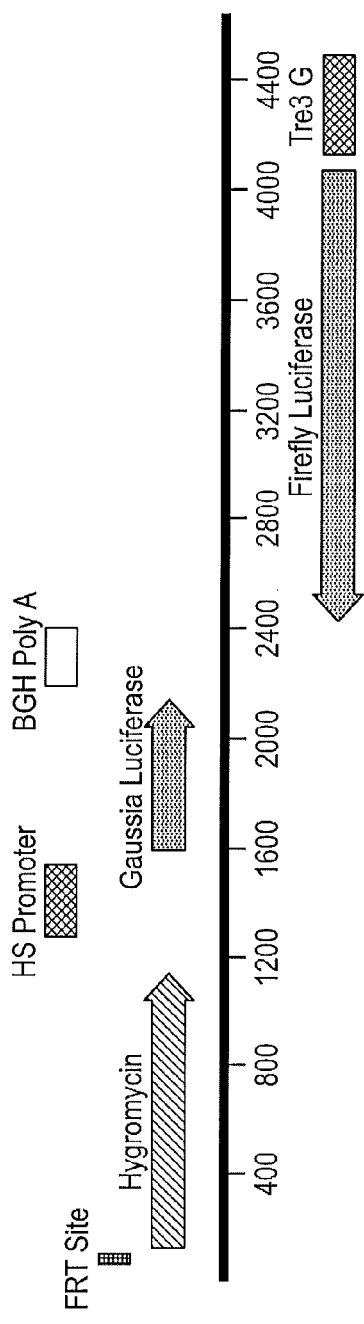
Figure 18B:
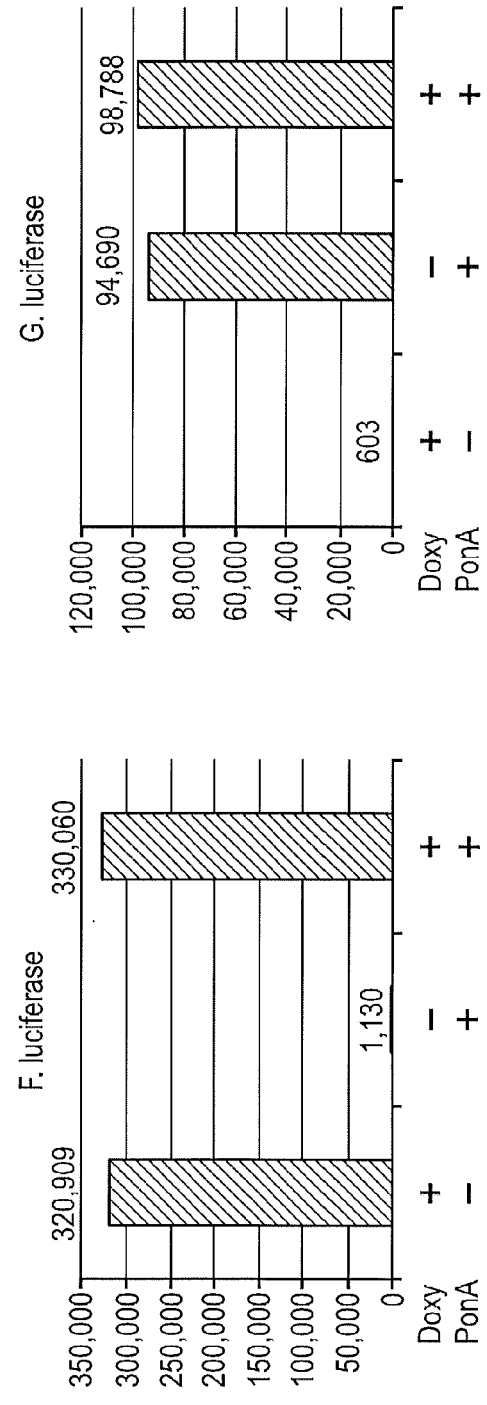

FIG. 18 illustrates that pDual (Tre-Gaussia, IND-Firefly) exhibits simultaneous and independent induction. FIG. 18(A) diagrams the construction of the single vector with induce ability to express Gaussia and/or Firefly luciferase in the presence of Doxycycline and/or Ponasterone A. FIG. 18(B) shows the results from p T/R Frt and pDual (Tre-Gaussia, IND-Firefly) transfected into 293T cells. Six hours after transfection Doxycycline and/or Ponasterone A were added (6 ng/mL for Doxycycline, 4 uM for Ponasterone A) to the transfected cells. Results show that p T/R Frt and pDual (Tre-Gaussia, IND-Firefly) sufficiently induces each luciferase gene only in the presence of the proper induction agent.

FIG. 19 illustrates that CHO T/R Frt can sufficiently induce pDual (mCherry/GFP) in the presence of inducing agents. CHO cells were selected for the stable integration of the pT/R Frt to create CHO T/R Frt. CHO T/R Frt were transfected with pDual (Tre-mCherry, IND-GFP) and inducing agents were added. Results show that CHO T/R frt produce a sufficient amount of the transactivators to drive expression of the reporter genes when inducing agent is added.

Figure 20A:
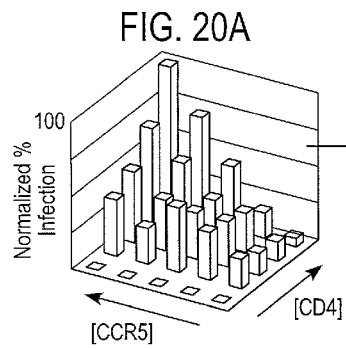
Figure 20B:
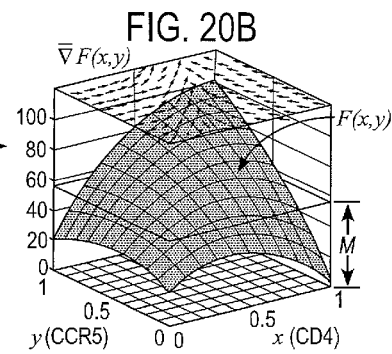
Figure 20C:
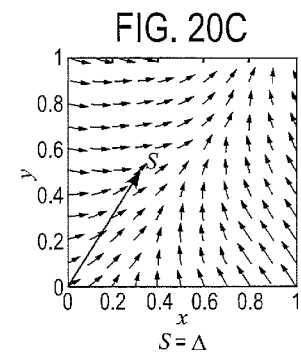

FIG. 20 defines the parameters that impact on the infectivity metrics used for profiling the efficiency of HIV entry. FIG. 20(A) shows the infectivity of an R5-virus (BaL) monitored across 25 distinct combinations of CD4 and CCR5 expression levels. The normalized infectivity profile is shown as a 3-D bar graph with the gLuc activity obtained at the highest CD4 and CCR5 induction level set at 100%. FIG. 20(B) transforms this data into a corresponding 3-D surface plot by fitting the infectivity profile to a continuous polynomial function F(x,y) as previously described (Johnson et al., 2009). The surface function F(x,y) describes the infectivity response of Env as a function of CD4 and CCR5 expression levels, and the resulting 3-D surface plot can be represented by three metrics that reflect distinct phenotypic properties of the infecting virus envelope: (i) the mean infectivity level (M), (ii) the sensitivity vector angle (θ) and (ii) amplitude (Δ). The graphical representations of these three metrics with respect to the 3-D surface plot are indicated in FIGS. 20(B and C). For clarity, the operational definitions of these metrics, and what they measure with respect to the infectious phenotype of Env, are also indicated. These definitions supersede those given in Johnston et al., 2009 as they more accurately described the phenotypic properties of Env that these metrics represent. FIGS. 20(D-F) show that Bal was used to infect GGR Affinofile cells at 5 different MOIs, each MOI across 25 distinct combinations of CD4 and CCR5 expression levels. Every infection condition was monitored at 24, 48 and 72 hpi by sampling supernatant for G.Luc activity. Each infection data point was performed in triplicates. Raw luciferase activity values were normalized to that obtained at the highest CD4/CCR5 induction levels (set as 100%). Normalized data were then used to determine the vector angle, A (FIG. 20(D)), vector amplitude, A (FIG. 20(E)), and Mean infectivity level, M (FIG. 20(F)) via the VERSA computational platform as described.

FIG. 21 shows that Affinofile metrics further illuminate the phenotype of well-characterized point mutants. FIG. 21(A) illustrates the infectivity profile of wt JR-CSF (R5) envelope, and two point mutants: FIG. 21(B) S142N and FIG. 21(C) K421D, previously shown to enhance or perturb CCR5 usage, respectively. Data shown is a representative of two experiments. FIG. 21(D) is a table of the average metrics obtained from FIGS. 21(A-C) and graphically shown in FIG. 21(E). The infectivity profile of each Env was independently repeated twice. FIG. 21(E) is a polar plot representing the metrics obtained from mathematical analysis of the infectivity profile in FIGS. 21(A-C), using the VERSA program as described. The vector angle (θ) is the angle between the x-axis and the dotted line. The vector amplitude (Δ) is represented by the length of the dotted line. The mean infectivity (M) is represented by the size of the circle.

Figure 22A:
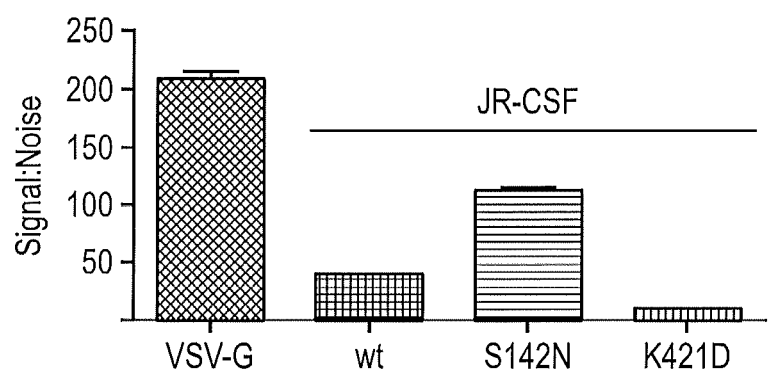
Figure 22D:
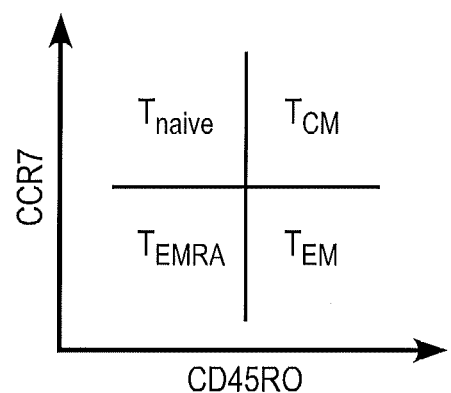
Figures 22B, 22C:
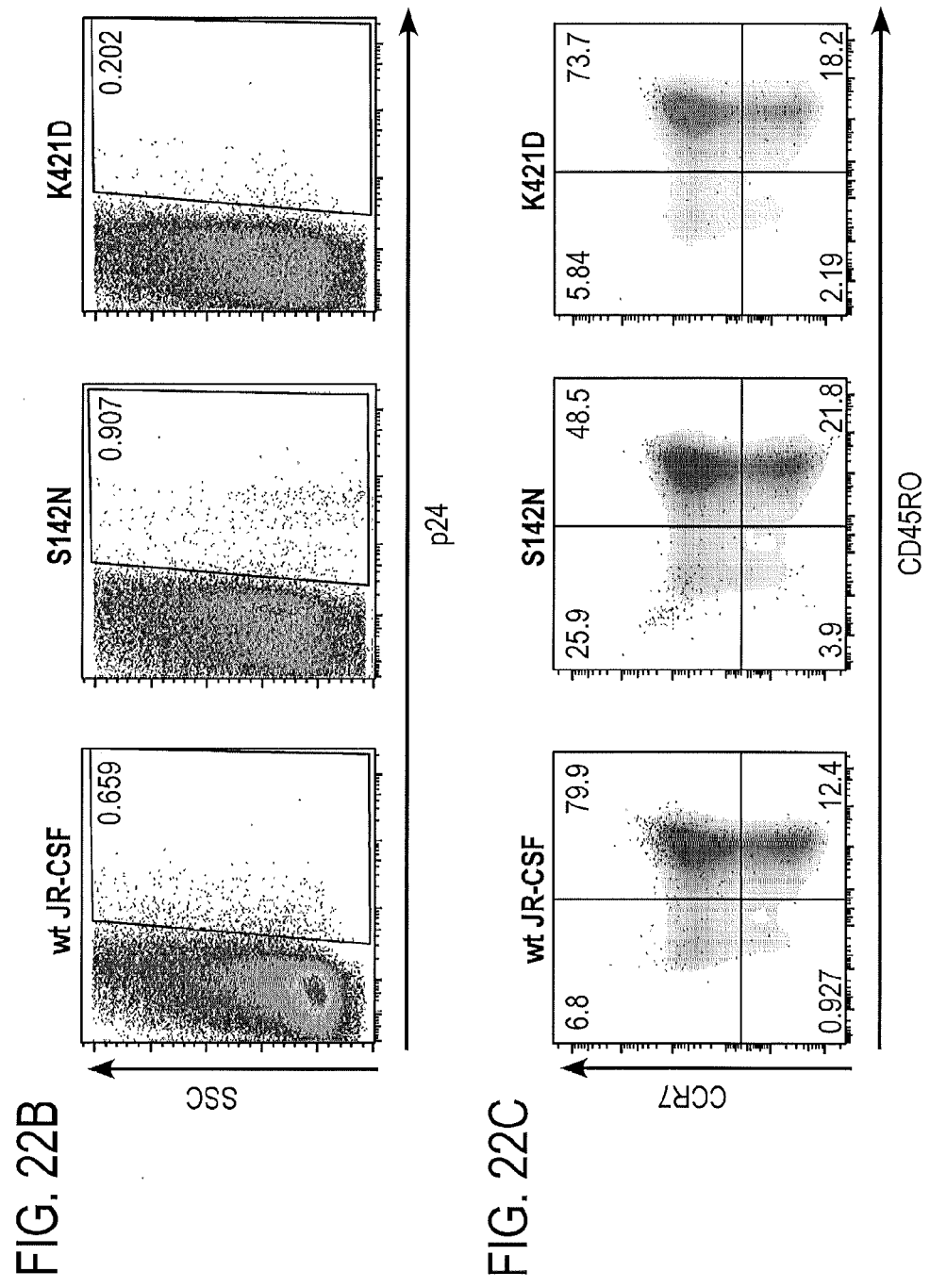

FIG. 22 shows that Affinofile metrics reflect biologically relevant differences in T cell subset tropism. FIG. 22(A) is total PBMCs were infected with luciferase reporter pseudotypes bearing wt, S142N, or K421D JR-CSF envelopes. VSV-G pseudotypes were used as positive controls. All infections (except for VSV-G) could be inhibited by maraviroc (>95%). Error bars represent ranges between two experiments. FIGS. 22 (B and C) are CD8-depleted PBMCs were infected with the indicated pseudotyped viruses at an MOI of 20 (as tittered on Ghost-R5 cells). Three days post-infection, cells were analyzed by multi-color flow cytometry. FIG. 22(B) has infected cells were identified by intracellular p24 staining using PE-conjugated KC57 Mab. FIG. 22(C) has uninfected T-cell subset distribution is shown in grey density plot, while infected p24+ cells are overlaid as the red dots. The percent of total p24+ cells are indicated in each quadrant. All infections could be inhibited by maraviroc (>90%). It is unclear whether the small number of p24+ cells found in CD4+ T-effector RA+ cells (TEMRA, CCR7-CD45RO−) represents a reproducibly infectable population. FIG. 22(D) is a scheme for using CCR7 (PE-Cy7) and CD45RO (FITC) to identify the following T-cell subsets: Naïve (CCR7+CD45RO−), Central Memory (TCM, CCR7+ CD45RO+), Effector Memory (TEM, CCR7− CD45RO+), and Effector Memory RA (TEMRA, CCR7− CD45RO−). Data shown here is a representative of two independent donors.

FIG. 23 illustrates that Affinofile metrics reveal differences in CD4/CCR5 usage efficiencies between Transmitter/Founder (T/F) and chronic envelopes. Normalized infection data using T/F and chronic Env clones were analyzed using VERSA. FIG. 23(A) shows Vector angle, (θ), FIG. 23(B) shows mean infectivity (M), and FIG. 23(C) shows vector amplitude (Δ) values obtained for each Env clone. The vector metrics were first averaged for each individual, and the averaged metrics from the 6 individuals in each group (T/F or chronic, N=12) were then compared. Each Env clone was independently profiled twice across 25 combinations of CD4/CCR5 levels (each data point was done in triplicates). Thus, the metrics were derived from a total of 1,800 infection data points (900 data points from 6 Envs in each group). The median value of each metric for the T/F and chronic Env cohorts is marked by a line. p values were generated by the nonparametric unpaired t test (***, p=0.0003; *, p=0.05). FIGS. 23(D and E) shows the normalized infectivity for the chronic (blue line) and T/F envelopes (red line) averaged, and compared as a group at FIG. 23(D) low and FIG. 23(E) high levels of CCR5 expression, across varying levels of CD4 as indicated. FIG. 23(F) shows a wedge plot of the average and values (+/−S.D.) obtained for T/F (dark grey) versus chronic envelopes (light grey). FIG. 23(G) shows the infectivity profile of individual T/F and chronic Envs (from FIG. 27) averaged to form their respective group profile. 2-D contour plots representing the averaged infectivity profiles of T/F and chronic envelopes are shown.

Figure 23A:
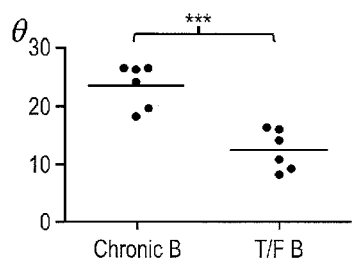
Figure 23B:
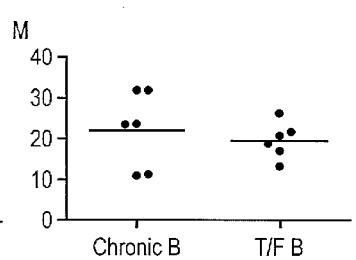
Figure 23C:
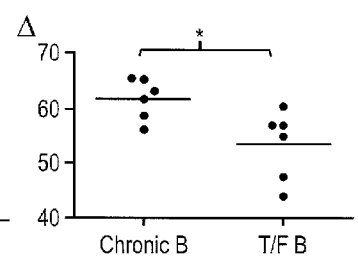
Figure 23D:
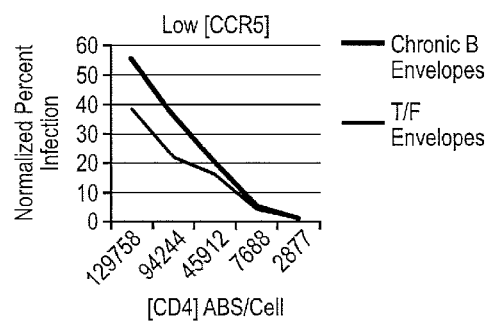
Figure 23E:
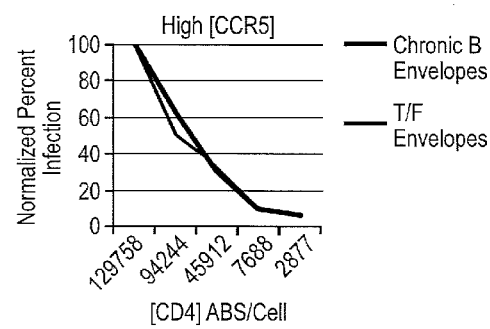
Figure 24A:
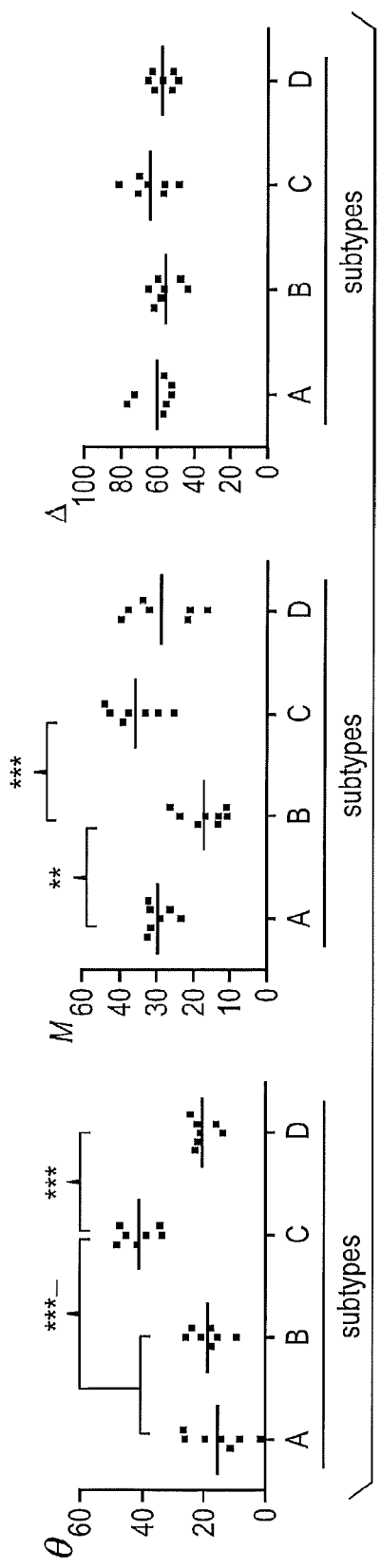
Figure 24B:
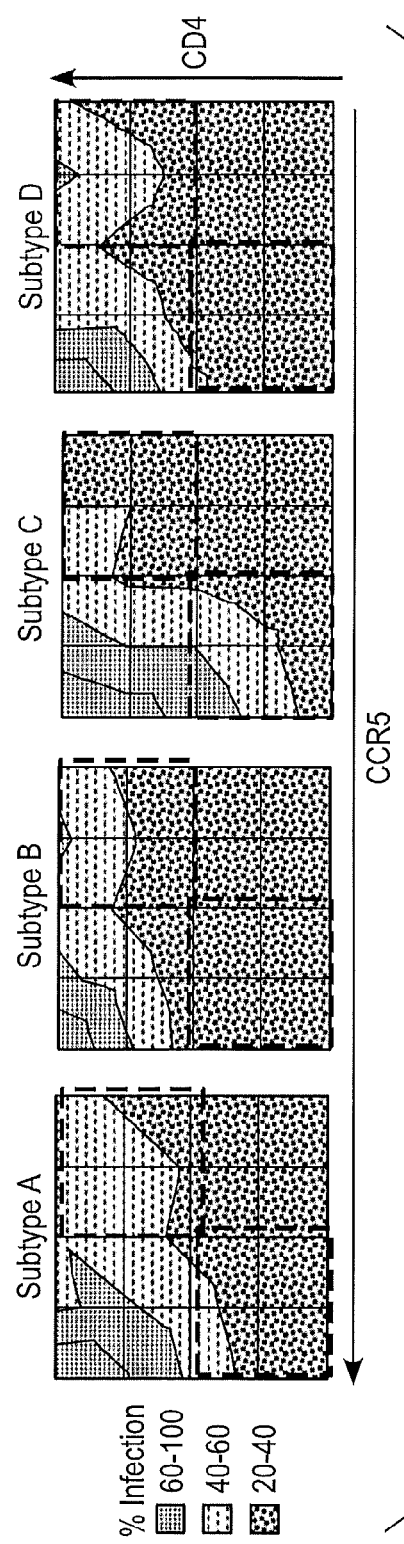
Figure 24C:
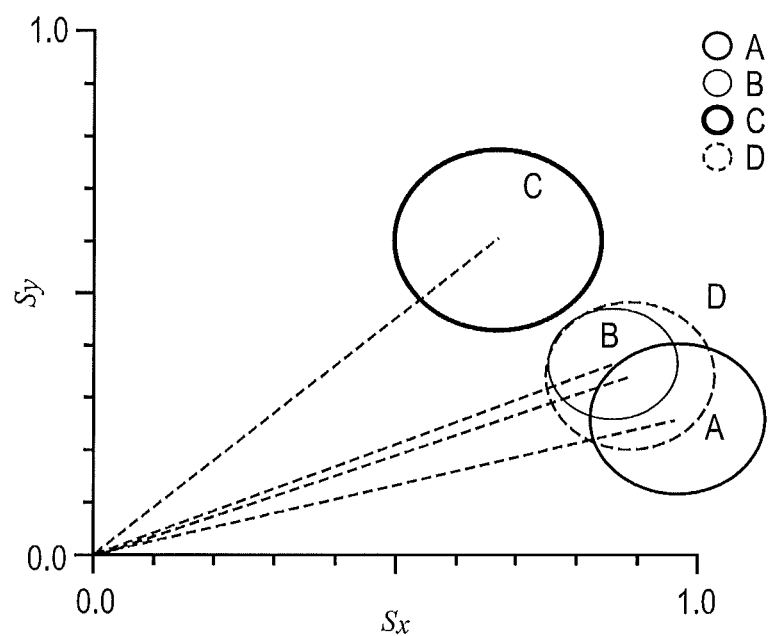

FIG. 24 shows that HIV envelopes exhibit subtype-specific differences in CD4/CCR5 usage efficiencies. FIG. 24(A) shows normalized infection data from each Subtype A, B, C and D envelope clones (n=28) analyzed by VERSA. The vector metrics were averaged for at least two independent infections (with a variance <5%) for each envelope in each subtype group. Vector angle (A), mean infectivity (M), and vector amplitude (A) values for each envelope are shown as grouped by subtypes. P values were generated by the nonparametric unpaired t test (p*<0.005, p<0.05). FIG. 24(B) is 2-D contour plots of the average infectivity profile for each subtype, generated and color coded as in FIG. 23. The colored dashed square boxes compare the infectivity differences noted between subtype C (blue) Envs and others (red) in the lower left (LL) and upper right (UR) quadrants. Each Env clone was independently profiled twice. FIG. 24(C) is a polar plot of the averaged sensitivity vectors obtained from each subtype, generated as in FIG. 21.

Figure 25D:
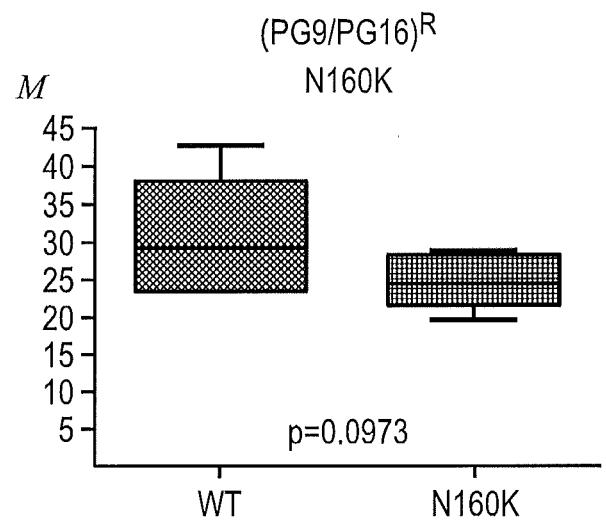
Figure 25E:
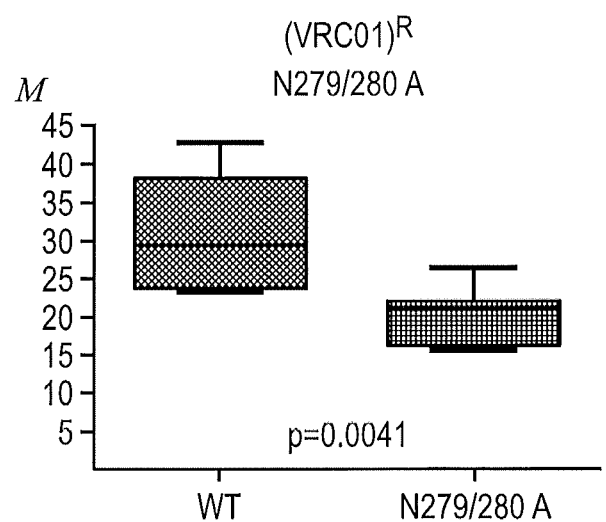

FIG. 25 shows that Affinofile profiling reveals that resistance to broadly neutralizing antibodies (BNAbs) also results in reduced entry efficiency. N160K and N279A mutations were engineered into a random sample of 12 subtype A-D Envs, The resultant (PG9/16)R and (VRC01)R resistant Envs were assayed for CD4 and CCR5 usage efficiency along with their parental BNAb sensitive Envs. GGR Affinofile profiling was performed as described. FIG. 25(A-C) shows 2-D contour plots of the infectivity profiles for WT, (PG9/PG16)R, and (VRC01)R Envs. Contour plots are ordered from highest mean induction to lowest, from left to right. FIG. 25(D-E) shows the mean values and interquartile ranges of the Mean infectivity (M) for (PG9/PG16)R or (VRC01)R resistant Envs in all subtypes compared to their WT counterparts. P values calculated via Mann-Whitney test.

Figure 26A:
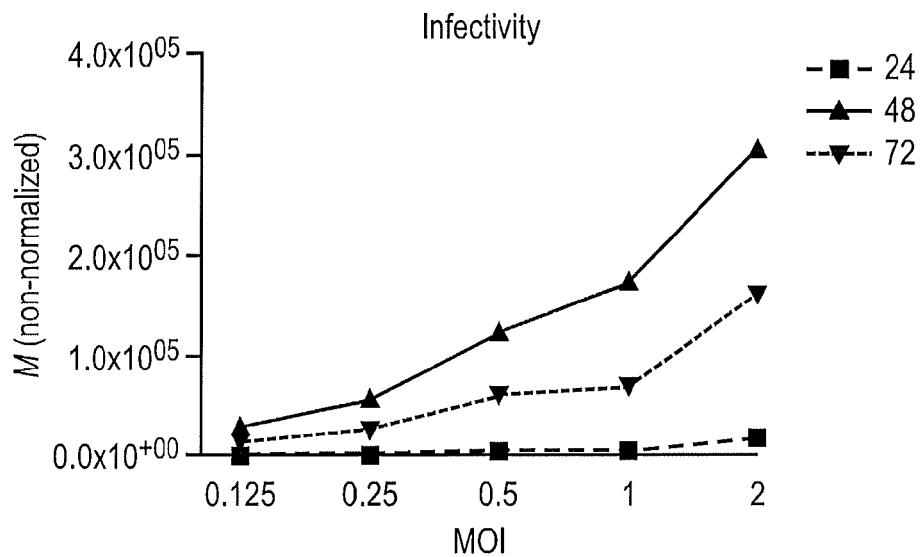
Figure 26B:
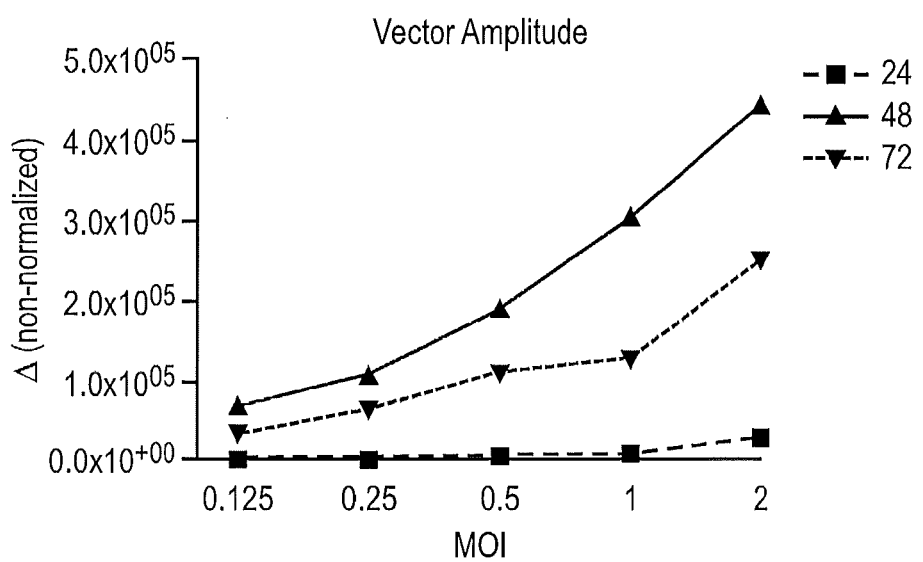

FIG. 26 shows that the use of raw luciferase infection data results in variable vector metrics. Mean infectivity and vector amplitude results are provided in FIGS. 26(A and B). Raw luciferase infection data from the data set presented in FIG. 20 was inputted into VERSA.

FIG. 27 shows individual GGR plots for T/F and Chronic Envelopes. The GGR data for FIG. 27(A) Chronic and FIG. 27(B) T/F-derived envelopes, which are representative of at least 2 independent experiments, were generated and plotted as described. The contour plots are arranged from highest to lowest mean infectivity, from left to right.

Figure 28A:
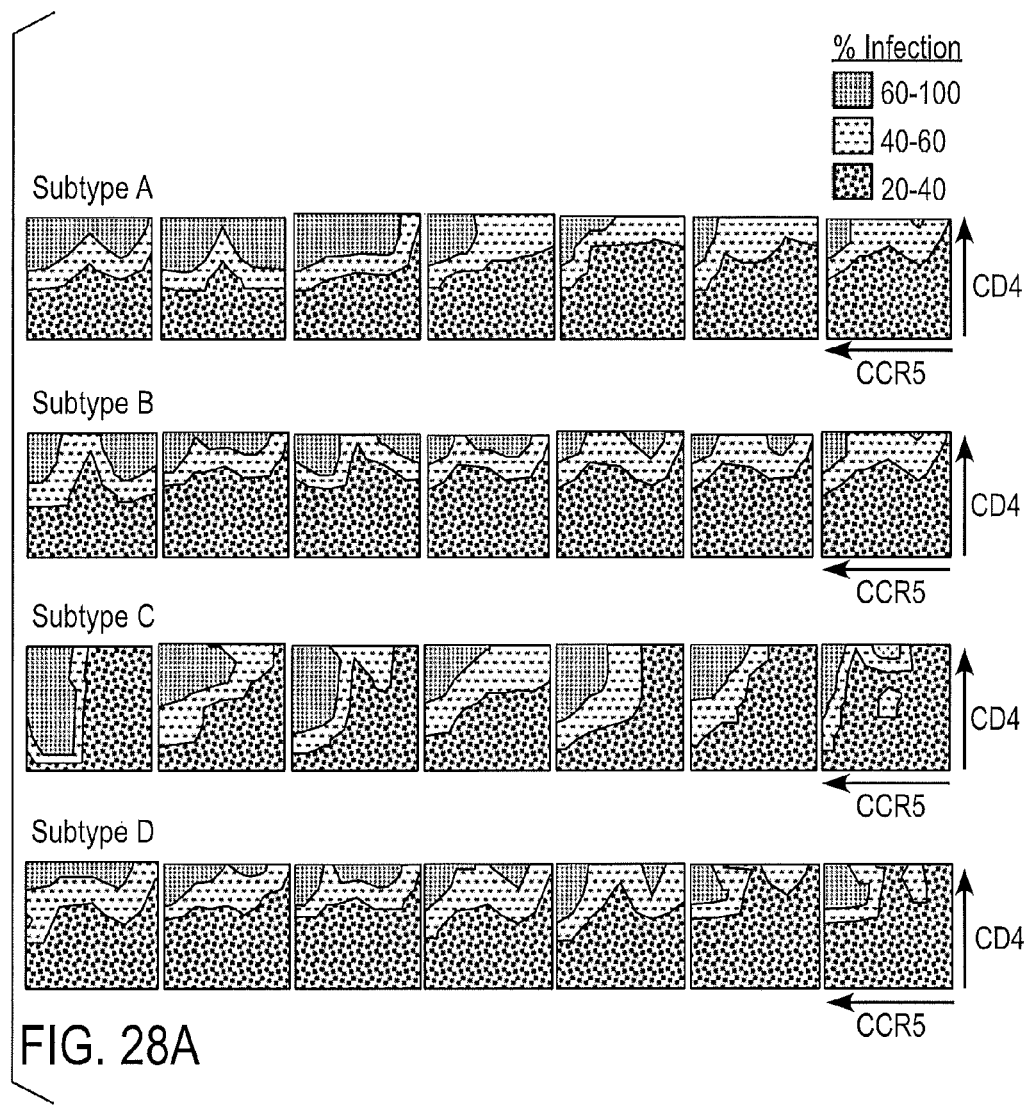

FIG. 28 shows individual GGR plots for subtype envelopes. FIG. 28(A-D) has the GGR data for Subtype A-, B-, C-, and D-derived Envs, which are representative of at least 2 independent experiments, generated and plotted as described. The contour plots are arranged from highest to lowest mean infectivity, from left to right.

Figure 29A:
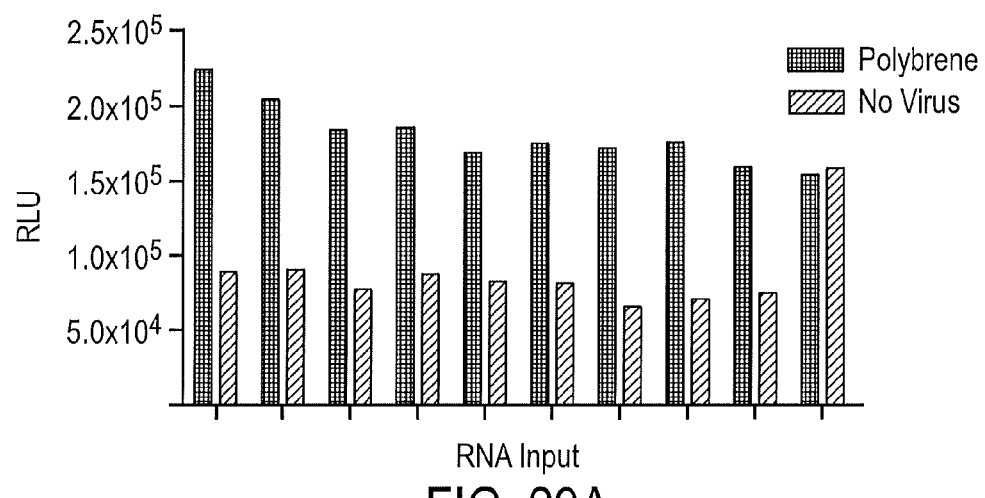
Figure 29B:
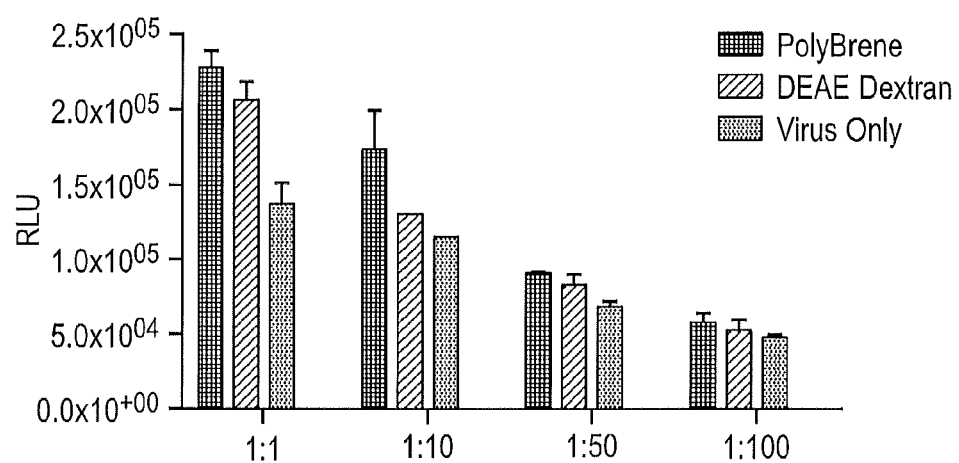

FIG. 29 shows that GGR Affinofile cells can detect the presence of HIV in patient plasma samples. FIG. 29(A) has GGR cells maximally induced with doxycycline (4 ng/ml) and ponasterone (4 uM) at the time of their seeding. 16-21 hours post-seeding/induction, cells were infected with serial dilutions of HIV positive plasma in the presence of polybrene. Four days post infection supernatant was collected and assayed for Gaussia Luciferase expression. Results indicate virus can be detected from untreated HIV positive plasma. FIG. 29(B) determines the use of a commercially available concentration reagent to improve the signal from HIV positive plasma. A small aliquot of HIV positive plasma was prepared according to the RETRO CONCENTIN protocol. Concentrated virus samples were diluted and used to infect maximally induced GGR Affinofiles in the presence or absence of polybrene or DEAE Dextran. Results demonstrate GGR cells can readily detect virus in concentrated and diluted samples. Table 2 shows the cumulative results and patient data of all the plasma samples tested so far.

Figure 30A:
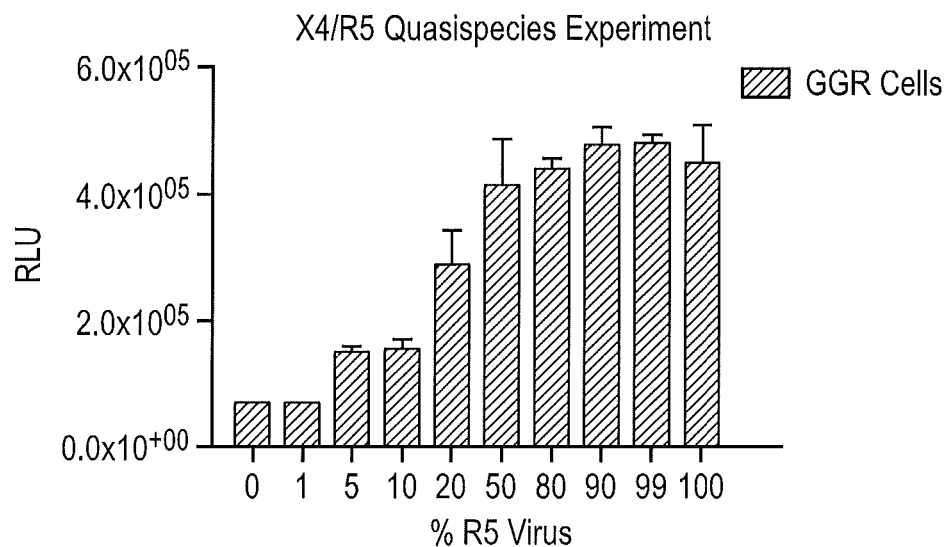
Figure 30B:
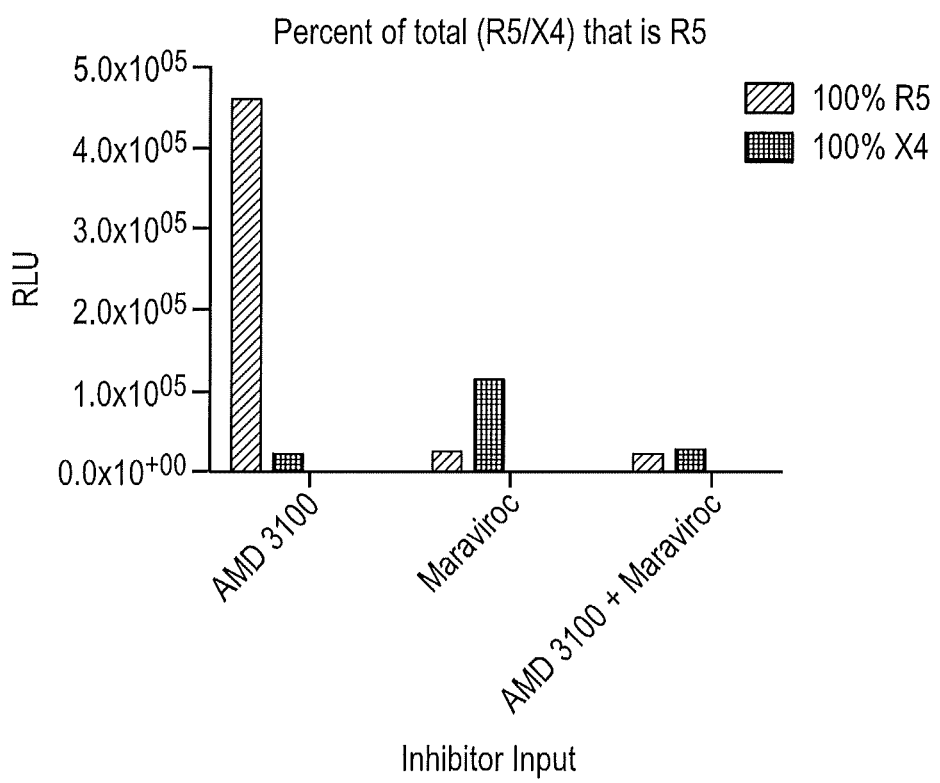

FIG. 30 shows that GGR Affinofile cells can detect minor X4 qausispecies. The 293 based GGR Affinofile cells constitutively express a small but significant amount of the other primary HIV receptor CXCR4. FIG. 30(A) demonstrates that the amount of CXCR4 present on GGR Affinofile cells can support infection by X4 using virus. Cells were maximally induced and infected with mixtures of X4 and R5 viruses. Results indicate that X4 using variant are readily detected by GGR Affinofile cells. FIG. 30(B) is a control experiment demonstrating that infection is specifically inhibited (>90) when the matching coreceptor inhibitor is used (CCR5 inhibitor, Maraviroc and/or CXCR4 inhibitor, AMD 3100).

Figure 31C:
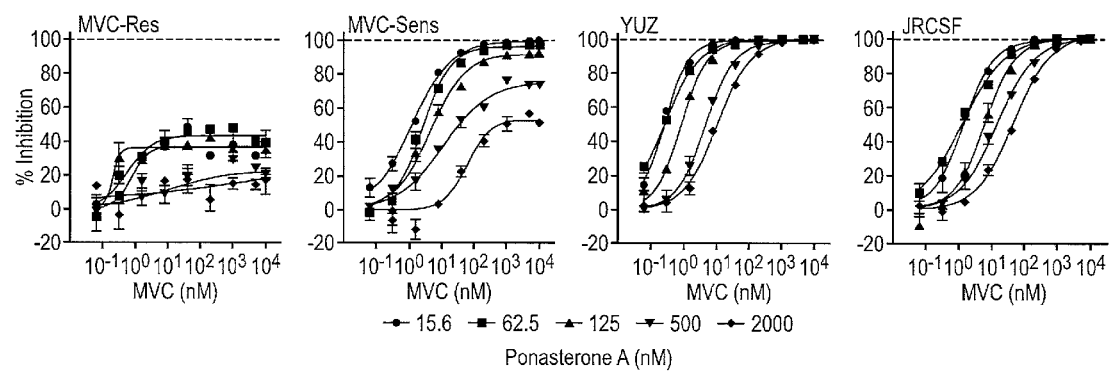

FIG. 31 shows intrinsic resistance to FDA approved inhibitor revealed on Affinofile cells. FIG. 31(A) demonstrates that Affinofile and GGR Affinofile cells have the ability to express CD4 and CCR5 at levels that are comparable to most HIV cell lines and relevant primary cells. The amount of doxycycline and ponasterone A present finely induce the amount of CD4 and CCR5 expressed on Affinofile and GGR cells. FIG. 31(B) illustrates that HIV indicator cell lines with low to moderate levels CCR5 expression are unable to reveal the inherent ability of the maraviroc "sensitive" clone to use the maraviroc bound form of CCR5. This is true for the U87 CD4/CCR5 cell line used by LabCorp's TROFILE Tropism assay. Only cells that express high levels of CCR5 can reveal the inherent resistance of the clone, NP2CD4/CCR5 and Affinofile/GGR cells. FIG. 31(C) illustrates that Affinofile cells induced to express distinct levels of CCR5 demonstrate that only in cells with high levels of CCR5 can intrinsic resistance to maraviroc be revealed.

Maximal Induction of GGR Cell Line

GGR cells were seeded into tissue culture plates (24-, 48- or 96 well plates). Simultaneously, cells are induced to express CD4 and CCR5 by adding doxycycline and ponasterone at a final concentration of 4 ng/mL and 4 um, respectively. 16-21 hours post seeding and induction, induction media is removed and replaced with media or serum (potentially) containing varying amounts (MOIs) of HIV as indicated in FIG. 3A-B. Infections were synchronized by spinoculation at 37 C for 2 hr (@1,200 g) before transfer to 37 C at 5% CO2. At the indicated timepoints after infection, 10 ul of the cell supernatant was collected and assessed for *gaussia* luciferase activity. FIG. 3A shows that at low-moderate MOI (Multiplicity of Infection), the signal:noise of Gaussia luciferase induction was close to 20 as early as 24 hours post-infection. By comparison, the standard assay in the field using the (firefly) luciferase HIV reporter backbone (e.g., NL4-3 deltaEnv-luc) requires a minimal of 72 hours for optimal signal detection. Increasing either the amount of viral inoculum used, or the amount of time post-infection before analysis of G.Luc activity, increased the sensitivity of virus detection. Thus, while G.Luc activity could be detected at 20-fold above background as early as 17 hpi using a relatively high MOI of 0.5, GGR cells were also able to detect infection using ~10-fold less virus (MOI 0.0625), and with equal sensitivity, but only at 72 hpi (FIG. 3(A)). To determine if G.Luc activity in the infected culture supernatant reflected the level of virus infection monitored by more familiar assays, such as intracellular p24 staining, GGR cells were infected with JR-CSF Env pseudotyped pNL-luc virus at an MOI of 0.25 over a range of CD4 and CCR5 expression levels. At 72 hpi, G.Luc activity in the supernatant was simultaneously determined with intracellular p24 levels. FIG. 3B shows that the amount of G.Luc production at different levels of CD4/CCR5 induction mirrors the amount of infection monitored by intracellular staining for viral antigen (p24) (due to direct detection of viral antigen production in infected cells). However, intracellular p24 staining is laborious (~4-6 hours of hands-on manipulation followed by hours of FACS analysis by hand vs 10 min for G.Luc when using multi-channel pipette to transfer 10 ul of supernatant for luminometry), and not scaleable to 96- or 384-well for high throughput analysis (such as may be required in clinical trial monitoring or when used as a commercial test).

At the final time-point, cells may be collected and assessed for GFP fluorescence. Simple visualization of the cells by fluorescence microscopy allows for monitoring the progress of infection. Infection of control wells with VSV-G lentiviral pseudotypes (that is not dependent on CD4/CCR5 expression levels) in the absence or presence of induction agent (doxycycline or ponasterone) serves as an internal quality control for the number of permissive and infectable cells.

Using the GGR cell line, the infectivity of a given Env, in the context of a pseudotyped reporter virus, can be profiled across 24-48 distinct combinations of CD4 and CCR5 expression levels. To assist in describing and comparing the infectivity data associated with numerous viral Envs from various cohorts and research groups, the automated computational web-based tool, Viral Entry Receptor Sensitivity Analysis (VERSA) (available at versa.biomath.ucla.edu) may be used. For a given Env, the VERSA program permits the rapid distillation of the set of infectivity data points into three metrics that grossly describe the Env's CD4 and CCR5 usage pattern and entry efficiency. This reveals the distinct pathophysiological Env phenotypes associated with differential CD4/CCR5 usage efficiencies.

The three metrics are: M, the mean infectivity, provides a rough estimate of the overall efficiency of entry; $\Theta$, the sensitivity vector angle, a measure of the relative infectivity response to changes in CD4 versus CCR5 levels; and, $\Delta$, the vector amplitude, which measures the combined rate of increase of infectivity as a function of CD4 and co-receptor concentrations. A virus that is predominantly sensitive to changes in CCR5 levels and not CD4 will have $\Theta$ near 90°, while $\Theta \sim 0°$ for a virus that is only sensitive to changes in CD4 levels but not CCR5. A virus equally sensitive to changes in both CD4 and CCR5 levels would have $\Theta \sim 45°$. While the above contemplates CD4 and CCR5, this should not be considered limiting, for if the objective is to examine the efficiency of CD4 usage for CXCR4 viruses, the basal level of CXCR4 present in the GGR cell line will permit this, as the X4 Env HxB effectively gives infectivity plots with a vector angle close to zero degrees.

R5 virus infection of GGR cells across a spectrum of CD4 and CCR5 expression levels generated an infectivity profile (FIG. 20(A)) that can be mathematically represented by a surface function F(x, y) (FIG. 20(B)), which describes the infectivity response as a function of CD4 and CCR5 cell surface expression levels (Johnston et al., 2009). The salient features of this surface plot can be captured by three biophysically meaningful parameters illustrated in FIGS. 20 (B and C): the mean infectivity level M, and the angle $\theta$ and amplitude $\Delta$ of the sensitivity vector. The operational definitions of these parameters are indicated in the panels below FIG. 20(A-C). Their mathematical definitions and formulations have been reviewed recently (Chikere et al., 2012). Together, these three metrics quantitatively describe the phenotypic behavior of a given viral envelope in response to changes across a spectrum of CD4 and CCR5 expression levels.

To determine the precision and robustness of these three metrics across a range of infection and detection parameters, GGR cells were infected—induced to express 25 distinct combinations of CD4 and CCR5—with a prototypic R5 virus (BaL), over a 16-fold range of viral inoculums, and monitored infectivity at 24, 48 and 72 hpi. FIG. 20(D) shows that the angle $\theta$ of the $\vec{s}$ is relatively insensitive to changes in the amount of viral inoculum used, remaining close to 45° except at the highest level of inoculum used (MOI=2). At high MOIs, the vector angles were more variable between repeats, likely due to multiple infections per cell and other inherent toxicities associated with a high viral inoculum. Notably, at MOIs less than 2, the angles did not change regardless of whether the infectivity data was obtained at 24, 48, or 72 hpi. The mean amplitude of the infection response ($\Delta$), and the mean infectivity (M) were similarly stable across a wide range of MOIs (FIG. 20(E-F)). Similar to the angle metric, the amplitude ($\Delta$) and mean infectivity (M) metrics obtained at a high MOI (of 2) were also more variable, and likely not reflective of the Env's true phenotype. In contrast to the stability of these VERSA metrics obtained using normalized infectivity data, the A and M metrics obtained using raw luciferase activity values varied markedly as a function of MOI and time of detection post-infection (FIG. 26).

GGR cells can be used to characterize a range of distinct Env phenotypes (FIG. 4) and the infectivity profile of each Env can be represented by the set of three metrics (FIG. 4(B)). Notably, all three metrics (θ,Δ,M) for a given Env can be represented on a polar plot, and the metrics for each Env appear to be highly reproducible (FIG. 5). These derived metrics distill the phenotypic properties of a particular Env from a rich set of experimental data, and provide a quantitative tool to segregate Envs based on their functional phenotype. A better understanding regarding the physiological correlates of these metrics might also help illuminate the biological behavior of HIV-1 Envs, and shed light on the complex determinants of HIV-1 tropism and entry.

GGR can be induced to express varying levels of CD4 and CCR5, and entry efficiency or resistance to entry inhibitors can be tested at varying levels of CD4/CCR5 in order to capture a more biologically complete picture of the viral entry phenotype of particular viral isolates. GGR cells are seeded into a 24-well, 48 well, 96 well or 384 well tissue culture treated plate. Cells are simultaneously induced to express CD4 and co receptor (CCR5) by adding varying concentrations of ponasterone (0-4 um) and doxycycline (0-4 ng/mL) in distinct combinations. 16-21 hours after seeding and induction, induction media is replaced with media or serum (potentially) containing HIV. Alternatively, prior to replacing media with infectious media, entry inhibitors can be added and incubated with cells for 30 mins before the addition of infectious media. Infections will be synchronized by spinoculation at 37 C for 2 hr (@1,200 g) before transfer to 37 C at 5% CO2. At various time-points after infection, 10 ul of the cell supernatant can be collected and assessed for G.Luc activity. If required, at the final timepoint, cells can also be collected and assessed for GFP fluorescence.

FIG. 4 shows representative 3-D plots of how different viruses with known phenotypes can give a unique 3-D infectivity profile that is a function of CD4 and CCR5 expression levels. This data can be mathematically deconvolved into a vector with at least 3 metrics (vector angle, magnitude (slope) and mean induction) that robustly captures the intrinsic biological phenotype of any particular env. The technical details are provided in the Johnston et al., J Virol, 2009, and have been verified by multiple other publications (e.g., Agrawal-Gamse et al., 2009; Pfaff et al., 2010). It is important to note that these previous publications uses the parental 293-Affinofile cells and relies on using HIV env pseudotyped luciferase reporter vectors. The described GGR system can be used for these kinds of studies, but in a more high-throughput fashion, using primary isolates that have not been cloned. Thus, the vector metrics can be obtained that represent the gestalt or average of the uncloned viral population present in patient plasma. Prior to this application, this has never been possible, even in principle, when using traditional techniques. Even if one could sequence the entire viral diversity in a particular patient sample, it would have been practically impossible to clone and test every single envelope variant.

To further validate how Affinofile metrics may reflect changes in CD4/CCR5 usage efficiencies, two point mutants in JR-CSF with well-described, but diametrically opposed effects on CCR5 binding were examined. S142N, a V1 loop mutant (Boyd et al., 1993), confers on JR-CSF the ability to enter a number of T-cell lines with vanishingly low levels of CCR5 (Lee et al., 1999; Dejucq et al., 1999), while K421D is a "bridging sheet" mutant that reduces the affinity of gp120 for CCR5 (Reeves, 2002; Rizzuto, 1998). Viruses pseudotyped with wild type (wt) JR-CSF, or with S142N or K421D Env mutants were produced and titrated on Ghost-R5 cells where CD4 and CCR5 levels were non-limiting. An equivalent MOI of each pseudotype was then used to infect GGR cells expressing 25 distinct combinations of cell surface CD4 and CCR5 levels.

Compared to wt JR-CSF (FIG. 21(A)), the S142N mutant exhibited enhanced entry at every level of CCR5 at or above a specific threshold level of CD4 (0.4 ng/ml Dox) (FIG. 21(A)). This is apparent when comparing the rows of green, yellow, orange and red bars along the CCR5 axis in FIG. 21(A). Thus, S142N was more responsive to changes in CCR5 levels than wt JR-CSF. This phenotype is reflected as an increase in θ from 30.5° to 38° for JR-CSF and S142N, respectively. Recall that a relative increase in vector angle (towards 90° as θ approaches the y-axis) indicates that an Env's infectivity is more sensitive to changes in levels of CCR5. A summary of the vector metrics is given in FIG. 21(D), and illustrated in FIG. 21(F) as a polar plot. For S142N, its ability to use CCR5 efficiently also enhances its infectivity at any given level of CD4; thus, the overall level of infection across the entire matrix of CD4/CCR5 expression levels is also higher. This overall increase in infectivity is reflected in the increase in M from 20 to 40.5 for wt JR-CSF and S142N, respectively (FIG. 21(D-E)) and also graphically represented by the size of the circle in FIG. 21(E). The combination of an increase in A and M supports the conclusion that S142N uses CCR5 more efficiently than wt JR-CSF.

In contrast, K421D showed inefficient entry at the lowest two levels of CCR5 (<20% of maximal infectivity at 0 and 0.25 μM PonA) regardless of how much CD4 was present (FIG. 7(A)), consistent with the known role of this K421 bridging sheet residue in mediating co-receptor interactions (Reeves, 2002; Rizzuto, 1998). Interestingly, at high CCR5 levels (2 and 1 μM PonA), K421D responded more dramatically to increasing levels of CD4 than wt JR-CSF. These phenotypic properties are reflected by the decrease in θ for K421D)(23° compared to wt JR-CSF (30.5°), and a concomitant increase in Δ (50.5 to 69.5 for wt and K421D, respectively) (FIGS. 21(D) and 7(B)). Just as an increase in θ for S142N indicates that its infectivity is more sensitive 220 to changes in levels of CCR5, a decrease in for K41D indicates that on average, the infectivity of K421D is more sensitive to changes in CD4 levels compared to wt JR-CSF. However, the mean infectivity (M) for K421D was only moderately decreased compared to wt JR-CSF (16.5 vs 20, FIGS. 21(D) and 7(B)). This likely reflects K421D's compensatory increase in the magnitude of its infectivity response to high CD4/CCR5 levels. Collectively, these results reveal that high levels of CD4/CCR5 may compensate for the inefficient entry exhibited by the K421D mutation at low CCR5 levels.

To determine how these Affinofile metrics reflect the ability of a viral Env to infect primary CD4+ T-cells, total PBMCs were infected with pseudotyped luciferase reporter viruses bearing wt JR-CSF, S142N or the K421D Env mutants. FIG. 22(A) shows that the S142N virus infected PBMCs better than wt JR-CSF while the K421D virus exhibited the lowest level of infection. This pattern reflected the θ and M metrics of the respective viruses, as the limiting parameter on primary CD4+ T-cells are the levels of CCR5 (low), not CD4 (high).

Next, CD3/CD28 stimulated CD4+ T-cells were infected with wt JR-CSF, S142N or the K421D Env pseudotyped virus, and the infection of the indicated CD4+ T-cell subsets was assessed via intracellular p24 staining and multiparametric FACS analysis three days post-infection. The overall levels of infection, as determined by the percentage of p24+ cells, were consistent with the luciferase reporter results observed in FIG. 22(A) with S142N infecting the greatest proportion of cells and K421D the lowest (FIG. 22(B)). In most cases, the majority of p24+ cells were CD4+ T-central memory cells ($T_{CM}$, CCR7+CD45RO+), with the remainder comprising the effector memory subset ($T_{EM}$, CCR7−CD45RO+) or the naïve T-cell subset ($T_{naive}$, CCR7+CD45RO−) (FIG. 22 (C-D)). Interestingly, the S142N mutant demonstrated not only an increase in overall infectivity, but also an altered pattern of cellular tropism. Compared to wt JR-CSF, the S142N mutant infected almost 4-fold more naïve T-cells (25.9% vs 6.8%) and 2-fold more TEM cells (21.8% vs 12.4%). As a consequence, S142N infected fewer TCM cells compared to wt JR-CSF (48.5% vs 79.9%) (FIG. 22(C)). Although K421D infected fewer CD4+ T-cells, the CD4+ T-cell subset distribution resembled that of wt JR-CSF infection. Thus, the differential ability to use CCR5 as quantified by the GGR Affinofile assay is reflected in the differential ability of the wt and mutant JR-CSF Envs (S142N) to infect CD4+ T-cell subsets where CD4 expression is relatively high and uniform, where CCR5 expression is low and variable (Lee et al., 1999; Oswald-Richter et al., 2007). The results indicate that the differential entry efficiencies quantified by the GGR Affinofile system can reveal biologically relevant properties with regards to primary CD4+ T-cell subset tropism.

An accumulating body of evidence indicates that the majority of primary infections are established by a single viral clone (Virgin & Walker, 2010; Haase, 2010; Grivel et al., 2010). To discern whether relevant differences in entry efficiencies exist between T/F and chronic Envs, the GGR Affinofile system was used to examine the infectivity of T/F Envs (isolated from acutely infected Feinberg stage II or III patients) (46), and compared their infectivity metrics (θ,Δ, M) with those from a standard panel of chronic Envs. The specific clones used are indicated in Table 3. The infectivity profile of each T/F and chronic Env was examined at 25 distinct CD4/CCR5 expression levels (FIG. 27), and their infectivity metrics (FIG. 23(A-C)) were obtained via VERSA.

FIG. 23(A) shows that T/F Envs have a median θ that is significantly lower than that of chronic Envs (15° vs 25°, p=0.0003), and that this lower θ was also associated with a lower Δ (vector amplitude) (FIG. 23(C)). This correlation indicates that although the infectivity of T/F Envs is more dependent on changes in CD4 levels (lower θ), the gradient of the infectivity response to increasing CD4 levels is still less than that of chronic Envs (smaller Δ), especially at lower, more physiological levels of CCR5. This can be seen in FIGS. 23(D and E), which compares the infectivity response of T/F and chronic Envs as a function of CD4 levels at low (FIG. 23(D)) and high (FIG. 23 (E)) levels of CCR5. The wedge plot in FIG. 23(F) also shows that the T/F Envs can be phenotypically segregated from the chronic Envs on the basis of their θ and Δ metrics, at least within the cohort of subtype B Envs examined. Finally, the 2-D contour plots of the averaged infectivity between T/F and chronic Envs across a spectrum of CD4/CCR5 expression levels help highlight the differences indicated by their infectivity metrics: that at low to moderate levels of CCR5 (0-0.5 μM Pon), only the highest level of CD4 allowed efficient entry for the T/F Envs (FIG. 23(G), compare upper right quadrants). This phenotype is consistent with the observation that T/F Envs, despite being universally CCR5-using, are almost always primary T-cell tropic (high CD4/low CCR5) and not macrophage-tropic (low CD4/high CCR5) (Salazar-Gonzalez et al., 2009).

The GGR Affinofile cells were used to characterize a panel of 28 subtype A, B, C and D Envs (Table 4). The infectivity data for each subtype Env examined are shown in FIG. 28. As might be expected from a random panel of subtype Envs, there was a high degree of intra- and inter-subtype variability in all three metrics (FIG. 24(A)). Despite this, significant differences in CD4/CCR5 usage patterns between HIV-1 subtypes can be appreciated. For example, subtype C Envs had the highest A and M values (FIG. 24(A)), indicating that subtype C Envs, as a group, used CCR5 more efficiently than Envs from other HIV-1 subtypes. The infectivity data confirms that subtype C Envs do, indeed, achieve a higher level of infection in response to increasing CCR5 levels, especially when CD4 levels are limiting (FIG. 24(B), compare the lower left quadrants). Interestingly, when CCR5 levels are low, subtype C Envs exhibited markedly reduced levels of infectivity compared to Envs from other HIV-1 subtypes, even at the highest CD4 levels (FIG. 24(B), upper right quadrants). This particular nuance, although evident from the infectivity profile, is not captured by current Affinofile metrics. Finally, Envs from both HIV-1 subtypes A and C have significantly higher M values than subtype B Envs (FIG. 24(A)). The polar plot in FIG. 24(C) shows that subtype C envelopes can be clearly differentiated from other subtype envelopes based on their A and M metrics even if the amplitudes (Δ) do not differ significantly between the subtypes.

Recent technological advancements have resulted in the cloning and characterization of numerous broadly neutralizing antibodies (BNabs) with increased potency and breath of coverage compared to the "classical" BNAbs such as b12, 2G12 and 2F5. PG9/PG16 and VRC01 represent two of the major classes of these "next generation" BNAbs with non-overlapping epitopes (Walker et al., 2009; Zhou et al., 2010; Li et al., 2011). Despite the breath and potency of these BNAbs, single point mutations, N160K and N279/280A, can confer resistance to PG9/PG16 and VRC01, respectively (Walker et al., 2009; Li et al., 2011). N160 and N279/280 are highly conserved residues across HIV-1 subtypes suggesting that these residues are under selective pressure.

To determine whether these BNAb resistance mutants have any consequence on the entry efficiency of the resulting Env, resistant N160K and N279/280A mutants were generated in 24 Envs representing subtypes A through D, and their CD4/CCR5 entry efficiencies were examined in the GGR Affinofile system. FIG. 25(A-C), shows the infectivity profiles for all 36 wt Envs, N160K, and N279/280A mutants, each Env examined across 25 distinct CD4/CCR5 expression levels. Compared to the wt counterparts, the PG9/PG16 (N160K) and VRC01 (N279/280A) resistance mutations reduce the efficiency of entry; both requiring higher levels of CD4 and CCR5 to achieve similar levels of infection as their wt counterparts. This can be appreciated by comparing the CD4/CCR5 expression level combinations that give rise to low levels of infection (green areas), or conversely, those that give rise to the highest level of infection (red areas), between the wt and mutant Envs (FIG. 25(A-C)). This phenotype of reduced entry efficiency across all subtypes tested is quantitatively reflected in the M values, where the average M for PG9/PG16 and VRC01 resistant mutants is lower than that of their wt counterparts (FIG. 25(D-E)).

However, due to marked variability when comparing across all HIV-1 subtypes, only the difference between VRC01 resistance mutants and wt reached significance (p=0.0065). The results suggest that resistance to BNAbs comes at the cost of reduced HIV-1 entry efficiency, and provides one functional explanation for the high conservation of these residues across HIV-1 subtypes. Both these reasons bode well for vaccine design that will elicit these kinds of BNAbs.

GGR cells can also detect the presence of HIV in patient plasma samples. GGR cells were maximally induced with doxycycline (4 ng/ml) and ponasterone (4 uM) at the time of their seeding. 16-21 hours post-seeding/induction, cells were infected with serial dilutions of HIV positive plasma in the presence of polybrene. Four days post infection supernatant was collected and assayed for Gaussia Luciferase expression. Results indicate virus can be detected from untreated HIV positive plasma (FIG. 29(A)). To determine if the use of a commercially available concentration reagent could improve the signal from HIV positive plasma, a small aliquot of HIV positive plasma was prepared according to the RETRO-CONCENTIN™ protocol. RETRO-CONCENTIN™ is a virus precipitation solution available from System Biosciences (Mountain View, Calif.). Concentrated virus samples were diluted and used to infect maximally induced GGR Affinofile cells in the presence or absence of polybrene or DEAE Dextran. Results demonstrate GGR cells can readily detect virus in concentrated and diluted samples (FIG. 29(B)). Table 2 shows the cumulative results and patient data of all the plasma samples tested so far.

TABLE 2

Results of patient testing

| Patient # | CD4 count (cells/mL) | Viral load (copies/mL) | On HAART | TZM-bl | GGR | Ghost X4/X5 |
|---|---|---|---|---|---|---|
| 1 | ND | 3,200,000 | Yes* | pos | pos | ND |
| 2 | ND | 1,600,000 | Yes* | pos | pos | ND |

GGR Affinofile Cells can also detect minor X4 quasispecies. The 293 based GGR Affinofile cells constitutively express a small but significant amount of the other primary HIV receptor CXCR4. To determine if the amount of CXCR4 present on GGR Affinofile cells support infection by X4-using-virus, cells were maximally induced and infected with mixtures of X4 and R5 viruses. Results indicate that X4-using-variants are readily detected by GGR Affinofile cells (FIG. 30(A)). A control experiment demonstrates that the infection is specifically inhibited (>90) when the matching coreceptor inhibitor is used (FIG. 30(B); CCR5 inhibitor, Maraviroc and/or CXCR4 inhibitor, AMD 3100).

The GGR cells are able to reveal subtle intrinsic resistance to an FDA approved inhibitor. Affinofile and GGR Affinofile cells have the ability to express CD4 and CCR5 at levels that are comparable to most HIV cell lines and relevant primary cells. Adjusting the amount of doxycycline and ponasterone A present finely induces the amount of CD4 and CCR5 expressed on Affinofile and GGR cells (FIG. 31(A)). HIV indicator cell lines with low to moderate levels CCR5 expression are unable to reveal the inherent ability of the maraviroc "sensitive" clone to use the maraviroc bound form of CCR5. This is true for the U87 CD4/CCR5 cell line used by LabCorp's Trofile Tropism assay. Only cells that express high levels of CCR5, such as NP2CD4/CCR5 and Affinofile/GGR cells, can reveal the inherent resistance of the clone (FIG. 31(B)). Affinofile cells induced to express distinct levels of CCR5 demonstrate that only in cells with high levels of CCR5 can the intrinsic resistance to maraviroc be revealed (FIG. 31(C)).

In the case of testing for phenotypic resistance to antiretroviral drugs, one can simply use viruses from primary patient samples and do IC50 curves of the various drugs on the described GGR cells when CD4 and coreceptor is maximally induced. This can, in principle, give the same result as the Phenosense™ assay now marketed and performed by Monogram Biosciences without the need for cloning individual gag-pol genes.

Given the versatility of the described GGR cell line, there are numerous practical applications for it. These include, but are not limited to:

The GGR cell line can be used to rapidly detect/test HIV entry, infection and replication efficiency overtime under various laboratory experimental conditions. It can be turned into a high-throughput test (scaleable to 384 well) that can support the multitude of clinical trials (vaccine and therapeutic trials).

The GGR cell line can be used to test for the efficiency of CD4 and co-receptor usage of cloned or uncloned envelopes derived from primary patient samples. These results will provide clinically useful information that will guide therapeutic options. For example, the GGR infectivity profile may suggest that the patient already has preexisting isolates that may not respond well (or conversely, will respond particularly well) to a give class of entry inhibitors based on vector metrics derived from the 3-D plot data exemplified in FIG. 4 (see description above).

The GGR cell line may simply be used to characterized the tropism profile of patient isolates prior to the prescription of CCR5 inhibitors. Current FDA rules require physicians to perform the Trofile™ test (again, licensed and performed only by Monogram Biosciences) and requires the presence of at least 80% R5-using envs in patient samples. The described GGR system can easily be modified to produce the same information (e.g., how much of the G.Luc activity is reduced by saturating concentrations of the CCR5 inhibitor that is to be prescribed). This provides an additional layer of information above and beyond the Trofile™ test marketed by monogram Biosciences. In addition, creation of the GGR system in other cell lines that lack endogenous CD4, CCR5 and CXCR4 (e.g., U87) allows one to directly profile CCR5 vs CXCR4 usage.

The IC50s for any antiretroviral (entry inhibitors, reverse transcriptase inhibitors, protease inhibitors, integrase inhibitors) can also be determined if the GGR system is scaled up. Full inhibition curves can be performed using patient derived viruses against all available antiretrovirals. The 384-well format when standardized will also represent economies of scale. As cloning is not required, the described GGR test will take a maximum of 72 hours compared to the 2-3 weeks required for the Phenosense™ assay performed by Monogram Biosciences. Genotyping resistance assays are available (based on sequencing) but they are not as comprehensive (by definition, they can only predict resistance based on a database of known mutations). Since replication-competent virus direct from patient plasma is used, extending the time of incubation or transferring the supernatant to a fresh panel of GGR cells may boost the sensitivity of the assay.

The described GGR system can be used as a test for acute infection. Persons infected with HIV do not develop detectable anti-HIV antibodies until about 3 months post-infection (but no earlier than 6 weeks post-infection). However, acutely infected individuals develop an influenza-like illness during the peak of viral replication in the first 2-4 weeks post-infection, leading many of them to seek health care from their primary physicians or the ER. Viral loads determined by qRT-PCR or branched chain DNA assay are generally in the hundred of thousands if not millions during this period. The high viral load suggests that the described GGR system is ideally suited to detect viruses from these acutely infected individuals, and the viruses themselves can be cloned out from the virally infected GGR cells (which will be green). There is an international consortium aimed at isolating and cloning out as many acutely transmitted viral clones as possible in the hopes of understanding the characteristics of these transmitted clones.

The GGR cell line can be used to propagate HIV from media or serum at varying levels of receptor and co-receptor levels. This flexibility of applying selective pressure only at the level of CD4 and co-receptor usage will provide invaluable tools for the research and pharmaceutical industry as they try to understand the evolution of viral receptor usage and the resistance to co-receptor entry inhibitors. The other class of entry inhibitors (Fuzeon, Roche) is a fusion peptide inhibitor that may also be affected by the levels of CD4 and CCR5 even though it inhibits the fusion step post-receptor binding (receptor binding affinity can affect the speed of the fusion conformational cascade, which is correlated with the sensitivity to this fusion peptide inhibitor).

The GGR cell line can also be used to monitor the relative resistance or sensitivity to neutralizing antibodies. There is another international effort mounted by the IAVI (International AIDS Vaccine Initiative) as well as by the VRC (Vaccine Research Center) at the NIH to develop broadly neutralizing antibodies. In the last few years, much excitement has been focused on the development of so-called broadly neutralizing antibodies. Mutations have inevitably developed against some of these broadly neutralizing antibodies. In the majority of the cases tested, resistance to broadly neutralizing antibodies comes at a fitness cost, in that the resistant virus can no longer uses CD4 and co-receptor as efficiently as the parental neutralization sensitive virus. The described GGR system (and admittedly our 293-Affinofile system) is the only way to quantify the efficiency of entry as an interdependent function of CD4 and CCR5 expression levels. When scaled up, this GGR system provides critical support for the various vaccine studies underway to generate immunogens for eliciting broadly neutralizing antibodies. In addition, even for "normal" neutralizing assays, the described GGR cell line provides a convenient and high throughput way for monitoring neutralization resistance or sensitivity (which may well depend on the level of CD4 and co-receptor on the target cell).

The GGR indicator cell line has been engineered in its entirety. The sensitivity of infectious HIV detection with pseudotype and replication competent virus has been demonstrated. The infectious unit sensitivity for HIV in spiked human serum (~1,000 TCID50) has been established.

The sensitivity of detection could be further improved by various strategies (e.g., the use of anti-CD44 miltenyi beads which help to concentrate primary viral isolates onto the surface of target cells—this anti-CD44 Miltenyi beads is actually being marketed for isolating virus in patient samples with low viremia). Other reagents have been shown to enhance HIV infection by promoting the interaction between the virus particle and the cell. These include, but are not limited to DEAE Dextran; Polybrene; Protamine sulfate; and Fibronectin.

In addition, the third generation of "GGR" cells can be produced by knocking in all the required constructs for the dual inducible system into the same genomic locus. Once that clone is established, there will be no limits with regards to its flexibility as any gene can be knocked in to replace CD4 and/or CCR5 (CXCR4 for example) in the same genomic locus. Thus, any two genes of relevance can be simultaneously and independently induced.

Table 3, below, provides a list of transmitter/founder (T/F) and chronic envelopes.

| Env type | env clone | Gender | Age | Feinberg Stage | Viral Load (copies/ml) | Disease Status | Location | Riskfactor | Accession Number | AIDS Repository Designation |
|---|---|---|---|---|---|---|---|---|---|---|
| T/F | p6244_13.B5.4576 | M | | II | 274,000 | NA | USA | SPD | EU289191 | P6244_13.B5.4576 |
| | p63358.p3.4013 | NR | | II | 260,000 | NA | USA | SPD | EU289192 | p63358.p3.4013 |
| | p700D10040.C9.4520 | F | | II | 741,499 | NA | USA | IVDU | EU289193 | p700010040.C9.4520 |
| | p1054.TC4.1499 | M | | II | 320,000 | NA | USA | SPD | EU289185 | p1054.TC4.1499 |
| | pPRB926_04.A9.4237 | NR | | II | 756,000 | NA | USA | SPD | EU289197 | pPRB926_04.A9.4237 |
| | pSC45.4B5.2631 | M | | II | 6,318,529 | NA | Trinidad | Heterosexual | EU289201 | pSC45.4B5.2631 |

| Env type | env clone | b12 $IC_{50}$ (ug/ml) | sCD4 $IC_{50}$ (nM) | T415 (Yes/No) |
|---|---|---|---|---|
| T/F | p6244_13.B5.4576 | >50 | 254 | N |
| | p63358.p3.4013 | >50 | 533 | N |
| | p700D10040.C9.4520 | 0.7 | 97 | N |
| | p1054.TC4.1499 | 4.2 | 113 | Y |
| | pPRB926_04.A9.4237 | 0.5 | 93 | N |
| | pSC45.4B5.2631 | 0.7 | 268 | N |

| Env type | env clone | Gender | Age | Time since sero-conversion | CD4 Count (cells/mm$^3$) | Disease Status | Location | Riskfactor | Accession Number | AIDS Repository Designation |
|---|---|---|---|---|---|---|---|---|---|---|
| Chronic | 92TH014.12 | M | 38 | 25.6 | ND | AS | Bangkok, Thailand | IVDU | U08801 | pSVIII-92TH014.12 |
| | 92US711.14 | M | 44 | 17 | 853 | AS | Baltimore, USA | IVDU | U08448 | pBA301711.14 |
| | 92US712.4 | F | 35 | 15 | 537 | AS | Baltimore, USA | IVDU | U08449 | pBA301712.4 |
| | 92US714.1 | M | 28 | 12 | 546 | AS | Baltimore, USA | IVDU | U08450 | pBA301714.1 |
| | 92US715.6 | M | 36 | 20 | 470 | AS | Baltimore, USA | IVDU | U08451 | pBA301715.6 |
| | 92US716.6 | M | 39 | 4 | 787 | AS | Baltimore, USA | IVDU | U03452 | pBA301716.6 |

NA, non-applicable
AS, asymptomatic
NR, not recorded

**Risk behavior where known. Subjects listed as "SPD" were source plasma donors who denied having sex for money, homosexual activity, IVDU, or receiving a blood transfusion or a tattoo in the preceding year.

Table 4, below, provides a list of subtype envelopes.

| Env subtype | Env clone | Approximate length of time of infection* | Viral Load (copies/ml) | CD4 Count (cells/mm³) | Location | Mode of Transmission | Accession Number | Reference | Group PI | b12 1C₅₀ (ug/ml) | sCD4 IC₅₀ (mg/ml) |
|---|---|---|---|---|---|---|---|---|---|---|---|
| A1 | Q259env.w6 | 81 dpi | 2,000,000 | NA | Kenya | NA | AF407151 | 1 | Overbaugh | >20 | NA |
| A2 | QB726.70M.ENV.B3 | 70 dpi | 61,940 | NA | Kenya | NA | FJ866111 | 1 | Overbaugh | >20 | NA |
| A3 | QH359.21M.ENV.C1 | 21 dpi | 32,120 | NA | Kenya | NA | FJ866121 | 2 | Overbaugh | >20 | NA |
| A4 | QH209.14M.ENV.A2 | 14 dpi | 28,600 | NA | Kenya | NA | FJ866118 | 2 | Overbaugh | >20 | NA |
| A5 | QF495.23M.ENV.A3 | 23 dpi | 217,050 | NA | Kenya | NA | FJ866114 | 2 | Overbaugh | >20 | NA |
| A6 | Q769env.h5 | 61 dpi | 9,000,000 | NA | Kenya | NA | AF407159 | 2 | Overbaugh | >20 | NA |
| A7 | QH343.21M.ENV.A10 | 21 dpi | 40,750,000 | NA | Kenya | NA | FJ866119 | 2 | Overbaugh | >20 | NA |
| B1 | SC 422661.8 (SVPB8) | 4 wks | 1,380,000 | ND | Trinidad | F-M | AY835441 | 3 | Montefiori | 4.7 | 0.2 |
| B2 | pCAAN5342 clone A2 | NA | >1,000,000 | 278 | USA | M-M | AY835452 | 3 | Montefiori | >50 | 16 |
| B3 | pREIO4541 clone 67 | 2 wks | 722,349 | 848 | USA | F-M | AY835449 | 3 | Montefiori | 0.7 | 0.5 |
| B4 | pTRIO4551clone 58 | 1 wks | 8122951 | NA | USA | M-M | AY835450 | 3 | Montefiori | >50 | 20.2 |
| B5 | AC10.0, clone 29 | 4 wks | 40,700 | 919 | USA | M-M | AY835446 | 3 | Montefiori | 1.8 | 8.5 |
| B6 | QH0692, clone 42 | 6 wks | 9,611 | NA | Trinidad | F-M | AY835439 | 3 | Montefiori | 0.3 | 0.5 |
| B7 | pRHPA4259 clone 7 | <8 wks | 1,458,354 | 247 | USA | M-F | AY835447 | 3 | Montefiori | 0.1 | 1.8 |
| C1 | HIV-16055-2, | 2 days | 534,557 | 830 | India | F-M | EF117268 | 4 | Montefiori | >50 | 11.4 |
| C2 | HIV-16845-2, | 20 days | 199,655 | 579 | India | M-F | EF117269 | 4 | Montefiori | >50 | 1 |
| C3 | HIV-25710-2, | 19 | 3523 | 350 | India | F-M | EF117271 | 4 | Montefiori | >50 | 2.6 |
| C4 | HIV-25711-2, | 4 days | 6,633,880 | 471 | India | F-M | EF117272 | 4 | Montefiori | 25.9 | 29 |
| C5 | HIV-26191-2, | 9 days | 5,346,070 | 338 | India | F-M | EF117274 | 4 | Montefiori | 4.9 | 17.1 |
| C6 | HIV-00836-2, | 85 days | 31,104 | ND | India | M-F | EF117265 | 4 | Montefiori | >50 | >50 |
| C7 | HIV-001428-2, clone 42 | 11 days | 217,812 | 454 | India | M-F | EF117266 | 4 | Montefiori | >50 | 5.2 |
| D1 | QA013.701.ENV.H1 | 70 dpi | 1,527,700 | NA | Kenya | NA | FJ866134 | 2 | Overbaugh | >20 | NA |
| D2 | QA013.701.ENV.M12 | 70 dpi | 1,527,700 | NA | Kenya | NA | FJ866135 | 2 | Overbaugh | >20 | NA |
| D3 | QA465.59M.ENV.D1 | 59 dpi | 37,750 | NA | Kenya | NA | FJ866137 | 2 | Overbaugh | 17.16 | NA |
| D4 | QD435.100M.ENV.B5 | 100 dpi | 17,470 | NA | Kenya | NA | FJ866140 | 2 | Overbaugh | >20 | NA |
| D5 | QD435.100M.ENV.A4 | 100 dpi | 17,470 | NA | Kenya | NA | FJ866139 | 2 | Overbaugh | >20 | NA |
| D6 | QD435.100M.ENV.E1 | 100 dpi | 17,470 | NA | Kenya | NA | FJ866141 | 2 | Overbaugh | >20 | NA |
| D7 | QA465.59M.ENV.A1 | 59 dpi | 37,750 | NA | Kenya | NA | FJ866136 | 2 | Overbaugh | 9.09 | NA |

NA, Not available;
NO, Not determined
*Defined differently in dffferent studies
*Approximate length of time of infection days post-infection asdefiend by RNA testing days post-infection asdefined by RNAtesting as determined by either the last known seronegative clinic visit, the time of onset of acute retroviral syndrome, or a combination of these two clinical parameters days after first p24 positive test

| Ref No. | Reference | Group PI |
|---|---|---|
| 1 | EM Long et al, ARHR 2002 | Julie Overbaugh |
| 2 | CA Blish et al, JV 2003 | Julie Overbaugh |
| 3 | M Li er al, JV 2005 | David Montefiori |
| 4 | SS Kulkarnl et al, Virology 2009 | David Montefiori |

Other characteristics and advantages of the invention appear in the Figures.

The following publications are incorporated herein by reference in their entireties for all purposes, as are other publications referenced herein:

REFERENCES

1. Agrawal-Gamse, C., F. H. Lee, et al. (2009). "Adaptive mutations in a human immunodeficiency virus type 1 envelope protein with a truncated V3 loop restore function by improving interactions with CD4." *J Virol* 83(21): 11005-11015.

2. Johnston, S. H., M. A. Lobritz, et al. (2009). "A quantitative affinity-profiling system that reveals distinct CD4/CCR5 usage patterns among human immunodeficiency virus type 1 and simian immunodeficiency virus strains." *J Virol* 83(21): 11016-11026.

3. Lassen, K. G., M. A. Lobritz, et al. (2009). "Elite suppressor-derived HIV-1 envelope glycoproteins exhibit reduced entry efficiency and kinetics." *PLoS Pathog* 5(4): e1000377.

4. Pfaff, J. M., C. B. Wilen, et al. (2010). "HIV-1 resistance to CCR5 antagonists associated with highly efficient use of CCR5 and altered tropism on primary CD4+ T cells." *J Virol* 84(13): 6505-6514.

5. Pugach, P., N. Ray, et al. (2009). "Inefficient entry of vicriviroc-resistant HIV-1 via the inhibitor-CCR5 complex at low cell surface CCR5 densities." *Virology* 387(2): 296-302.

6. Roche, M., M. R. Jakobsen, et al. (2011). "HIV-1 predisposed to acquiring resistance to maraviroc (MVC) and other CCR5 antagonists in vitro has an inherent, low-level ability to utilize MVC-bound CCR5 for entry." *Retrovirology* 8: 89.

7. Roche, M., M. R. Jakobsen, et al. (2011). "HIV-1 escape from the CCR5 antagonist maraviroc associated with an altered and less-efficient mechanism of gp120-CCR5 engagement that attenuates macrophage tropism." *J Virol* 85(9): 4330-4342.

8. Sterjovski, J., M. Roche, et al. (2010). "An altered and more efficient mechanism of CCR5 engagement contributes to macrophage tropism of CCR5-using HIV-1 envelopes." *Virology* 404(2): 269-278.

9. Wu Y., Beddall, M. H., & J. W. Marsh (2007) Rev-dependent lentiviral expression vector. Retrovirology 4(1):12.

10. Chikere K., Chou, T., Gorry, P. R., & B. Lee (2012) Affinofile Profiling: How the Efficiency of CD4/CCR5 usage impacts the biological and pathogenic phenotype of HIV. *Virology* 2012.09.043.
11. Lee, B., Sharron, M., Montaner, L. J., Weissman, D., and R. W. Doms (1999) Quantification of CD4, CCR5, and CXCR4 levels on lymphocyte subsets, dendritic cells, and differentially conditioned monocyte-derived macrophages. *Proc Natl Acad Sci USA* 96(9):5215-5220.
12. Dejucq, N., Simmons, G., & Clapham, P. R. (1999) Expanded tropism of primary human immunodeficiency virus type 1 R5 strains to CD4(+) T-cell lines determined by the capacity to exploit low concentrations of CCR5. *J Virol* 73(9):7842-7847.
13. Boyd, M. T., Simpson, G. R., Cann, A. J., Johnson, M. A., & R. A. Weiss (1993) A single amino acid substitution in the V1 loop of human immunodeficiency virus type 1 gp120 alters cellular tropism. *J Virol* 67(6):3649-3652.
14. Reeves, J. D. (2002) Sensitivity of HIV-1 to entry inhibitors correlates with envelope/coreceptor affinity, receptor density, and fusion kinetics. *Proc Natl Acad Sci USA* 99(25):16249-16254.
15. Rizzuto, C. D. (1998) A Conserved HIV gp120 Glycoprotein Structure Involved in Chemokine Receptor Binding. *Science* 280(5371):1949-1953.
16. Oswald-Richter, K., et al. (2007) Identification of a CCR5-expressing T cell subset that is resistant to R5-tropic HIV infection. *PLoS Pathog* 3(4):e58.
17. Virgin, H. W. & Walker, B. D. (2010) Immunology and the elusive AIDS vaccine. *Nature* 464(7286):224-231.
18. Haase, A. T. (2010) Targeting early infection to prevent HIV-1 mucosal transmission. *Nature* 464(7286):217-223.
19. Grivel J-C, Shattock, R. J., & Margolis, L. B. (2010) Selective transmission of R5 HIV-1 variants: where is the gatekeeper? *J Transl Med* 9(Suppl 1):S6.
20. Salazar-Gonzalez J F, et al. (2009) Genetic identity, biological phenotype, and evolutionary pathways of transmitted/founder viruses in acute and early HIV-1 infection. *J Exp Med* 206(6):1273-1289.
21. Walker, L. M., et al. (2009) Broad and potent neutralizing antibodies from an African donor reveal a new HIV-1 vaccine target. *Science*, United States, Vol 326, pp 285-289.
22. Zhou, T., et al. (2010) Structural Basis for Broad and Potent Neutralization of HIV-1 by Antibody VRC01. *Science* 329(5993):811-817.
23. Li, Y., et al. (2011) Mechanism of neutralization by the broadly neutralizing HIV-1 monoclonal antibody VRC01. *J Virol, United States*, Vol 85, pp 8954-8967.

What is claimed is:

1. A vector comprising the transactivators of the tetracycline and ponasterone inducible systems and the FRT-Lac-Zeo selection cassette wherein the vector allows inducible expression of two genes of interest and a high expression of the selectable markers LacZ and Zeocin, wherein the transactivator of tetracycline is operably linked to VGECR of the transactivator of ponasterone by a P2A ribosome skipping sequence, and wherein a RSV 5' LTR promoter is operably linked to RKR of the transactivator of ponasterone.

2. The vector according to claim 1, wherein the vector is represented in FIG. 13.

3. A cell line comprising the vector identified in claim 1.

4. A method for creating a cell line that can be made to regulate the expression of any two genes placed under the respective inducible promoter comprising transfecting a cell with the vector of FIG. 13.

5. A vector as set forth in FIG. 32.

6. A cell line comprising the vector identified in claim 5.

7. A cell line created from the method according to claim 4.

8. A method for controlling the expression of any two genes of interest comprising transfecting a cell with the vector of FIG. 13.

* * * * *